(12) United States Patent
Rafferty et al.

(10) Patent No.: US 9,579,040 B2
(45) Date of Patent: Feb. 28, 2017

(54) ELECTRONICS FOR DETECTION OF A CONDITION OF TISSUE

(75) Inventors: Conor Rafferty, Newton, MA (US); Jeffrey D. Carbeck, Belmont, MA (US); Alexander Dickson, Darien, CT (US); Kevin Dowling, Westford, MA (US); Yung-Yu Hsu, Cambridge, MA (US); Isaiah Kacyvenski, Weston, MA (US); Benjamin Schlatka, Lexington, MA (US); Henry Wei, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 827 days.

(21) Appl. No.: 13/603,290

(22) Filed: Sep. 4, 2012

(65) Prior Publication Data

US 2013/0245388 A1     Sep. 19, 2013

Related U.S. Application Data

(60) Provisional application No. 61/530,283, filed on Sep. 1, 2011, provisional application No. 61/540,421, filed
(Continued)

(51) Int. Cl.
*A61B 5/00* (2006.01)
*A61B 5/053* (2006.01)
(Continued)

(52) U.S. Cl.
CPC .......... *A61B 5/0537* (2013.01); *A61B 5/0002* (2013.01); *A61B 5/0024* (2013.01); *A61B 5/01* (2013.01);
(Continued)

(58) Field of Classification Search
CPC combination set(s) only.
See application file for complete search history.

(56) References Cited

U.S. PATENT DOCUMENTS 3,716,861 A   2/1973  Root
3,805,427 A   4/1974  Epstein
(Continued)

FOREIGN PATENT DOCUMENTS

JP      2003339699 A    12/2003
JP      2005052212 A     3/2005
(Continued)

OTHER PUBLICATIONS

Demura et al., "Immobilization of Glucose Oxidase with Bombyx Mori Silk Fibroin by Only Stretching Treatment and its Application to Glucose Sensor," Biotechnology and Bioengineering, vol. 33, 598-603 (6 pages) (1989).
(Continued)

*Primary Examiner* — Michael Kahelin
*Assistant Examiner* — Mitchell E Alter
(74) *Attorney, Agent, or Firm* — Nixon Peabody LLP

(57) ABSTRACT

Apparatus are provided for monitoring a condition of a tissue based on a measurement of an electrical property of the tissue. In an example, the electrical property of the tissue is performed using an apparatus disposed above the tissue, where the apparatus includes at least two conductive structures, each having a non-linear configuration, where the at least two conductive structures are disposed substantially parallel to each other. In another example, the electrical property of the tissue is performed using an apparatus disposed above the tissue, where the apparatus includes at least one inductor structure.

48 Claims, 28 Drawing Sheets

Related U.S. Application Data on Sep. 28, 2011, provisional application No. 61/541,762, filed on Sep. 30, 2011, provisional application No. 61/649,035, filed on May 18, 2012, provisional application No. 61/681,545, filed on Aug. 9, 2012.

(51) Int. Cl.

| | | |
|---|---|---|
| *A61B 5/01* | (2006.01) | |
| *A61B 5/04* | (2006.01) | |
| *A61B 8/00* | (2006.01) | |
| A61B 5/0476 | (2006.01) | |
| A61B 5/0245 | (2006.01) | |
| A61B 5/0402 | (2006.01) | |
| A61B 5/0488 | (2006.01) | |

(52) U.S. Cl.
CPC .............. *A61B 5/04* (2013.01); *A61B 5/4266* (2013.01); *A61B 5/442* (2013.01); *A61B 5/6831* (2013.01); *A61B 5/6832* (2013.01); *A61B 5/6833* (2013.01); *A61B 5/7282* (2013.01); *A61B 8/4416* (2013.01); *A61B 5/0245* (2013.01); *A61B 5/0402* (2013.01); *A61B 5/04012* (2013.01); *A61B 5/0476* (2013.01); *A61B 5/0488* (2013.01); *A61B 5/441* (2013.01); *A61B 5/443* (2013.01)

(56) References Cited

U.S. PATENT DOCUMENTS

| | | | |
|---|---|---|---|
| 5,633,532 A | 5/1997 | Sohara | |
| 5,817,008 A | 10/1998 | Rafert et al. | |
| 5,907,477 A | 5/1999 | Tuttle et al. | |
| 6,063,046 A | 5/2000 | Allum | |
| 6,784,844 B1 | 8/2004 | Boakes et al. | |
| 7,265,298 B2 | 9/2007 | Maghribi | |
| 7,302,751 B2 | 12/2007 | Hamburgen | |
| 7,337,012 B2 | 2/2008 | Maghribi | |
| 7,487,587 B2 | 2/2009 | Vanfleteren | |
| 7,491,892 B2 | 2/2009 | Wagner | |
| 7,521,292 B2 | 4/2009 | Rogers | |
| 7,525,304 B1* | 4/2009 | Feng .................. G01R 27/2605 324/762.01 |
| 7,557,367 B2 | 7/2009 | Rodgers | |
| 7,618,260 B2 | 11/2009 | Daniel et al. | |
| 7,622,367 B1 | 11/2009 | Nuzzo | |
| 7,759,167 B2 | 7/2010 | Vanfleteren | |
| 7,960,246 B2 | 6/2011 | Flamand | |
| 7,982,296 B2 | 7/2011 | Nuzzo | |
| 8,097,926 B2 | 1/2012 | De Graff | |
| 8,198,621 B2 | 6/2012 | Rogers | |
| 8,207,473 B2 | 6/2012 | Axisa | |
| 8,217,381 B2 | 7/2012 | Rodgers | |
| 8,372,726 B2 | 2/2013 | De Graff | |
| 8,389,862 B2 | 3/2013 | Arora | |
| 8,431,828 B2 | 4/2013 | Vanfleteren | |
| 8,440,546 B2 | 5/2013 | Nuzzo | |
| 8,536,667 B2 | 9/2013 | De Graff | |
| 8,552,299 B2 | 10/2013 | Rodgers | |
| 8,664,699 B2 | 3/2014 | Nuzzo | |
| 8,679,888 B2 | 3/2014 | Rodgers | |
| 8,729,524 B2 | 5/2014 | Rodgers | |
| 8,754,396 B2 | 6/2014 | Rogers | |
| 8,865,489 B2 | 10/2014 | Rodgers | |
| 8,886,334 B2 | 11/2014 | Ghaffari | |
| 8,905,772 B2 | 12/2014 | Rodgers | |
| 9,012,784 B2 | 4/2015 | Arora | |
| 2002/0094701 A1 | 7/2002 | Biegelsen et al. | |
| 2002/0095087 A1* | 7/2002 | Mourad .................. A61B 5/0048 600/442 |
| 2002/0113739 A1 | 8/2002 | Howard | |
| 2003/0214408 A1 | 11/2003 | Grajales | |
| 2004/0243204 A1 | 12/2004 | Maghribi | |
| 2005/0070778 A1 | 3/2005 | Lackey | |
| 2005/0096513 A1 | 5/2005 | Ozguz | |
| 2005/0115308 A1* | 6/2005 | Koram .............. B32B 17/10036 73/73 |
| 2005/0177223 A1* | 8/2005 | Palmaz ................ A61B 5/0031 623/1.15 |
| 2006/0038182 A1 | 2/2006 | Rodgers | |
| 2006/0248946 A1 | 11/2006 | Howell | |
| 2006/0264767 A1 | 11/2006 | Shennib | |
| 2006/0286785 A1 | 12/2006 | Rogers | |
| 2007/0123756 A1 | 5/2007 | Kitajima et al. | |
| 2008/0046080 A1 | 2/2008 | Vanden Bulcke | |
| 2008/0139894 A1 | 6/2008 | Szydlo-Moore et al. | |
| 2008/0157235 A1 | 7/2008 | Rodgers | |
| 2008/0204021 A1 | 8/2008 | Leussler et al. | |
| 2008/0249576 A1 | 10/2008 | Johnson et al. | |
| 2009/0000377 A1 | 1/2009 | Shipps et al. | |
| 2009/0048556 A1 | 2/2009 | Durand | |
| 2009/0105605 A1* | 4/2009 | Abreu .................. A61B 5/0008 600/549 |
| 2009/0107704 A1 | 4/2009 | Vanfleteren | |
| 2009/0261828 A1 | 10/2009 | Nordmeyer-Massner | |
| 2009/0294803 A1 | 12/2009 | Nuzzo | |
| 2009/0322480 A1 | 12/2009 | Benedict et al. | |
| 2010/0002402 A1 | 1/2010 | Rodgers | |
| 2010/0059863 A1 | 3/2010 | Rogers | |
| 2010/0072577 A1 | 3/2010 | Nuzzo | |
| 2010/0087782 A1 | 4/2010 | Ghaffari | |
| 2010/0090824 A1 | 4/2010 | Rowell et al. | |
| 2010/0116526 A1 | 5/2010 | Arora | |
| 2010/0178722 A1 | 7/2010 | De Graff | |
| 2010/0245011 A1 | 9/2010 | Chatzopoulos et al. | |
| 2010/0271191 A1 | 10/2010 | De Graff | |
| 2010/0298895 A1 | 11/2010 | Ghaffari et al. | |
| 2010/0317132 A1 | 12/2010 | Rodgers | |
| 2010/0321161 A1 | 12/2010 | Isabell | |
| 2011/0018838 A1* | 1/2011 | Lee .................. G06F 3/044 345/174 |
| 2011/0034912 A1 | 2/2011 | De Graff et al. | |
| 2011/0054583 A1 | 3/2011 | Litt | |
| 2011/0101755 A1 | 5/2011 | Salter et al. | |
| 2011/0121822 A1 | 5/2011 | Parsche | |
| 2011/0140897 A1 | 6/2011 | Purks et al. | |
| 2011/0184320 A1 | 7/2011 | Shipps | |
| 2011/0215931 A1 | 9/2011 | Callsen | |
| 2011/0218756 A1 | 9/2011 | Callsen | |
| 2011/0218757 A1 | 9/2011 | Callsen | |
| 2011/0220890 A1 | 9/2011 | Nuzzo | |
| 2011/0277813 A1 | 11/2011 | Rodgers | |
| 2012/0016258 A1 | 1/2012 | Webster et al. | |
| 2012/0051005 A1* | 3/2012 | Vanfleteren .......... H01L 21/565 361/749 |
| 2012/0052268 A1 | 3/2012 | Axisa | |
| 2012/0065937 A1 | 3/2012 | De Graff | |
| 2012/0087216 A1 | 4/2012 | Keung et al. | |
| 2012/0092178 A1 | 4/2012 | Callsen | |
| 2012/0092222 A1 | 4/2012 | Kato et al. | |
| 2012/0157804 A1 | 6/2012 | Rodgers | |
| 2012/0172697 A1 | 7/2012 | Urman | |
| 2012/0226130 A1 | 9/2012 | De Graff | |
| 2012/0244848 A1 | 9/2012 | Ghaffari | |
| 2012/0256308 A1 | 10/2012 | Helin | |
| 2012/0266685 A1* | 10/2012 | Choi .................. G01L 1/20 73/774 |
| 2012/0316455 A1 | 12/2012 | Rahman et al. | |
| 2012/0327608 A1 | 12/2012 | Rodgers | |
| 2013/0041235 A1 | 2/2013 | Rogers et al. | |
| 2013/0099358 A1 | 4/2013 | Elolampi | |
| 2013/0100618 A1 | 4/2013 | Rogers | |
| 2013/0118255 A1 | 5/2013 | Callsen | |
| 2013/0150693 A1 | 6/2013 | D'Angelo | |
| 2013/0185003 A1 | 7/2013 | Carbeck | |
| 2013/0192356 A1 | 8/2013 | De Graff | |
| 2013/0200268 A1 | 8/2013 | Rafferty | |
| 2013/0211761 A1 | 8/2013 | Brandsma et al. | |
| 2013/0225965 A1 | 8/2013 | Ghaffari | |
| 2013/0245388 A1 | 9/2013 | Rafferty et al. | |
| 2013/0274562 A1 | 10/2013 | Ghaffari | |
| 2013/0313713 A1 | 11/2013 | Arora | |
| 2013/0316442 A1 | 11/2013 | Meurville et al. | |

(56) References Cited

U.S. PATENT DOCUMENTS

| | | |
|---|---|---|
| 2013/0316487 A1 | 11/2013 | De Graff |
| 2013/0320503 A1 | 12/2013 | Nuzzo |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rodgers |
| 2014/0188426 A1 | 7/2014 | Fastert |
| 2014/0191236 A1 | 7/2014 | Nuzzo |
| 2014/0216524 A1 | 8/2014 | Rodgers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rodgers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora et al. |
| 2015/0099976 A1 | 4/2015 | Ghaffari et al. |
| 2015/0100135 A1 | 4/2015 | Ives |

FOREIGN PATENT DOCUMENTS

| | | |
|---|---|---|
| WO | WO 2005/122285 A2 | 12/2005 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A2 | 4/2010 |
| WO | WO 2010/042653 A1 | 4/2010 |
| WO | WO 2010/042957 A2 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041507 A1 * | 4/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |

OTHER PUBLICATIONS

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Extended European Search Report for Application No. EP 12827709.2, mailed Jun. 5, 2015 (6 pages).

* cited by examiner

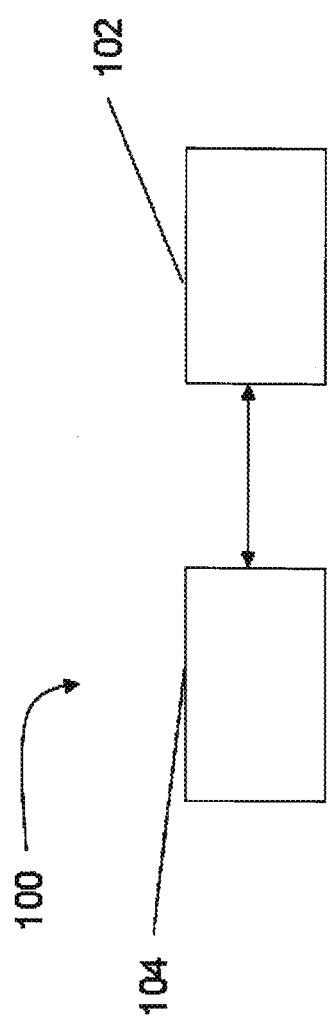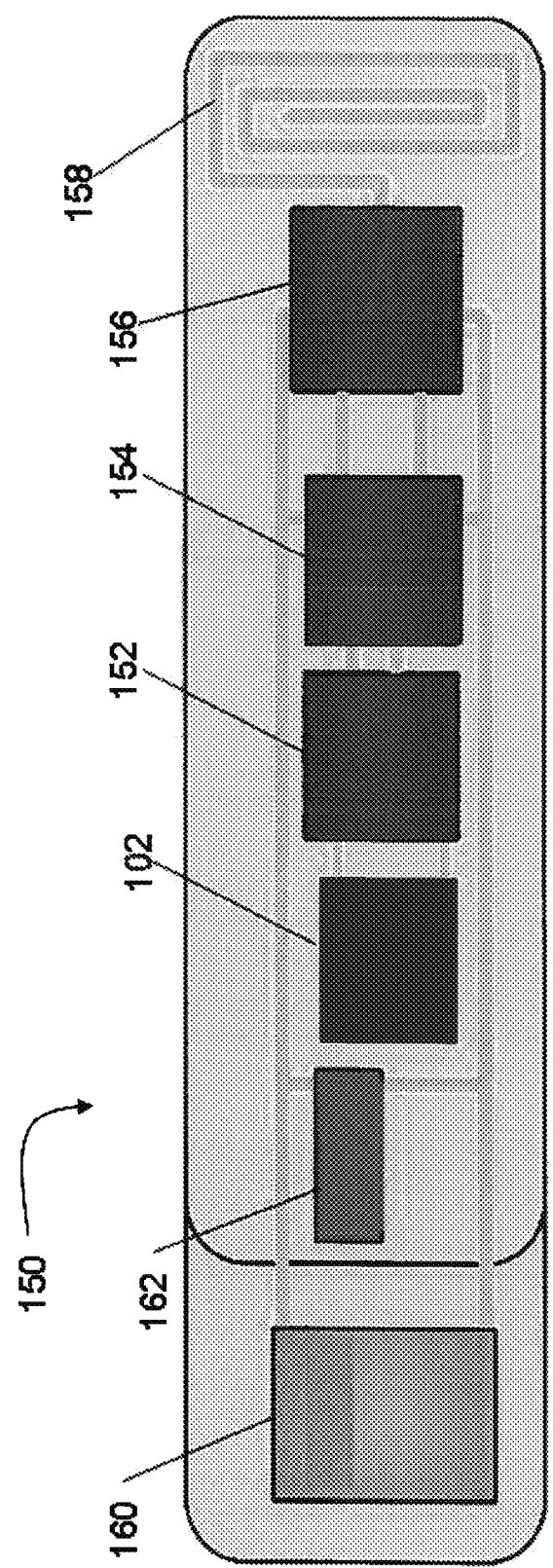

US 9,579,040 B2

ELECTRONICS FOR DETECTION OF A CONDITION OF TISSUE

CROSS-REFERENCES TO RELATED APPLICATIONS

This application claims priority to U.S. provisional application Ser. No. 61/530,283, filed Sep. 1, 2011, entitled "Methods, Apparatus, and Systems For Monitoring Hydration Via Conformal Electronics," U.S. provisional application Ser. No. 61/540,421, filed Sep. 28, 2011, entitled "Methods, Apparatus, and Systems For Monitoring Hydration Via Conformal Electronics," U.S. provisional application Ser. No. 61/541,762, filed Sep. 30, 2011, entitled "Methods, Apparatus, and Systems For Monitoring Hydration Via Conformal Electronics," U.S. provisional application Ser. No. 61/649,035, filed May 18, 2012, entitled "Monitoring Hydration Via Conformal Electronics," and U.S. provisional application Ser. No. 61/681,545, filed Aug. 9, 2012, entitled "Monitoring Hydration Via Conformal Electronics," each of which is hereby incorporated herein by reference in its entirety.

BACKGROUND

Effort is being made to develop electronics for application in measuring electrical properties of biological tissue. For example, effort is being made to develop electronics that can be applied to measure a property such as tissue hydration level.

Tissue hydration is the process of absorbing and retaining water in biological tissues. In humans, a significant drop in tissue hydration can lead to dehydration and may trigger other serious medical conditions. Dehydration may result from loss of water itself, loss of electrolytes, and/or a loss of blood plasma. Previous techniques for monitoring tissue hydration have applied, e.g., an ultrasonic hydration monitor that employs ultrasound velocity to calculate hydration level. The ultrasound hydration monitor is generally attached to tissue such as muscles. The device generally uses a rigid frame to maintain a constant distance between an ultrasound transducer and a receiver.

The use of electronics in such medical-related applications can be hampered by the boxy, rigid way that much electronics are designed and packaged. Biological tissue is mainly soft, pliable and curved. By contrast, boxy, rigid electronics can be hard and angular, which could affect the measurement of tissue.

SUMMARY

In view of the foregoing, it is recognized and appreciated herein that both sufficient comfort and accuracy are desirable attributes of techniques for monitoring tissue condition.

Various examples described herein are directed generally to tissue condition monitoring methods, apparatus, and systems applicable to both consumer and military markets, which can provide real-time feedback as well as portability. The tissue condition can be state of hydration or disease state. In some examples, the methods, apparatus and systems are based at least in part on measuring electrical properties of the skin and underlying tissue.

An example apparatus is described for monitoring a condition of a tissue. The apparatus includes at least two conductive structures disposed above the tissue, where each of the at least two conductive structures has a non-linear configuration, and where the at least two conductive structures are disposed substantially parallel to each other; at least two brace structures, each disposed substantially perpendicularly to the orientation of the at least two parallel conductive structures, and each being in electrical communication with at least one of the at least two parallel conductive structures; and at least one spacer structure that is physically coupled at each end to a portion of each of the at least two brace structures, such that a substantially uniform separation is maintained between the at least two brace structures. A measure of an electrical property of the tissue using the apparatus provides an indication of the condition of the tissue.

The condition of the tissue can be a hydration state of the tissue, a volume of sweat lost, a mechanical property of the tissue, a disease state of the tissue, or a level of SPF protection of the tissue.

For the example apparatus, each of the at least two conductive structures can have a zig-zag conformation, a serpentine configuration, or a rippled configuration.

Each of the at least two brace structures can be formed from a conductive material, and where each of the at least two brace structures electrically links the at least two conductive structures to an external circuit.

The at least two brace structures can be configured to maintain a separation of neighboring conductive structures of the at least two conductive structures to a substantially uniform value.

Each of the at least one spacer structure can be disposed substantially parallel to a principal direction of the at least two parallel conductive structures.

Each of the at least two brace structure can be in electrical communication with at least one electrical contact of the apparatus, where the at least one electrical contact is in electrical communication with at least one of a power source, a wireless receiver, a wireless transmitter, a wireless transceiver, and a temperature sensor.

The example apparatus can include a plurality of cross-link structures disposed between neighboring conductive structures, each cross-link structure of the plurality of cross-link structures being formed from a dielectric material.

The example apparatus can include an encapsulation layer disposed over at least a portion of the at least two conductive structures. In an example, portions of the encapsulation layer comprise an adhesive, where the adhesive attaches the portions of the encapsulation layer to the tissue.

The apparatus can include a plurality of cross-link structures disposed between neighboring conductive structures, each cross-link structure of the plurality of cross-link structures being formed from the same material as the encapsulation layer.

In an example, the encapsulation layer is a polymer. In another example, the polymer is a polyimide.

The example apparatus can include a backing layer in physical communication with at least a portion of the at least two conductive structures, where the backing layer is a polymer.

The apparatus in this example implementation can include an ultrasound apparatus, where the ultrasound apparatus provides a measure of an electrical property of the tissue. The ultrasound an apparatus can include an ultrasound generator disposed proximate to a first portion of the tissue of interest, where the ultrasound generator comprises a piezoelectric crystal, where the ultrasound generator directs ultrasound waves at a portion of the tissue; and an ultrasound receiver disposed proximate to a second portion of the tissue of interest that is different from the first portion. The ultrasound receiver provides a measure of ultrasound waves arriving at the second portion of the tissue. The measure of ultrasound waves arriving at the second portion of the tissue provides an indication of the condition of the tissue.

A system for monitoring a condition of a tissue is also provided. The example system includes at least one of any of the apparatus of this example implementation and at least one other component. The at least one other component can be at least one of a battery, a transmitter, a transceiver, a memory, a radio-frequency identification (RFID) chip, a processing unit, an analog sensing block, a UVA sensor, a UVB sensor, and a temperature sensor.

A method for monitoring a condition of a tissue is also provided. The method can include receiving data indicative of an electrical measurement of the tissue, where the electrical measurement is performed using at least one apparatus described herein; and analyzing the data using at least one processor unit, where the analysis provides an indication of the condition of the tissue.

In an example, the analyzing the data can include applying an effective circuit model to the data, where a value of a parameter of the model provides the indication of the condition of the tissue.

In another example, the analyzing the data can include comparing the data to a calibration standard, where the comparing provides the indication of the condition of the tissue. The calibration standard can include a correlation between values of electrical measurement and the indication of the condition of the tissue.

Another example apparatus for monitoring a condition of a tissue is described. The apparatus includes a plurality of conductive structures disposed above the tissue, where each of the plurality of conductive structures has a non-linear configuration, and where the plurality of conductive structures are disposed substantially parallel to each other in an interdigitated configuration; at least two brace structures, each disposed substantially perpendicularly to the orientation of the at least two parallel conductive structures, and each brace structure being in electrical communication with at least one of the plurality of conductive structures; and at least one spacer structure that is physically coupled at each end to a portion of each of the at least two brace structures, such that a substantially uniform separation is maintained between the at least two brace structures. A measure of an electrical property of the tissue using the apparatus provides an indication of the condition of the tissue.

For this example apparatus, the condition of the tissue can be a hydration state of the tissue, a volume of sweat lost, a mechanical property of the tissue, a disease state of the tissue, or a level of SPF protection of the tissue.

Each of the plurality of conductive structures can have a zig-zag conformation, a serpentine configuration, or a rippled configuration.

Each of the at least two brace structures can be formed from a conductive material, and where each of the at least two brace structures electrically links the plurality of conductive structures to an external circuit.

The at least two brace structures are configured to maintain a separation of neighboring conductive structures of the plurality of conductive structures to a substantially uniform value.

Each of the at least one spacer structure can be disposed substantially parallel to a principal direction of the at least two parallel conductive structures.

Each of the at least two brace structure can be in electrical communication with at least one electrical contact of the apparatus, where the at least one electrical contact is in electrical communication with at least one of a power source, a wireless receiver, a wireless transmitter, a wireless transceiver, and a temperature sensor.

In an example, the apparatus can include a plurality of cross-link structures disposed between neighboring conductive structures, each cross-link structure of the plurality of cross-link structures being formed from a dielectric material.

The example apparatus of this implementation can include an encapsulation layer disposed over at least a portion of the plurality of conductive structures. Portions of the encapsulation layer can include an adhesive, where the adhesive attaches the portions of the encapsulation layer to the tissue.

The example apparatus can include a plurality of cross-link structures disposed between neighboring conductive structures, each cross-link structure of the plurality of cross-link structures being formed from the same material as the encapsulation layer.

The encapsulation layer can be a polymer. In an example, the polymer is a polyimide.

The example apparatus can include a backing layer in physical communication with at least a portion of the plurality of conductive structures, where the backing layer is a polymer.

The apparatus in this example implementation can include an ultrasound apparatus, where the ultrasound apparatus provides a measure of an electrical property of the tissue. The ultrasound an apparatus can include an ultrasound generator disposed proximate to a first portion of the tissue of interest, where the ultrasound generator comprises a piezoelectric crystal, where the ultrasound generator directs ultrasound waves at a portion of the tissue; and an ultrasound receiver disposed proximate to a second portion of the tissue of interest that is different from the first portion. The ultrasound receiver provides a measure of ultrasound waves arriving at the second portion of the tissue. The measure of ultrasound waves arriving at the second portion of the tissue provides an indication of the condition of the tissue.

A system for monitoring a condition of a tissue is also provided. The example system includes at least one apparatus of this example implementation and at least one other component. The at least one other component can be at least one of a battery, a transmitter, a transceiver, a memory, a radio-frequency identification (RFID) chip, a processing unit, an analog sensing block, a UVA sensor, a UVB sensor, and a temperature sensor.

A method for monitoring a condition of a tissue is also provided. The method includes receiving data indicative of an electrical measurement of the tissue, where the electrical measurement is performed using at least one of the apparatus according to this example implementation and analyzing the data using at least one processor unit, where the analysis provides an indication of the condition of the tissue.

In an example, the analyzing the data can include applying an effective circuit model to the data, and where a value of a parameter of the model provides the indication of the condition of the tissue.

In another example, the analyzing the data can include comparing the data to a calibration standard, and where the comparing provides the indication of the condition of the tissue.

The calibration standard can include a correlation between values of electrical measurement and the indication of the condition of the tissue.

Another example apparatus for monitoring a condition of a tissue is also provided. The apparatus includes at least two conductive structures disposed above the tissue and running substantially parallel to each other along substantially an entire length of the conductive structures, where each of the conductive structures has a curved configuration; and at least two contact structures, each being in electrical communication with at least one of the at least two parallel conductive structures. A measure of an electrical property of the tissue using the apparatus provides a measure of the condition of the tissue.

In this example implementation, the condition of the tissue can be a hydration state of the tissue, a volume of sweat lost, a mechanical property of the tissue, a disease state of the tissue, or a level of SPF protection of the tissue.

Each of the plurality of conductive structures can have a zig-zag conformation, a serpentine configuration, or a rippled configuration.

Each of the at least two conductive structures is configured to maintain a separation of neighboring conductive structures of the at least two conductive structures to a substantially uniform value of distance.

Each of the at least two contact structures electrically links the at least two conductive structures to an external circuit.

Each of the at least two contact structures can be in electrical communication with at least one of a power source, a wireless receiver, a wireless transmitter, a wireless transceiver, and a temperature sensor.

In an example, the apparatus can include an encapsulation layer disposed over at least a portion of the at least two conductive structures. Portions of the encapsulation layer can include an adhesive, where the adhesive attaches the portions of the encapsulation layer to the tissue.

The encapsulation layer can be a polymer. In an example, the polymer is a polyimide.

The example apparatus according to this implementation can include at least one cross-link structure coupled at each end thereof to a portion of each of the least two conductive structures.

Each of the at least one cross-link structure can be disposed substantially perpendicularly to the portion of the at least two parallel conductive structures.

The example apparatus can include a plurality of cross-link structures disposed between the at least two conductive structures, each cross-link structure of the plurality of cross-link structures being formed from a dielectric material.

The example apparatus can include a plurality of cross-link structures disposed between neighboring conductive structures, each cross-link structure of the plurality of cross-link structures being formed from the same material as the encapsulation layer.

In an example, the encapsulation layer is a polymer. The polymer can be a polyimide.

The example apparatus can include a backing layer in physical communication with at least a portion of the at least two conductive structures, where the backing layer is a polymer.

The apparatus in this example implementation can include an ultrasound apparatus, where the ultrasound apparatus provides a measure of an electrical property of the tissue. The ultrasound an apparatus can include an ultrasound generator disposed proximate to a first portion of the tissue of interest, where the ultrasound generator comprises a piezoelectric crystal, where the ultrasound generator directs ultrasound waves at a portion of the tissue; and an ultrasound receiver disposed proximate to a second portion of the tissue of interest that is different from the first portion. The ultrasound receiver provides a measure of ultrasound waves arriving at the second portion of the tissue. The measure of ultrasound waves arriving at the second portion of the tissue provides an indication of the condition of the tissue.

A system is also provided for monitoring a condition of a tissue, where the system includes at least one apparatus of this example implementation and at least one other component. The at least one other component can be at least one of a battery, a transmitter, a transceiver, a memory, a radio-frequency identification (RFID) chip, a processing unit, an analog sensing block, a UVA sensor, a UVB sensor, and a temperature sensor.

A method for monitoring a condition of a tissue is also provided. The method includes receiving data indicative of an electrical measurement of the tissue, where the electrical measurement is performed using at least one apparatus of this example implementation and analyzing the data using at least one processor unit, where the analysis provides an indication of the condition of the tissue.

The analyzing the data can include applying an effective circuit model to the data, and where a value of a parameter of the model provides the indication of the condition of the tissue.

The analyzing the data can include comparing the data to a calibration standard, and where the comparing provides the indication of the condition of the tissue.

The calibration standard can include a correlation between values of electrical measurement and the indication of the condition of the tissue.

Another apparatus for monitoring a condition of a tissue is provided. The apparatus includes a substrate disposed above the tissue, where the substrate is formed from a material that changes a state with a change in the condition of the tissue, and at least one first inductor structure disposed above the substrate, where at least one of an electrical property and a physical property of the at least one first inductor structure changes with a change in the condition of the substrate. A measure of the electrical property or the physical property of the at least one first inductor structure provides an indication of the condition of the tissue.

The condition of the tissue can be a hydration state of the tissue, a volume of sweat lost, a mechanical property of the tissue, a disease state of the tissue, or a level of SPF protection of the tissue.

In an example, the first inductor structure can be a spiral coil structure, a cylindrical coil structure, or a toroidal structure.

In an example, the apparatus can include a reader, where the reader comprises at least one second inductor structure, where a measure of a change in an electrical property of the at least one second inductor structure brought in proximity to the at least one first inductor structure provides the measure of the electrical property of the at least one first inductor structure.

In an example, the second inductor structure is the same configuration as the first inductor structure.

In an example, the first inductor structure and the second inductor structure are a spiral coil structure, a cylindrical coil structure, or a toroidal structure.

The electrical property measured can be a magnetic flux density from the at least one first inductor structure.

In an example, the apparatus includes an encapsulation layer disposed over at least a portion of the at least one first inductor structure. The encapsulation layer can be a polymer.

In an example, portions of the polymer can include an adhesive, where the adhesive attaches the portions of the polymer to the tissue.

In an example, the can include a separator layer disposed between the at least one inductor structure and the substrate, where the separator layer is a non-conductive material.

The separator layer can be formed from a polymer.

The apparatus in this example implementation can include an ultrasound apparatus, where the ultrasound apparatus provides a measure of an electrical property of the tissue. The ultrasound an apparatus can include an ultrasound generator disposed proximate to a first portion of the tissue of interest, where the ultrasound generator comprises a piezoelectric crystal, where the ultrasound generator directs ultrasound waves at a portion of the tissue; and an ultrasound receiver disposed proximate to a second portion of the tissue of interest that is different from the first portion. The ultrasound receiver provides a measure of ultrasound waves arriving at the second portion of the tissue. The measure of ultrasound waves arriving at the second portion of the tissue provides an indication of the condition of the tissue.

A system is also for monitoring a condition of a tissue. The system includes at least one apparatus of this example implementation, and at least one other component. The at least one other component is at least one of a battery, a transmitter, a transceiver, a memory, a radio-frequency identification (RFID) chip, a processing unit, an analog sensing block, a UVA sensor, a UVB sensor, and a temperature sensor.

A method is also provided for monitoring a condition of a tissue. The method includes receiving data indicative of an electrical measurement of the tissue, where the electrical measurement is performed using at least one apparatus of this example implementation, and analyzing the data using at least one processor unit, where the analysis provides an indication of the condition of the tissue.

The analyzing the data can include applying an effective circuit model to the data, and where a value of a parameter of the model provides the indication of the condition of the tissue.

The analyzing the data can include comparing the data to a calibration standard, and where the comparing provides the indication of the condition of the tissue.

The calibration standard can include a correlation between values of electrical measurement and the indication of the condition of the tissue.

The following publications, patents, and patent applications are hereby incorporated herein by reference in their entirety:

Kim et al., "Stretchable and Foldable Silicon Integrated Circuits," Science Express, Mar. 27, 2008, 10.1126/science.1154367;

Ko et al., "A Hemispherical Electronic Eye Camera Based on Compressible Silicon Optoelectronics," Nature, Aug. 7, 2008, vol. 454, pp. 748-753;

Kim et al., "Complementary Metal Oxide Silicon Integrated Circuits Incorporating Monolithically Integrated Stretchable Wavy Interconnects," Applied Physics Letters, Jul. 31, 2008, vol. 93, 044102;

Kim et al., "Materials and Noncoplanar Mesh Designs for Integrated Circuits with Linear Elastic Responses to Extreme Mechanical Deformations," PNAS, Dec. 2, 2008, vol. 105, no. 48, pp. 18675-18680;

Meitl et al., "Transfer Printing by Kinetic Control of Adhesion to an Elastomeric Stamp," Nature Materials, January, 2006, vol. 5, pp. 33-38;

U.S. Patent Application publication no. 2010 0002402-A1, published Jan. 7, 2010, filed Mar. 5, 2009, and entitled "STRETCHABLE AND FOLDABLE ELECTRONIC DEVICES;"

U.S. Patent Application publication no. 2010 0087782-A1, published Apr. 8, 2010, filed Oct. 7, 2009, and entitled "CATHETER BALLOON HAVING STRETCHABLE INTEGRATED CIRCUITRY AND SENSOR ARRAY;"

U.S. Patent Application publication no. 2010 0116526-A1, published May 13, 2010, filed Nov. 12, 2009, and entitled "EXTREMELY STRETCHABLE ELECTRONICS;"

U.S. Patent Application publication no. 2010 0178722-A1, published Jul. 15, 2010, filed Jan. 12, 2010, and entitled "METHODS AND APPLICATIONS OF NON-PLANAR IMAGING ARRAYS;"

U.S. Patent Application publication no. 2010 027119-A1, published Oct. 28, 2010, filed Nov. 24, 2009, and entitled "SYSTEMS, DEVICES, AND METHODS UTILIZING STRETCHABLE ELECTRONICS TO MEASURE TIRE OR ROAD SURFACE CONDITIONS;"

PCT Patent Application publication no. WO2011/084709, published Jul. 14, 2011, entitled "Methods and Apparatus for Conformal Sensing of Force and/or Change in Motion;" and U.S. Patent Application publication no. 2011 0034912-A1, published Feb. 10, 2011, filed Mar. 12, 2010, and entitled "SYSTEMS, METHODS, AND DEVICES HAVING STRETCHABLE INTEGRATED CIRCUITRY FOR SENSING AND DELIVERING THERAPY."

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

The foregoing and other aspects, examples, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 1A shows a block diagram of an example system for monitoring condition of a tissue, according to the principles herein.

FIG. 1B shows a block diagram of another example system for monitoring condition of a tissue, according to the principles herein.

DETAILED DESCRIPTION

Figure 2:
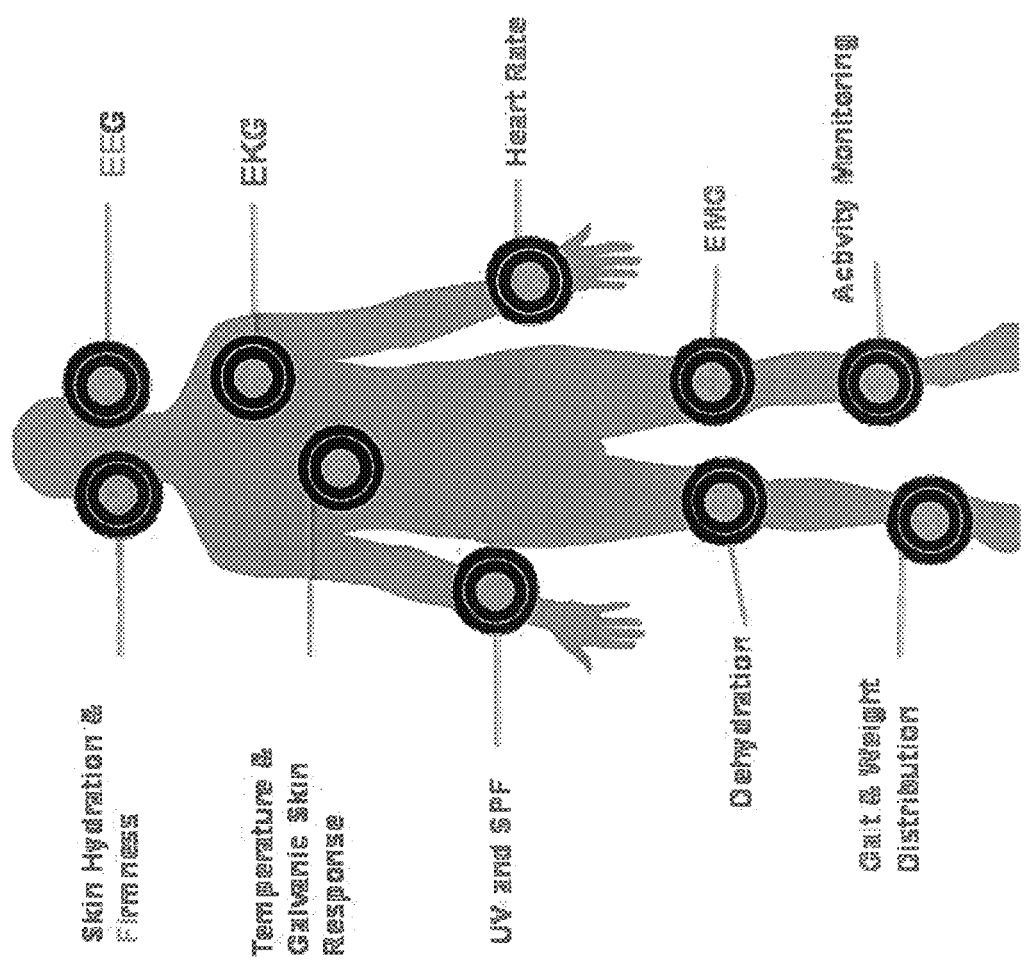
FIG. 2 shows examples of tissue conditions or tissue sections that may be monitored using the example apparatus, according to the principles herein.

Following below are more detailed descriptions of various concepts related to, and examples of, methods and apparatus for measuring electrical properties of tissue. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but not limited to, the term "including" means including but not limited to. The term "based on" means based at least in part on.

The apparatus and systems described herein provide technology platforms that use ultra-thin components linked with stretchable interconnects and embedded in low modulus polymers which provide a match to biological tissue. The technology platform implements high-performance active components in new mechanical form factors.

In non-limiting example, the technology platforms according to the principles described herein can be fabricated based on foundry complimentary metal-oxide-semiconductor (CMOS) wafers and transferred to polymer-based and/or polymer-coated carriers.

The technology platforms according to the principles herein provide apparatus and systems for on-body and in-body applications. As a non-limiting example, any of the example apparatus or systems described herein can be mounted directly to tissue. For example, the apparatus or system can be skin-mounted. In any example implementation described herein, an apparatus or system may be disposed on tissue for extended periods without discomfort, while facilitating continuous monitoring. For implementations inside the body, an apparatus or system described herein may be mounted to a catheter or other equivalent instrument which is disposed proximate to the tissue of a tissue lumen to provide electrical information about the tissue interior. For example, the tissue lumen can be but is not limited to the lumen of the heart.

As described in greater detail below, an apparatus or system according to the principles described herein can be implemented for measuring electrical properties of tissue. The apparatus or system can be configured to measure the electrical properties of the tissue through a capacitive-based measurement or through an inductance-based measurement. The measured electrical properties can be used as an indicator of the tissue condition. For example, the measurement of electrical properties can be used to monitor, e.g., the disease state of the tissue, mechanical properties of the tissue (including tissue firmness), the sweat level of the tissue (which can be related to its hydration level), or other condition of the tissue. Information from an ultrasound measurement also can be used to provide information about the disease state of the tissue, mechanical properties of the tissue (including tissue firmness), the sweat level of the tissue (which can be related to its hydration level), or other condition of the tissue.

An apparatus according to the principles described herein can be configured to measure electrical properties of the tissue through a capacitive-based measurement. An apparatus according to this example implementation can include at least two conductive structures disposed above the tissue. The capacitive-based measurement can be performed by applying a potential across the at least two conductive structures. The at least two conductive structures are disposed substantially parallel to each other. Each of the at least two conductive structures has a non-linear configuration (such as but not limited to a serpentine configuration, a zig-zag configuration, or a rippled configuration). The apparatus also includes at least two brace structures, each disposed substantially perpendicularly to the orientation of the at least two parallel conductive structures, and at least one spacer structure that is physically coupled at each of its ends to a portion of each of the at least two brace structures. Each of the at least two brace structures is in electrical communication with at least one of the at least two parallel conductive structures. The at least one spacer structure facilitates maintaining a substantially uniform separation between the at least two brace structures. A measure of the electrical property of the tissue using the apparatus is used to provide an indication of the condition of the tissue according to any of the principles described herein.

In another example implementation where the apparatus is configured to measure electrical properties of the tissue through a capacitive-based measurement, the apparatus can include at least two conductive structures that run substantially parallel to each other along substantially an entire length of the conductive structures. Each of the conductive structures can have a curved configuration. An apparatus according to this example implementation also can include at least two contact structures. Each of the at least two contact structures is in electrical communication with at least one of the at least two parallel conductive structures. The capacitive-based measurement can be performed by applying a potential across the at least two conductive structures using the at least two contact structures. A measure of the electrical property of the tissue using the apparatus is used to provide an indication of the condition of the tissue according to any of the principles described herein.

An apparatus according to the principles described herein can be configured to measure electrical properties of the tissue through an inductance-based measurement. An apparatus according to this example implementation can include a substrate disposed above the tissue, wherein the substrate is formed from a material that exhibits a change in a state with a change in tissue condition. As a non-limiting example, the substrate can be formed from a material that changes hydration state with a change in the sweat level of the tissue (which can be related to its hydration level). The apparatus further includes at least one first inductor structure disposed above the substrate. As non-limiting examples, the inductor structure can be a spiral coil structure, a cylindrical coil structure, or a toroidal structure. The inductance-based measurement can be performed by applying a signal to the at least one first inductor structure. An electrical property and/or a physical property of the at least one first inductor structure changes with the change in a\the state of the substrate. A measure of the electrical property or the physical property of the at least one first inductor structure using the apparatus is used to provide an indication of the tissue condition.

In an example implementation, any of the apparatus configured to measure electrical properties of the tissue through a capacitance-based or inductance-based measurement may be disposed directly above the tissue. In this example, the apparatus is used to measure an electrical property based on the condition of the tissue in the instant of measurement. A measurement according to this example can be used to provide an indication of a skin hydration level.

In another example implementation any of the apparatus configured to measure electrical properties of the tissue through a capacitance-based or inductance-based measurement may be disposed above the tissue with an absorbing layer positioned between the apparatus and the tissue. In this example, a measurement of a change in the state of the absorbing layer can be used to provide an indication of the condition of the tissue. For example, an absorbing layer that can absorb sweat may be disposed between the tissue and the example layer. In this example, the apparatus is used to measure an electrical property based on the amount of accumulated sweat in the absorbing layer. That is, each subsequent measurement of an electrical property is based on the higher amount of accumulated sweat over time in the absorbing layer. This measurement based on accumulated sweat can be related to the hydration level of the tissue. A measurement according to this example also can be used to provide an indication of a sweat rate (i.e., an amount of sweat gathered over an interval).

In an example, the potential applied to any of the apparatus described herein can be a time-varying potential. That is, any of the measurements performed herein, including a capacitance measurement or an inductance measurement, can be performed by changing the potential with time. The potential can be changed either periodically, or as a step function from one value of potential to another.

FIG. 1A shows a block diagram of a non-limiting example system according to the principles herein. The example system 100 includes at least one apparatus 102 that can be used to provide a measurement of the electrical properties of the tissue. The at least one apparatus 102 can be configured as describe herein to perform a capacitive-based measurement and/or an inductance-based measurement of the electrical properties of the tissue. The system 100 includes at least one other component 104 that is coupled to the at least one apparatus 102. In an example implementation, the at least one component 104 can be configured to supply the potential to the apparatus 102. For example, the at least one component 104 can include a battery or any other energy storage device that can be used to supply the potential. In an example implementation, the system 100 can include at least one component 104 for providing an indication of the tissue condition based on the measured electrical property of the tissue. In an example implementation, the at least one component 104 can include at least one processor unit configured for analyzing the signal from the apparatus based on the measurement of the electrical property of the tissue. In an example implementation, the at least one component 104 can be configured to transmit a signal from the apparatus based on the measurement of an electrical property of the tissue. For example, the at least one component 104 can include a transmitter or a transceiver configured to transmit a signal including data measured by the apparatus measurement from the apparatus to a hand-held device or other computing device. Non-limiting examples of a handheld device include a smartphone, a tablet, a slate, an e-reader, a digital assistant, or any other equivalent device. As a non-limiting example, the hand-held device or other computing device can include a processor unit that is configured for analyzing the signal from the apparatus based on the measurement of the electrical property of the tissue. The at least one other component 104 can be a temperature sensor.

FIG. 1B shows a block diagram of a non-limiting example system 150 according another implementation of the principles herein. The example system 150 includes at least one apparatus 102 that can be used to perform a measurement of the electrical properties of the tissue, including a capacitive-based measurement and/or an inductance-based measurement. In the non-limiting example of FIG. 1B, the at least one other component 104 includes an analog sensing block 152 that is coupled to the at least one apparatus 102 and at least one processor unit 154 that is coupled to the analog sensing block 152. The at least one other component 104 includes a memory 156. For example, the memory 156 can be a non-volatile memory. As a non-limiting example, the memory 156 can be mounted as a portion of a RFID chip. The at least one other component 104 also includes a transmitter or transceiver 158. The transmitter or transceiver 158 can be used to transmit data from the apparatus 102 to a handheld device or other computing device (e.g., for further analysis). The example system 150 of FIG. 1B also includes a battery 160 and a charge regulator 162 coupled to battery 160. The charge regulator 162 and battery 160 are coupled to the processor unit 154 and memory 156.

A non-limiting example use of system 150 is as follows. Battery 160 provides power for the apparatus 102 to perform the measurements. The processor unit 154 activates periodically, stimulates the analog sensing block 152, which conditions the signal and delivers it to an A/D port on the processor unit 154. The data from apparatus 102 is stored in memory 156. In an example, when a near-field communication (NFC)-enabled handheld device is brought into proximity with the system 150, data is transferred to the handheld device, where it is interpreted by application software of the handheld device. The data logging and data transfer can be asynchronous. For example, data logging can occur each minute while data transfer may occur episodically.

In a non-limiting example, a system according to the principles herein can be configured as a self-contained tissue-based system with power and wireless communication for monitoring the condition of the tissue (such as but not limited to monitoring the sweat level of the tissue (which can be related to its hydration level) and/or the disease of the tissue).

In a non-limiting example, the system 100 or system 150 can be mounted on a backing, such as but not limited to a patch. The backing is disposed over the tissue to be measured.

In a non-limited example, system 100, system 150 or any f the apparatus described herein may be covered at least in part by an excapsulation layer. The encapsulation layer can be formed from a polymer-based material, such as but not limited to a polyimide. In an example, the thickness of the encapsulation layer can be configured such that any of the systems or apparatus according to the principles herein lies at a neutral mechanical plane (NMP) or neutral mechanical surface (NMS) of the system or apparatus. The NMP or NMS lies at the position through the thickness of the device layers for the system or apparatus where any applied strains are minimized or substantially zero. The location of the NMP or NMS can be changed relative to the structure of the system or apparatus through introduction of materials that aid in strain isolation in the components of the system or apparatus that are used to perform the electrical measurements of the tissue. For example, the thickness of encapsulating material disposed over the system or apparatus described herein may be modified (i.e., decreased or increased) to depress the system or apparatus relative to the overall system or apparatus thickness, which can vary the position of the NMP or NMS relative to the system or apparatus. In another example, the type of encapsulating, including any differences in the elastic (Young's) modulus of the encapsulating material.

An apparatus or system according to the principles described herein can be used to monitor tissue condition in conjunction with a wide range of on-body sensors. Non-limiting examples of tissue conditions that may be measured using one or more of the apparatus described herein are shown in FIG. 2. For example, an apparatus or system herein can include at least one UV sensor configured for measuring an amount of UV exposure of the tissue. As another example, an apparatus herein can be configured to include at least one temperature sensor for measuring the temperature of the tissue.

The apparatus and systems of the technology platform described herein support conformal on-body electronics that can be used to log sensor data at very low power levels over extended periods, while providing wireless communication with external computing devices (including handheld devices).

For example, the technology platform described herein support conformal on-body electronics that can be used to monitor sweat rate of the body (which can be related to its hydration level). The human autonomic nervous system provides relatively slow feedback about fluid loss. A hydration sensor that can provide real-time updates on fluid loss could allow athletes to extend their performance period while minimizing subsequent ill-effects and speeding recovery. In a non-limiting example, a system or apparatus described herein can be configured as a hydration sensor that records the hydration level of a substrate material that changes hydration state with change in hydration of the tissue. The substrate material can be a soft absorbing material that collects sweat from the skin, and transmits the data of measurement to an external computing device (including a handheld device).

Capacitance-Impedance-Based Measurements

In a non-limiting example, skin hydration can be one of the major physiological responses for evaluation of dermatology, effectiveness of medical therapies, and cosmetology. The amount of sweat generated can provide an indication of a person's change in overall hydration level. It also can be used to provide an indication of a person's overall hydration level.

Sweat is brought to the surface of the skin by pores formed as channels that go through the skin from deeper levels. Sweating can be affected over a matter of minutes by, e.g., heat/cold or exercise/rest. Skin hydration is the water content inside the top layer of skin (the stratum corneum), and can changes over a period of days to weeks depending on, e.g., the overall body hydration, or skin treatment.

The skin hydration level can be determined by direct electrical measurements of impedance-capacitance (RC measurement), or by indirect measurements of the skin's mechanical and optical properties. Among these methods, RC measurements can be more reliable, easier to implement, and low cost. To perform a RC measurements, a physical contact should be maintained between the measuring electrodes of the apparatus or system and the tissue. The accuracy of these measurements can be dependent on the contact force applied to maintain a physical contact between the measuring electrodes of the apparatus or system and the tissue. If a RC measurement is performed using a rigid, planar electrodes, contact force is applied to ensure that these electrodes remain in contact with the skin's curved, compliant surface. For example, existing hydration sensors with rigid, planar electrodes that use a RC measurement approach have built-in pressure sensing devices to address this issue. Additionally, existing hydration sensors with rigid, planar electrodes may be limited to instantaneous measurements due to the lack of a reservoir for sweat storage. As a result, hydration sensors with rigid, planar electrodes can be difficult to use and may not provide continuous monitoring.

In a non-limiting example, the apparatus and systems described herein provide a new platform for collecting electrophysiological measurements of tissue. The technology described herein enables the electronics to be integrated on the tissue without requiring external mechanical loading to maintain contact. Novel epidermal skin sweat sensor composed of stretchable electrodes is described. Taking advantage of small conductive structures feature size and a discrete open-mesh-type structure, the apparatus described herein can be conformally applied on the tissue surface. In an example implementation, to achieve continuous monitoring capability, a cellulose pad can be mounted between the conductive structures and the tissue to serve as a sweat storage layer, and the entire structure is held together by an adhesive backing layer (such as but not limited to TEGA-DERM® (3M, St. Paul, Minn.). This backing layer provides structural support and holds the apparatus in tight contact with the tissue during measurements. With this configuration, the skin sweat sensor apparatus described herein provides a viable solution for reliable and continuous sweat monitoring.

A system, apparatus and method described herein facilitates measurement of capacitance-based properties of the tissue. The capacitance-based properties of the tissue can be used to provide an indication of the tissue condition. As a non-limiting example, a system, apparatus and method described herein can facilitate measurement of the sweat rate of the tissue (which can be related to a level of hydration and/or de-hydration of the tissue). In this example, measurement of capacitance-based electrical properties can be used to provide an indication of the level of hydration and/or de-hydration of tissue.

Figure 3:
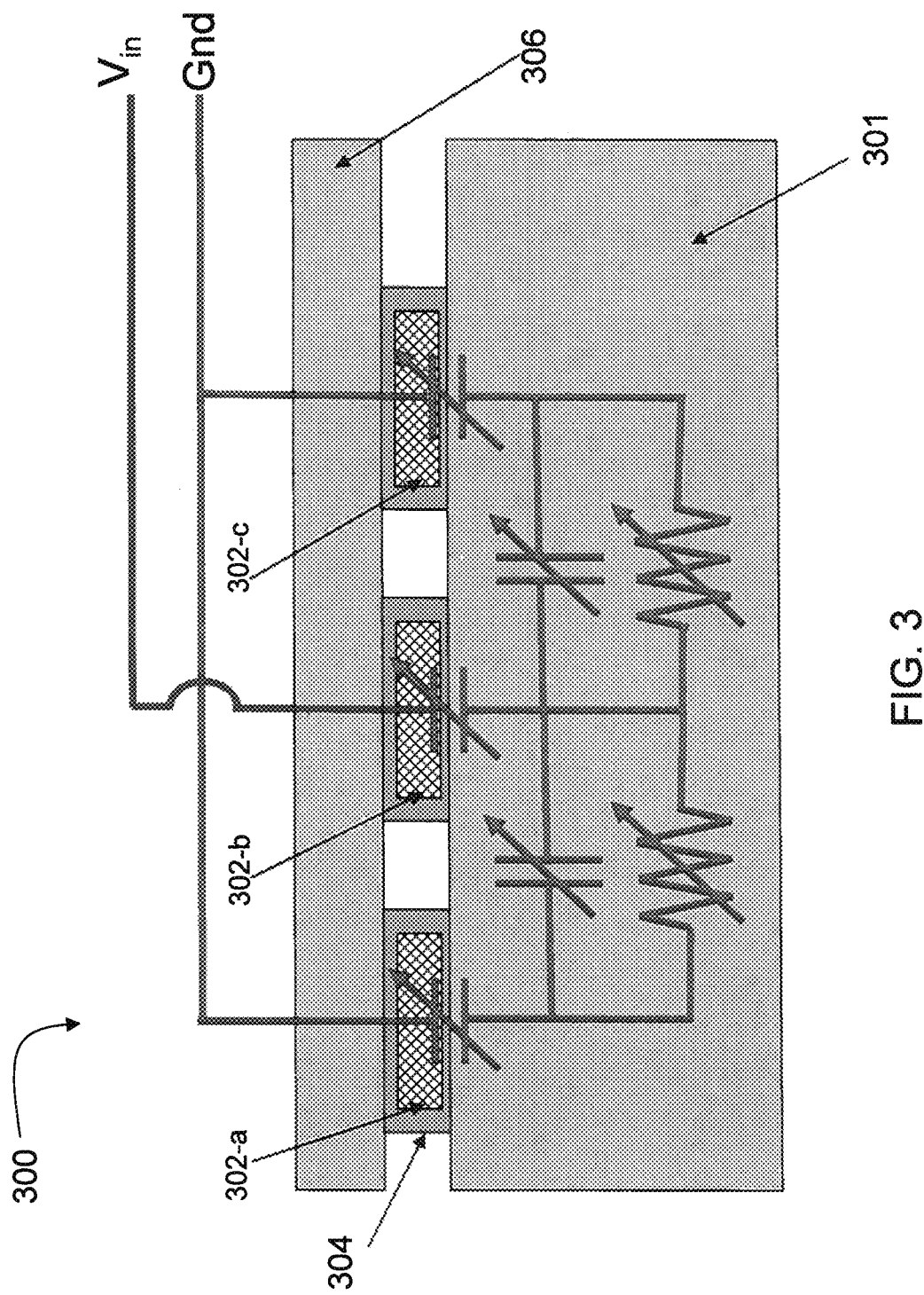
FIG. 3 shows a cross-section view of an example apparatus for monitoring condition of a tissue, according to the principles herein.

FIG. 3 shows a cross-section view of an example apparatus 300 according to an example implementation that includes three conductive structures 302-$a$, 302-$b$ and 302-$c$ disposed over a substrate 301. Substrate 301 can be skin or any other tissue. The example apparatus 300 also includes a layer 306. Layer 306 can include an adhesive portion that adheres to a portion of the substrate 301 to assist in maintaining conductive structures 302-$a$, 302-$b$ and 302-$c$ in contact with the substrate 301.

The illustration of FIG. 3 also shows an example electrical schematic of an effective circuit representation of the electrical properties of the substrate when the three conductive structures 302-$a$, 302-$b$ and 302-$c$ are disposed over the substrate 301. As illustrated in FIG. 3, when a potential (Vin) relative to ground (Gnd) is applied across neighboring pairs of conductive structures 302-$a$, 302-$b$ and 302-$c$, effective variable capacitance terms develop proximate to the interface between the conductive structures 302-$a$, 302-$b$ and 302-$c$ and the substrate 301, and effective variable capacitance and resistance term develop within the substrate 301. The effective circuit terms can be represent electrical properties of the apparatus and the tissue as follows:

$$R = \rho l / A \quad (1)$$

where R is the electrical resistance, $\rho$ is the resistivity, $l$ is the length in the tissue between the conductive structures, and AR is the cross-sectional area of current path through the tissue.

$$C = \in A / d \quad (2)$$

where C is the electrical capacitance, $\in$ is the permittivity, A is the overlapping area between the conductive structures and the tissue, and d is the separation distance between the conductive structures. In an example, the measurement of the electrical property of the substrate, such as but not limited to the tissue, among the three conductive structures 302-$a$, 302-$b$ and 302-$c$ can be modeled based on the example circuit elements of FIG. 3 and using the expressions of equations (1) and (2).

Figure 4:
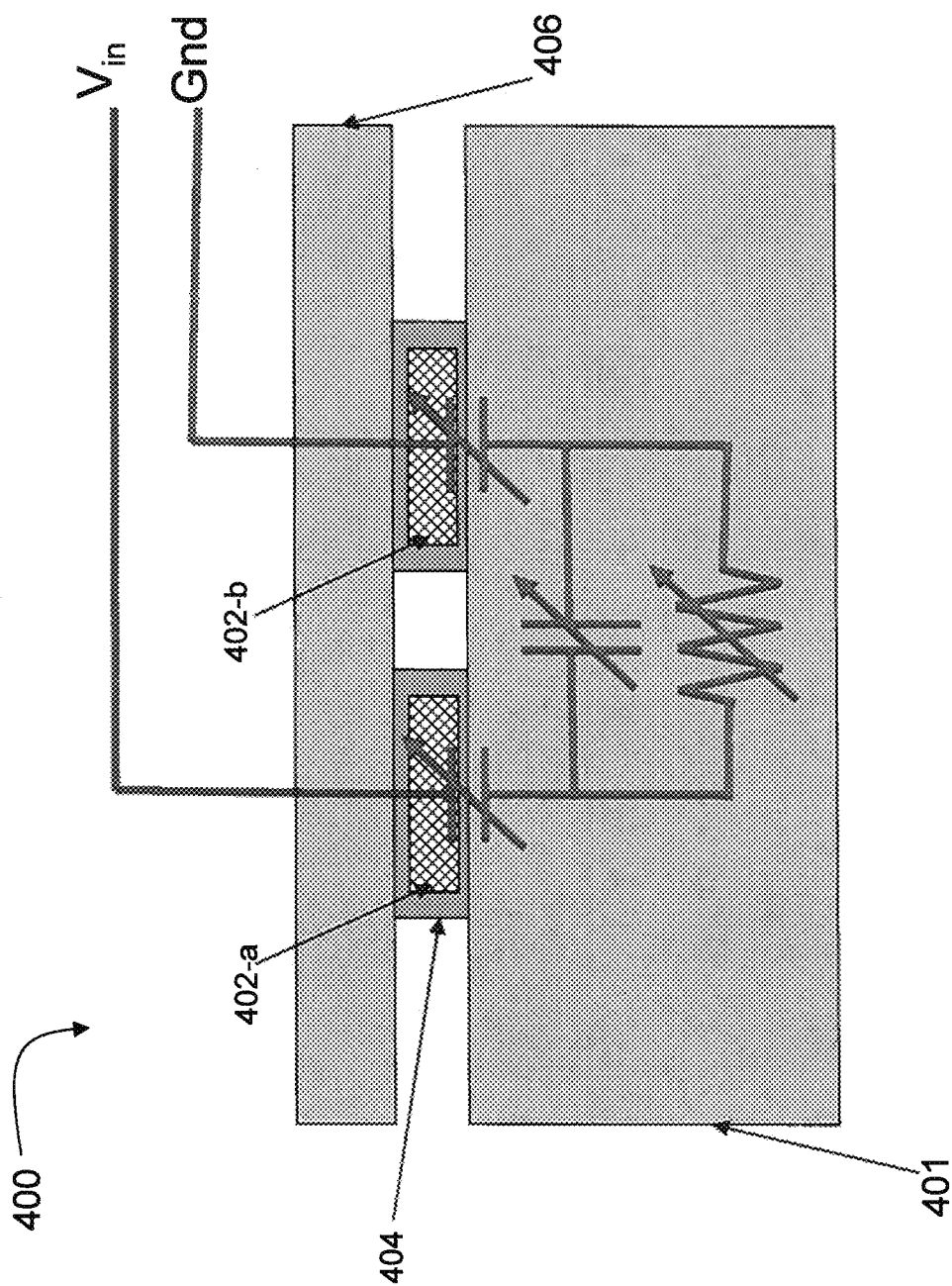
FIG. 4 shows a cross-section view of another example apparatus for monitoring condition of a tissue, according to the principles herein.

An apparatus or system according to the principles herein for performing capacitance-based measurements is not limited to solely three conductive structures. For example, an example apparatus or system can include 2, 5, 8, 10, 15 or more conductive structures (E1, E2 and E3, . . . , E(n), where n is an integer). For such a system, the effective circuit model of FIG. 3 can be extended to any number of effective circuit elements, with effective capacitance terms (C1, C2, C3, . . . , C(j), where j is an integer), and effective resistance terms (R1, R2, . . . , R(k), where k is an integer). FIG. 4 shows a cross-section view of another example apparatus 400 according to an example implementation that includes two conductive structures 402-$a$, 402-$b$ and 402-$c$ disposed over a substrate 401 (i.e., n=2). Substrate 401 can be skin or any other tissue. The example apparatus 400 also includes a layer 406. In an example, the measurement of the electrical property of the substrate 301 or 401 among the neighboring conductive structures, or conductive structures in close proximity, of the apparatus can be modeled based on the example circuit elements of FIG. 3 or FIG. 4, and extrapolated to model more components. The apparatus can be configured with any number n of conductive structures. Increasing the number n of conductive structures may provide for increased accuracy of the measured capacitance across the system inputs and outputs.

The conductive structures Ei (i=1, . . . 3) can include any applicable conductive material in the art, including a metal or metal alloy, a doped semiconductor, or a conductive oxide, or any combination thereof. Non-limiting examples of metals include Al or a transition metal (including Au, Ag, Cr, Cu, Fe, Ir, Mo, Nb, Pd, Pt, Rh, Ta, Ti, V, W or Zn), or any combination thereof. Non-limiting examples of doped semiconductors include any conductive form of Si, Ge, or a Group III-IV semiconductor (including GaAs, InP).

One or more of the conductive structures may be covered on at least one side by a polymer-based material, such as but not limited to a polyimide. In an example, one or more of the conductive structures may be encased in the polymer-based material. The polymer-based material can serve as an encapsulant layer.

Layer 306 or 406 may be a protective, encapsulating and/or backing layer made of a stretchable and/or flexible material. Non-limiting examples of materials that can be used for layer 306 or 406 include any applicable polymer-based materials, such as but not limited to a polyimide or a transparent medical dressing, e.g., TEGADERM® (3M, St. Paul, Minn.).

In a non-limiting example, layer 306 or 406 may be an encapsulation layer that is disposed over at least a portion of the at least two conductive structures. In an example, the encapsulation layer can be a polymer. In another example, portions of the encapsulation layer can include an adhesive, and wherein the adhesive maintains the portions of the encapsulation layer in physical contact with the tissue (including attaching it to the tissue). In this manner, the apparatus can be maintained in contact with the tissue.

In another example, an electrically conductive gel can be disposed between the apparatus and any absorbing layer present between the apparatus and the tissue. The conductive gel can deform easily and allow the spacing to change, but maintain the electrical distance between the apparatus and the absorber at substantially zero.

Substrate 301 or 401 may be a portion of tissue, such as but not limited to the skin, a muscle tissue, heart tissue, etc.

Figure 5:
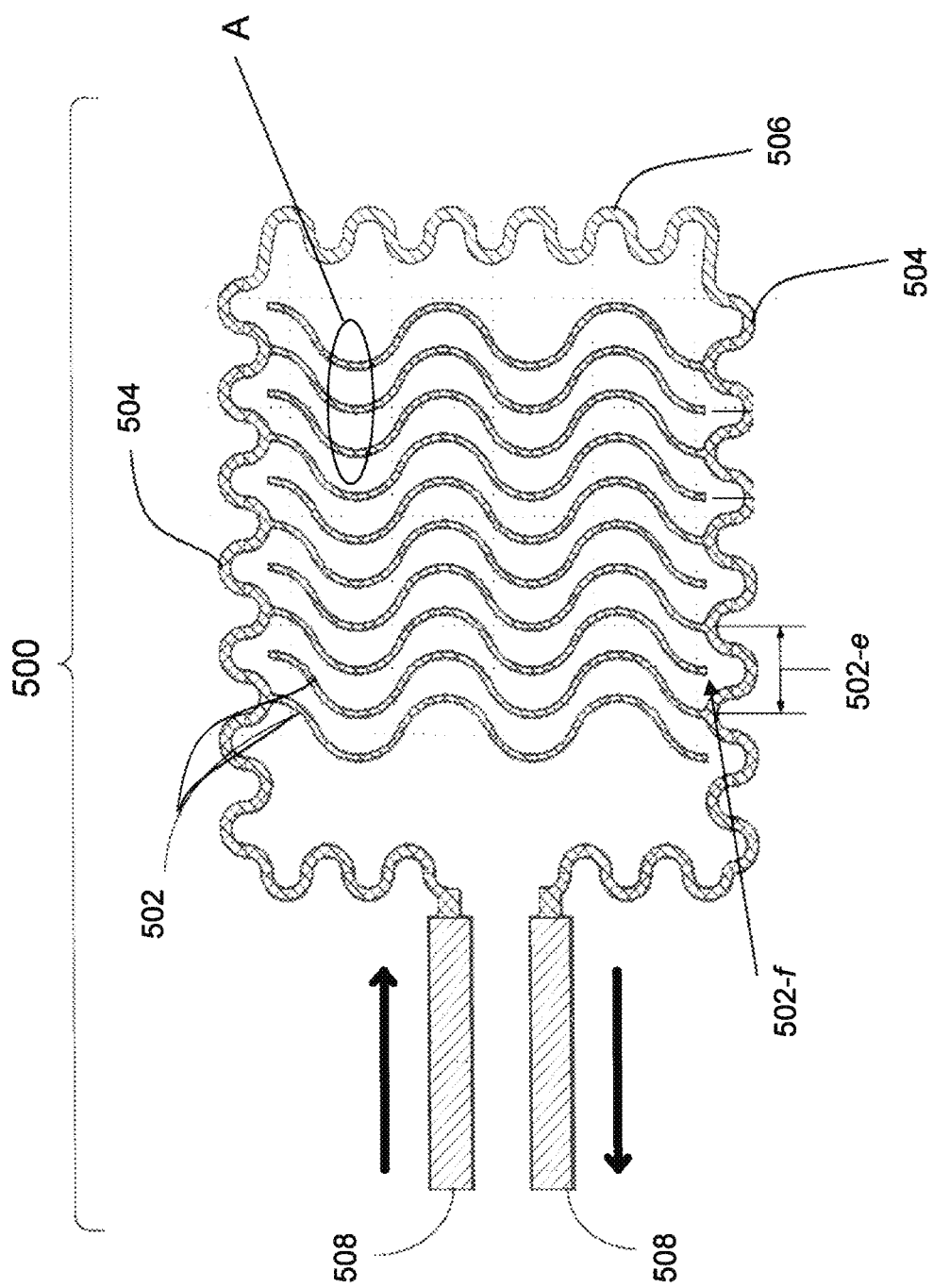
FIG. 5 shows an example apparatus that includes interdigitated conductive structures, according to the principles herein.

FIG. 5 shows an example apparatus 500 that includes ten (10) interdigitated conductive structures 502. The example apparatus 500 can be disposed over the tissue to perform the electrical measurements according to the principles described herein. The capacitance-based measurement can be performed by applying a potential across the interdigitated conductive structures. In the example of FIG. 5, the interdigitated conductive structures 502 are disposed substantially parallel to each other. Each of the interdigitated conductive structures 502 has a non-linear configuration. In the example of FIG. 5, the conductive structures 502 have a serpentine configuration. In other examples, non-linear configuration of the conductive structures 502 can be a, a zig-zag configuration, a rippled configuration, or any other non-linear configuration. The non-linear configuration of the conductive structures can facilitate greater sampling of the electrical properties of the tissue and higher signal to noise than linear electrodes. The non-linear configuration of the conductive structures also facilitates more consistent performance of the apparatus with deformation such as stretching. The example apparatus 500 also includes two brace structures 504, each disposed substantially perpendicularly to the overall orientation of the interdigitated conductive structures 502, and at least one spacer structure 506 that is physically coupled at each of its ends to a portion of each of the at least two brace structures. Each of the brace structures 504 is in electrical communication with alternating ones of the conductive structures 502. For example, conductive structures 502-e are in electrical communication with one of the brace structure 504 while the alternating, interposed conductive structure 502-f is not in electrical communication with that brace structure 504. The spacer structure 506 facilitates maintaining a substantially uniform separation between the brace structures 504. The spacer structure 506 can also facilitates maintaining a substantially uniform form factor during deformation of the apparatus. A measure of the electrical property of tissue using the example apparatus 500 can be used to provide an indication of the condition of the tissue according to any of the principles described herein.

The example apparatus 500 may also include contacts 508 that provides for electrical communication between the apparatus 500 and at least one other component, as described hereinabove and in connection with FIG. 1A or 1B. For example, the at least one other component can be a battery that applies a potential across the contacts 508, and in turn across neighboring conductive structures 502. in an example, a system is provided according to the principles described herein that includes apparatus 500 and at least one other component (as described herein above).

The conductive structures and the brace structures can include any applicable conductive material in the art, including a metal or metal alloy, a doped semiconductor, or a conductive oxide, or any combination thereof. Non-limiting examples of metals include Al or a transition metal (including Au, Ag, Cr, Cu, Fe, Ir, Mo, Nb, Pd, Pt, Rh, Ta, Ti, V, W or Zn), or any combination thereof. Non-limiting examples of doped semiconductors include any conductive form of Si, Ge, or a Group III-IV semiconductor (including GaAs, InP). In an example, the conductive structures and the brace structures can be formed from the same conductive material. In another example, the conductive structures and the brace structures can be formed from different conductive materials.

The conductive structures and/or the brace structures may be covered on at least one side by a polymer-based material, such as but not limited to a polyimide. In an example, the conductive structures and/or the brace structures may be encased in the polymer-based material. The polymer-based material can serve as an encapsulant layer.

Spacer structure also may be formed from a polymer-based material.

Apparatus 500 or a system that includes apparatus 500 may include a protective and/or backing layer made of a stretchable and/or flexible material. Non-limiting examples of materials that can be used for the protective and/or backing layer include any applicable polymer-based materials, such as but not limited to a polyimide or a transparent medical dressing, e.g., TEGADERM® (3M, St. Paul, Minn.). The protective and/or backing layer can include an adhesive portion that adheres to a portion of the substrate to assist in maintaining the conductive structures 502 in contact with the substrate (including the tissue).

In a non-limiting example, the dimensions and morphology of the sensing component can be maintained using the spacer structure 506. In an example, the spacer structure 506 is formed from an insulating material or another material with lower conductivity than the conductive structures or the brace structures. The properties of the spacer structure 506 of the apparatus 500 can facilitate little or no current directly passing from one brace structure to the other brace structure by way of the spacer structure 506. Rather, current passes from one set of the conductive structures 502 to another set of the conductive structures 502 by way of the underlying tissue.

In an example according to FIG. 5, the length of the ripples of the brace structure may be uniform or may vary from one side of the apparatus 500 relative to the other.

In a non-limiting example, the non-linear configuration of the conductive structures facilitates increased flexibility of the apparatus. For example, the non-linear geometry can facilitate increased flexibility of the apparatus to stretching, torsion or other deformation of the underlying tissue, and the apparatus maintains substantial contact with the tissue in spite of the stretching, torsion or other deformation.

Figure 6:
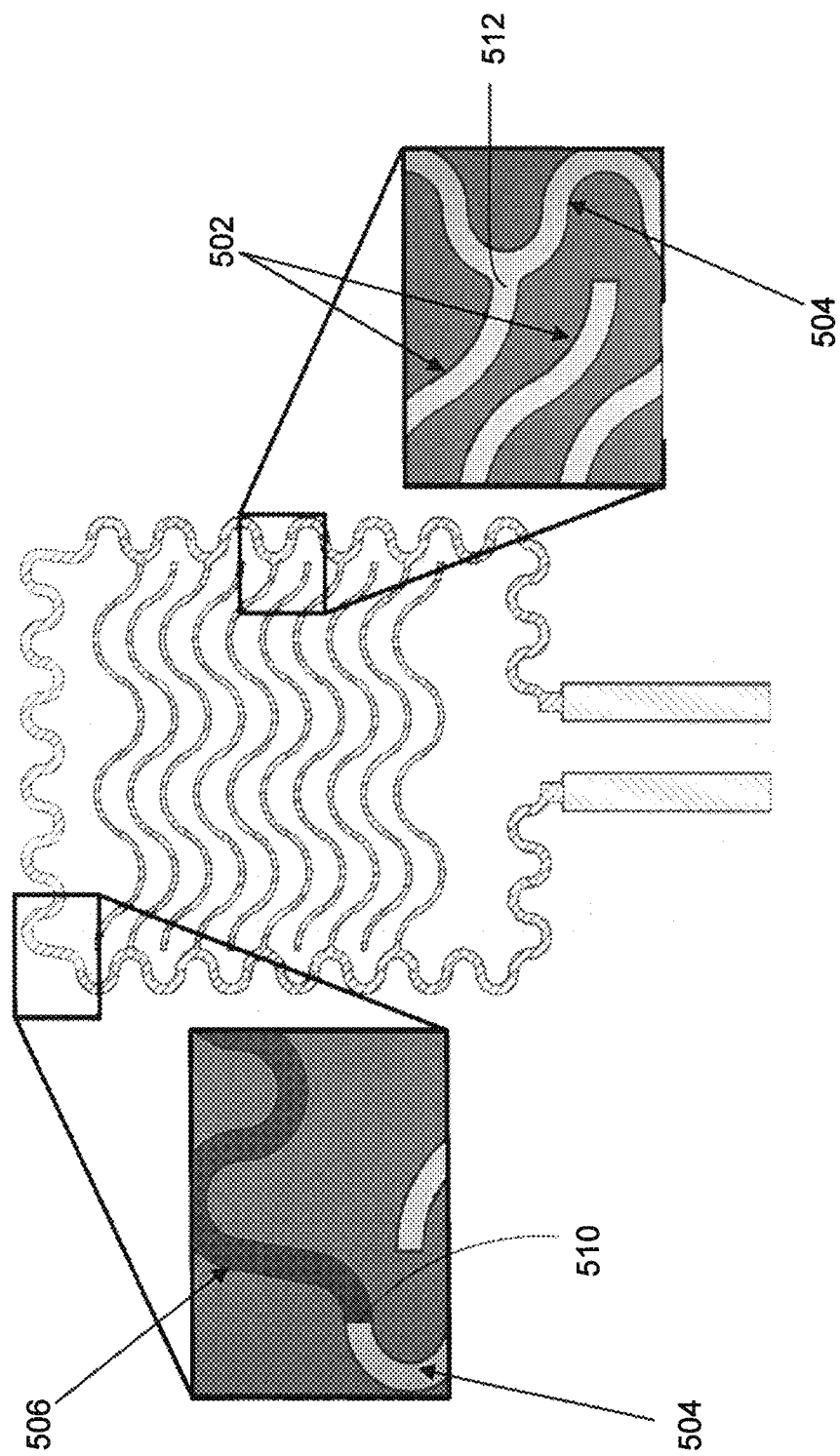
FIG. 6 is an illustration of the example apparatus of FIG. 5, with selected portions magnified, according to the principles herein.

FIG. 6 is an illustration of the example apparatus 500 of FIG. 5, with selected portions magnified. FIG. 6 shows a magnification of a portion of the apparatus 500 where a side of the brace structure 504 (lighter colored segment) forms an interface 510 with the spacer structure 506. FIG. 6 shows a magnification of an interface 512 between a brace structure 504 and a conductive structure 502, which also shows that alternating ones of the interdigitated conductive structure 502 makes physical contact with the brace structure 504.

Figure 7:
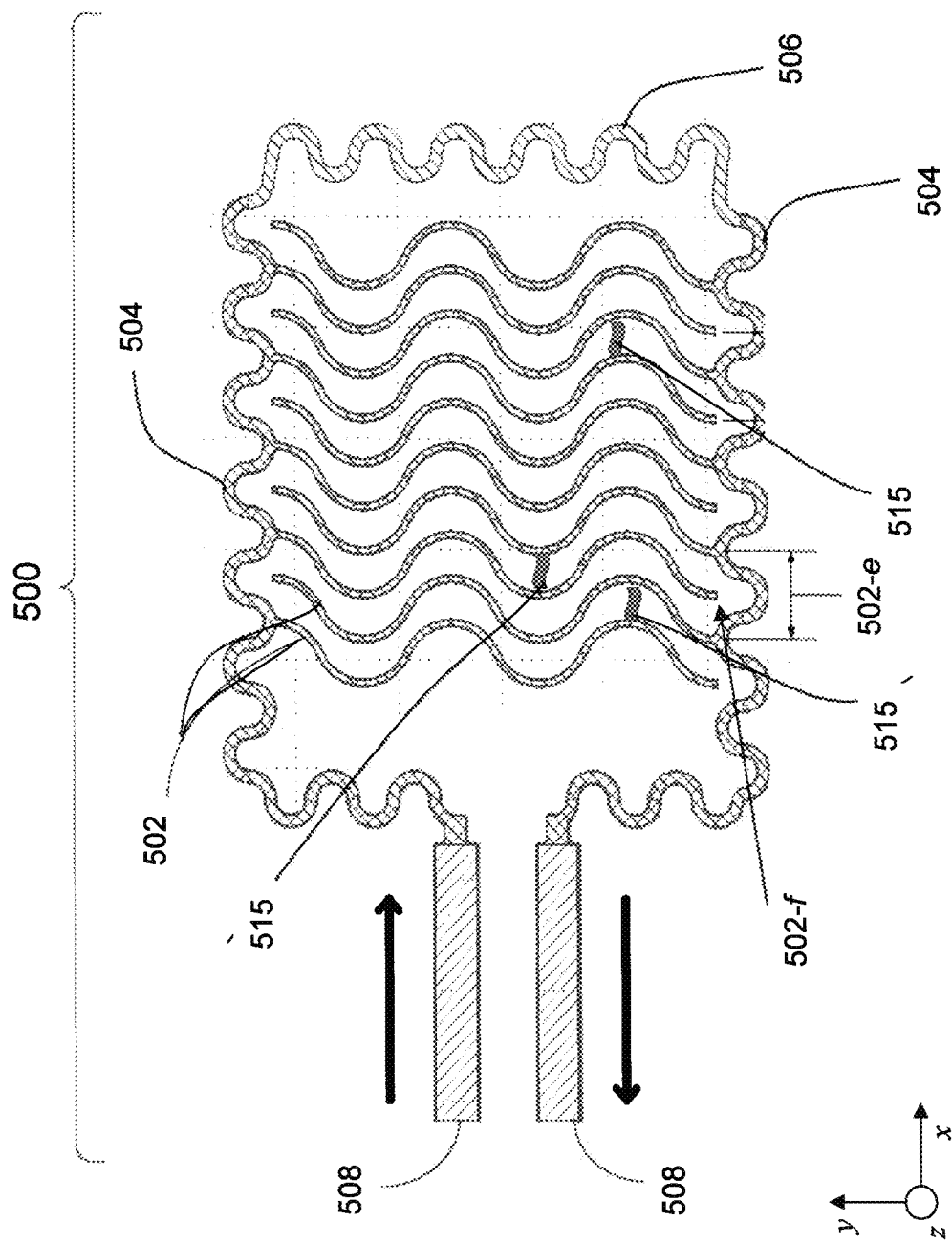
FIG. 7 shows an example of an apparatus with cross-link structures disposed between interdigitated conductive structures, according to the principles herein.

FIG. 7 shows a non-limiting examples of the apparatus 500 including cross-link structures 515 that can be formed according to the principles herein. The cross-link structures 515 can provide increased mechanical stability of the structure during fabrication (e.g., during a transfer process from a substrate and/or a printing and extraction process to another substrate), and in use, e.g., to stabilize the sensor against stretching, flexing, torsion or other deformation of the substrate it is disposed on. For example, the cross-link structures 515 can aid in maintaining a form factor, including ratios of dimensions, during and/or after a stretching, elongation or relaxing of the apparatus. For example, the cross-link structures 515 can be formed across any pair of the conductive structures 502 of FIG. 5, at any position along their length. In the examples shown, the cross-links structures 515 are formed in a serpentine ("S") shape. In other examples, the cross-link structures 515 can be formed as substantially straight crossbars, formed in a zig-zag pattern, formed as arcs, or ripples, or any other morphology that facilitates maintaining a mechanical stability and/or a form factor of the apparatus. In addition, the cross-link structures 515 can be formed as at least two cross-link structures that are formed across neighboring electrodes.

The cross-link structures 515 can be formed from a polymer-based material or any other stretchable and/or flexible material. In addition, while the positioning of the example cross-link structures 515 are shown to be roughly aligned in the x-direction of the FIG. 7, cross-link structures 515 also can be displaced relative to each other in the x-direction.

In the example of FIG. 7, the cross-link structures 515 can be formed of substantially the same encapsulant material that covers portions of the interdigitated conductive structures, and extend seamlessly from them. In this example, these cross-link structures 515 can be formed during the same process step that disposes the encapsulant polymer-based material on portions of the interdigitated conductive structures. In another examples, the cross-link structures 515 can be formed of a different material from the encapsulant material that covers portions of the interdigitated conductive structures.

Figure 9:
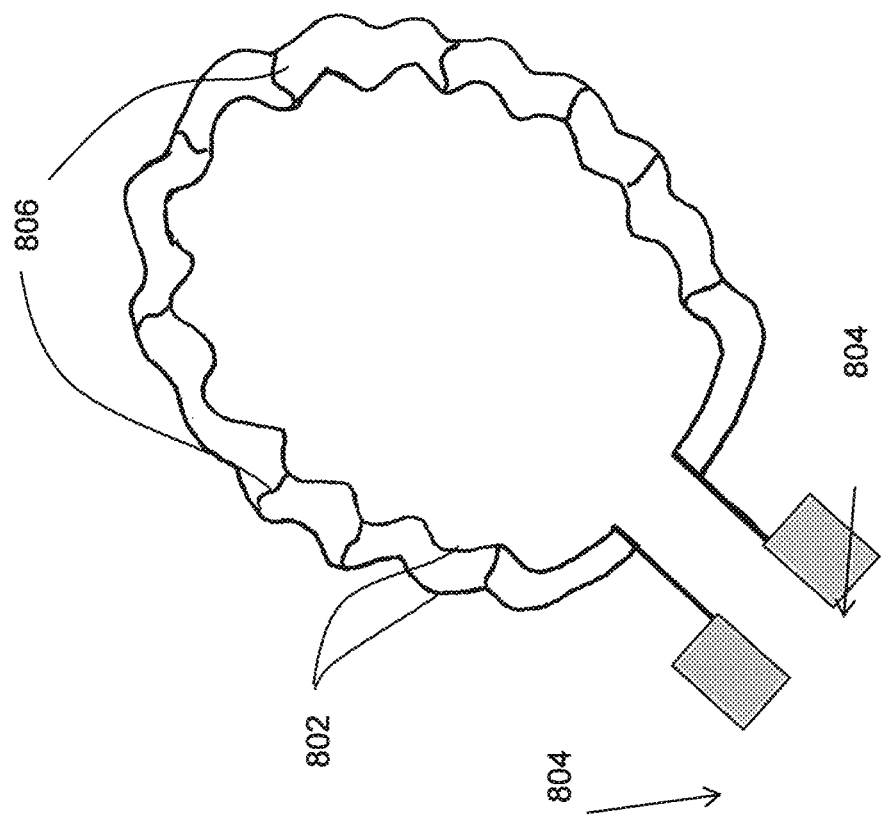
FIG. 9 shows another example apparatus with curved conductive structures and cross-link structures, according to the principles herein.
Figure 8:
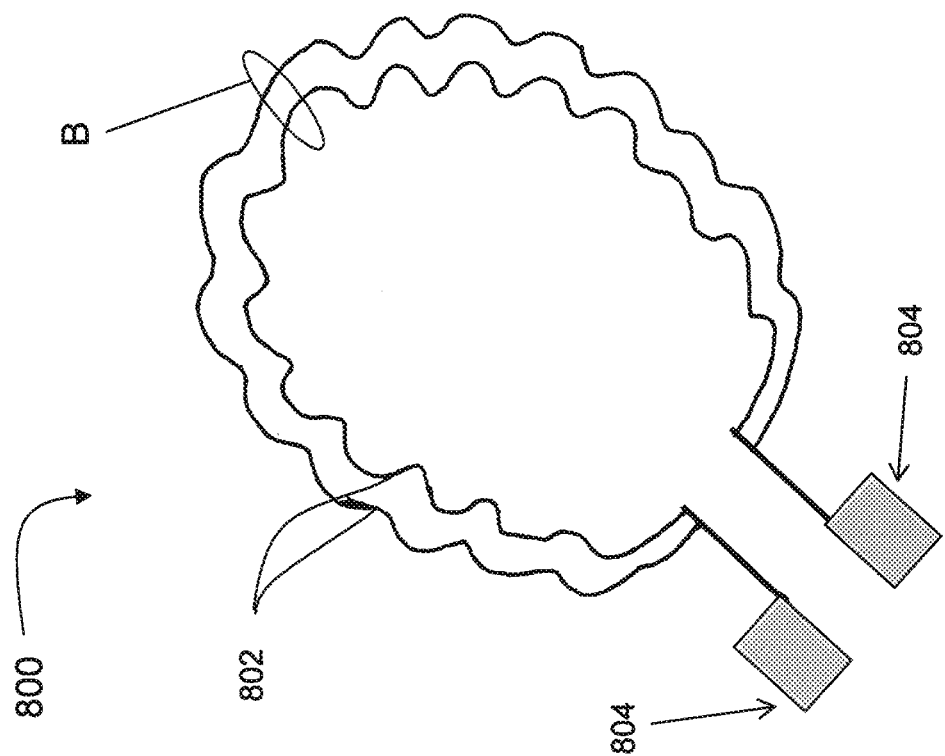
FIG. 8 shows an example apparatus with curved conductive structures, according to the principles herein.
Figure 10:
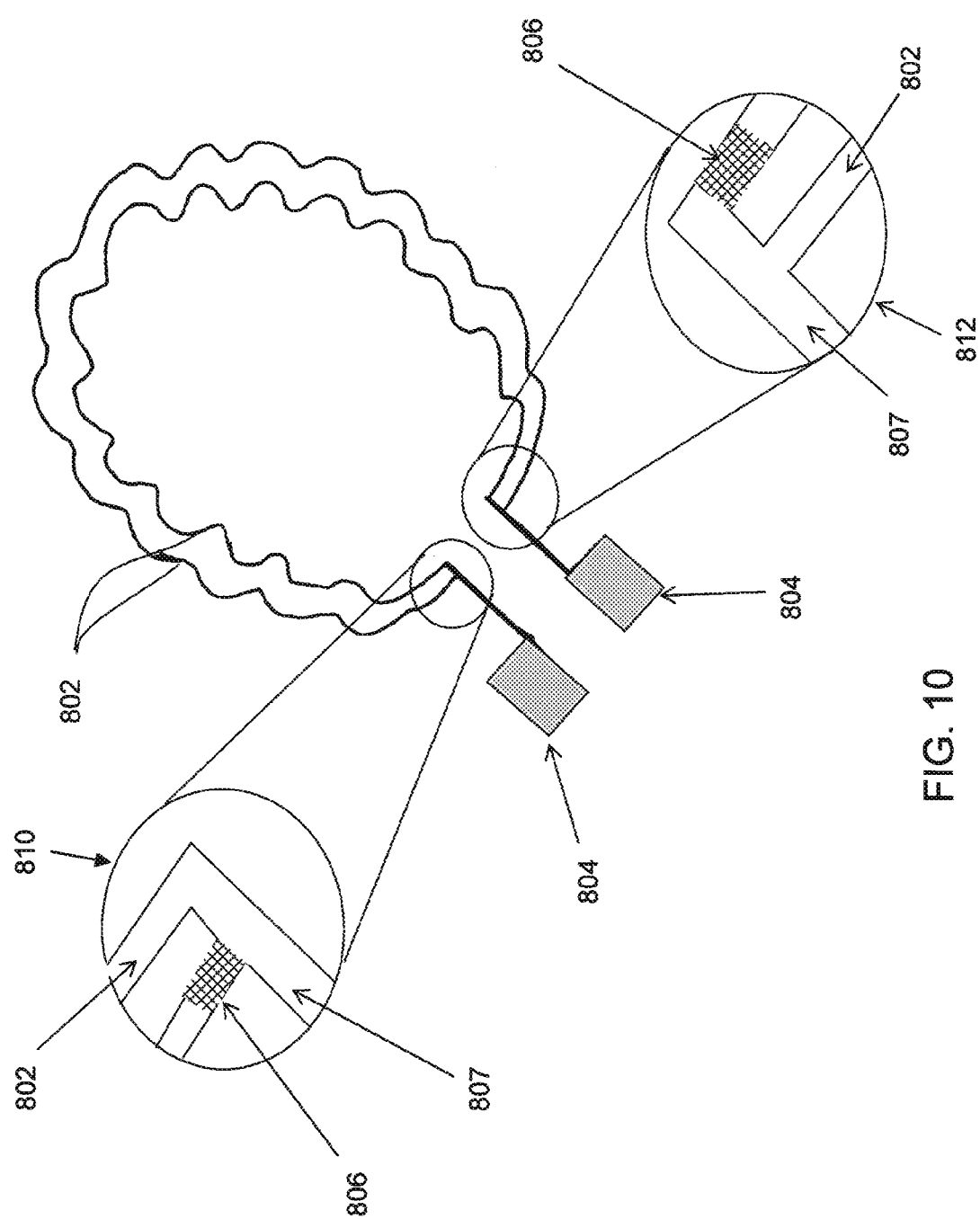
FIG. 10 shows another example with curved conductive structures, according to the principles herein.

FIGS. 8 through 10 illustrate another example implementation of an apparatus that is configured to measure electrical properties of the tissue through a capacitance-based measurement. As shown in FIG. 8, the apparatus 800 can include at least two conductive structures 802 that run substantially parallel to each other along substantially an entire length of the conductive structures 802. Each of the conductive structures 802 can have a curved configuration. Apparatus 800 according to this example implementation also can include at least two contact structures 804. Each of the at least two contact structures 804 is in electrical communication with at least one of the at least two parallel conductive structures 802. The capacitive-based measurement can be performed by applying a potential across the at least two conductive structures 802 using the at least two contact structures 804. A measure of the electrical property of the tissue using the apparatus 800 is used to provide an indication of the condition of the tissue according to any of the principles described herein.

While the examples of FIG. 8 through 10 are illustrated with two curved conductive structures 802, other examples according to the principles herein can include three, four or more curved conductive structures 802 that are disposed substantially concentrically and are in electrical communication with contacts 804.

The conductive structures 802 and the contact structures 804 can include any applicable conductive material in the art, including a metal or metal alloy, a doped semiconductor, or a conductive oxide, or any combination thereof. Non-limiting examples of metals include Al or a transition metal (including Au, Ag, Cr, Cu, Fe, Ir, Mo, Nb, Pd, Pt, Rh, Ta, Ti, V, W or Zn), or any combination thereof. Non-limiting examples of doped semiconductors include any conductive form of Si, Ge, or a Group III-IV semiconductor (including GaAs, InP). In an example, the conductive structures 802 and the contact structures 804 can be formed from the same conductive material. In another example, the conductive structures 802 and the contact structures 804 can be formed from different conductive materials.

The conductive structures 802 and/or the contact structures 804 may be covered on at least one side by a polymer-based material, such as but not limited to a polyimide. In an example, the conductive structures 802 and/or the contact structures 804 may be encased in the polymer-based material. The polymer-based material can serve as an encapsulant layer.

Apparatus 800 or a system that includes apparatus 800 may include a protective and/or backing layer made of a stretchable and/or flexible material. Non-limiting examples of materials that can be used for the protective and/or backing layer include any applicable polymer-based materials, such as but not limited to a polyimide or a transparent medical dressing, e.g., TEGADERM® (3M, St. Paul, Minn.). The protective and/or backing layer can include an adhesive portion that adheres to a portion of the substrate to assist in maintaining the conductive structures 802 in contact with the substrate (including the tissue).

As shown in FIG. 9, the apparatus may include cross-link structures 815. The cross-link structures 815 can provide increased mechanical stability of the structure during fabrication (e.g., during a transfer process from a substrate and/or a printing and extraction process to another substrate), and in use, e.g., to stabilize the sensor against stretching, flexing, torsion or other deformation of the substrate it is disposed on. For example, the cross-link structures 815 can aid in maintaining a form factor, including ratios of dimensions, during and/or after a stretching, elongation or relaxing of the apparatus. For example, the cross-link structures 815 can be formed across any pair of the conductive structures 802 of FIG. 5, at any position along their length. In the examples shown, the cross-links structures 815 are formed in a serpentine ("S") shape. In other examples, the cross-link structures 815 can be formed as substantially straight crossbars, formed in a zig-zag pattern, formed as arcs, or ripples, or any other morphology that facilitates maintaining a mechanical stability and/or a form factor of the apparatus. In addition, the cross-link structures 815 can be formed as at least two cross-link structures that are formed across neighboring electrodes. The cross-link structures 815 can be formed from a polymer-based material or any other stretchable and/or flexible material.

In the example of FIG. 9, the cross-link structures 815 can be formed of substantially the same encapsulant material that covers portions of the conductive structures, and extend seamlessly from them. In this example, these cross-link structures 815 can be formed during the same process step that disposes the encapsulant polymer-based material on portions of the conductive structures. In another examples, the cross-link structures 815 can be formed of a different material from the encapsulant material that covers portions of the conductive structures 815.

FIG. 10 shows magnifications 810 and 812 of the interface between the conductive structures 802 and leads 807. Leads 807 provide for electrical communication between conductive structures 802 and contacts 804. As shown in the magnifications 810 and 812 of FIG. 10, one of the conductive structures 802 is separated from lead 807 by a spacer structure 806. In an example, the spacer structure 806 is formed from an insulating material or another material with lower conductivity than the conductive structures 802 or the leads 807. The properties of the spacer structure 806 of the apparatus 800 can facilitate little or no current directly passing from one conductive structure 802 to the lead 807 by way of the spacer structure 806. Rather, current passes from one set of the conductive structures 802 to another set of the conductive structures 802 by way of the underlying tissue. Spacer structures 806 also may be formed from a polymer-based material.

Figure 11A:
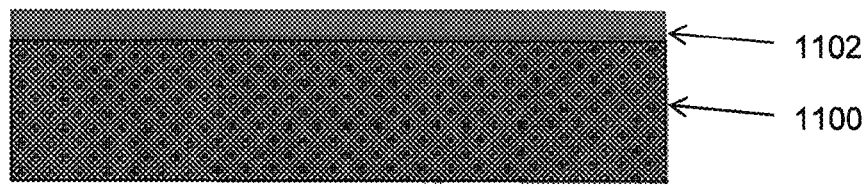
FIGS. 11A-11I show an example process for fabricating an example apparatus, according to the principles herein.
Figure 11B:
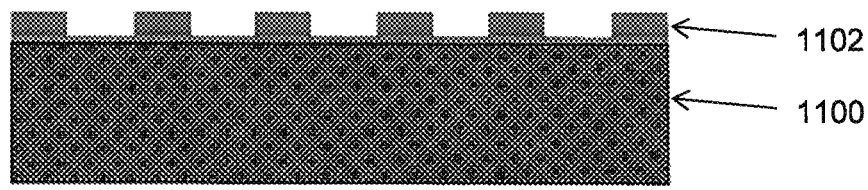
Figure 11C:
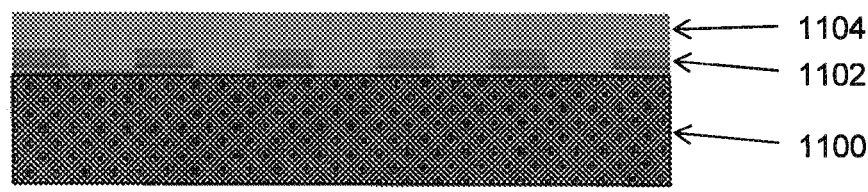
Figure 11D:
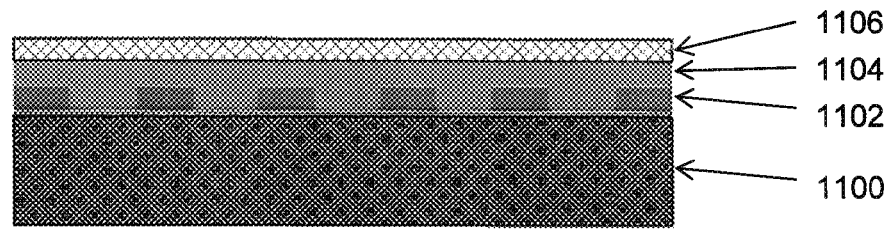
Figure 11E:
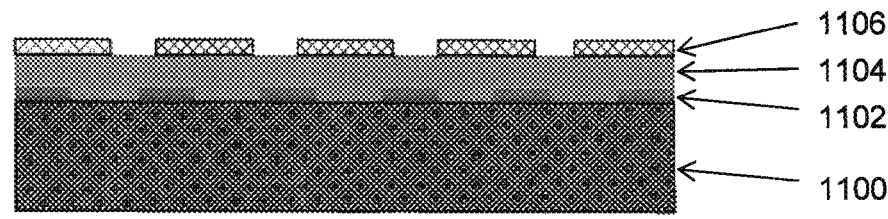
Figure 11F:
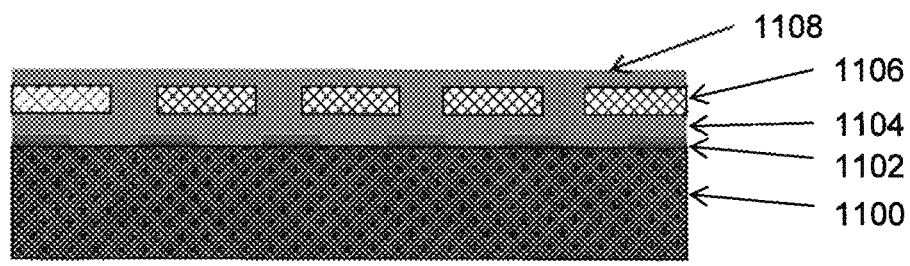
Figure 11G:
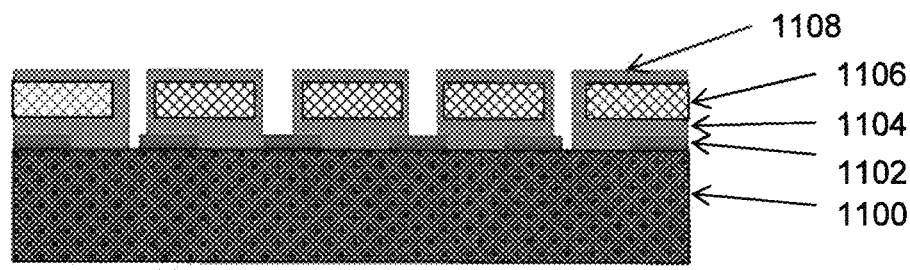
Figure 11H:
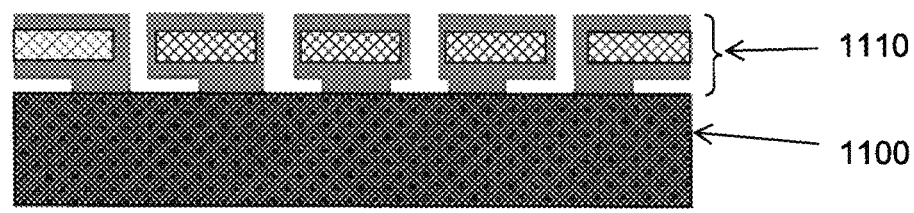
Figure 11:
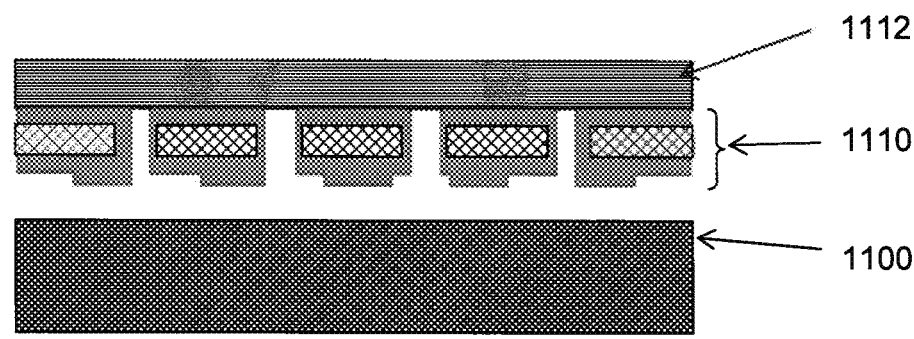

A non-limiting example process for fabricating the example apparatus of any of FIGS. 5 through 10 is illustrated in FIGS. 11A-11I. In FIG. 11A, a fabrication substrate 1100, such as but not limited to a silicon substrate or a substrate for group III-V electronics, is coated with a with a sacrificial release layer 1102. In a non-limiting example, the sacrificial release layer 1102 is a polymer such as polymethylmethacrylate (PMMA). In FIG. 11B, the sacrificial release layer 1102 is patterned. In FIG. 11C, a first polymer layer 1104 is spin coated onto the sacrificial release layer 1102. In an example, the first polymer layer 1104 can be a polyimide. In FIG. 11D, a layer of conductive material 1106 is deposited over the first polymer layer 1104 to form the conductive structures. In FIG. 11E, where applicable to the conductive material 1106 used, a lithography process may be performed to pattern the conductive material 1106 into any of the configurations of conductive structures described herein. In FIG. 11F, a second polymer layer 1108 is spin coated over the conductive structures. In an example, the second polymer layer 1108 can be a polyimide. In FIG. 11G, the second polymer layer 1108 is patterned. In FIG. 11H, the sacrificial release layer material is selectively removed. For example, where the sacrificial release layer material is PMMA, acetone can be used for selective removal. At this stage, the apparatus 1110 is in substantially final form and attached to the fabrication substrate. In FIG. 11I, a transfer substrate 1112 is used to remove the apparatus 1110 from the fabrication substrate 1100.

Figure 12A:
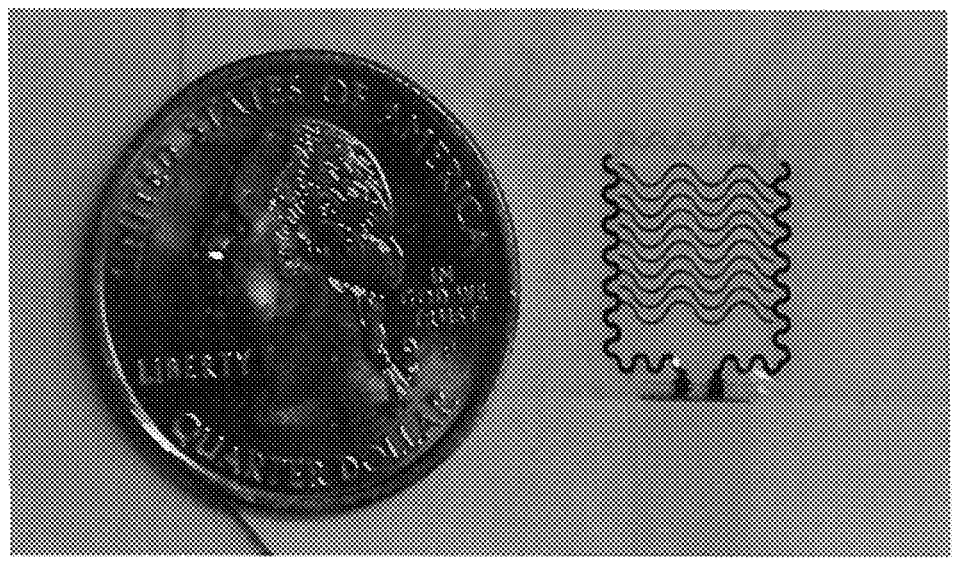
FIGS. 12A-12E show an example apparatus that includes the interdigitated conductive structures, according to the principles herein.
Figure 12B:
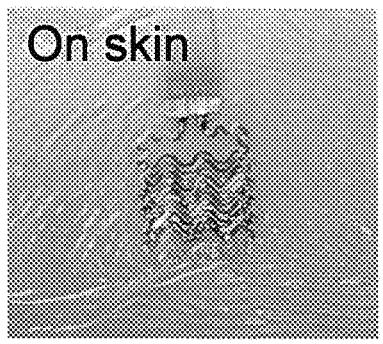
Figure 12C:
Figure 12D:
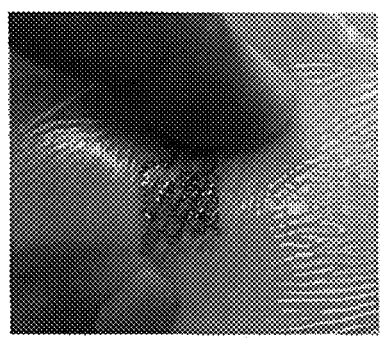
Figure 12E:
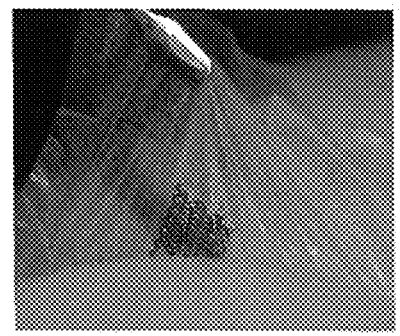

FIGS. 12A through 12E show an example implementation of an example apparatus that includes the interdigitated conductive structures. FIG. 12A shows that the example apparatus can be fabricated in dimensions comparable to a coin. The dimensions of the electrodes are 100 μm wide, and 0.5 μm thick. Due to the open-mesh electrode structure, the strain on the conductive structures due to tissue stretching can be limited. The turning angle [7] on the conductive structures is designed as −25 degree. In addition, the stretchable conductors interconnecting the conductive structures play a role during stretching. In this regard, the turning angle of the stretchable conductors is designed as 0 degree. In this example, both the electrodes and the stretchable conductors are made of gold (Au) and are fully encapsulated in polyimide (PI) for mechanical reliability. The polyimide is 10 μm thick on both top and bottom of the electrodes. FIG. 12B shows the example apparatus disposed on skin using a protective layer before a measurement is made. FIG. 12C shows the example apparatus under a length-wise stretching deformation. FIG. 12D shows the example apparatus under a diagonal stretching deformation. In each of these scenarios, the example apparatus is configured such that it returns to substantially its original form factor once the deformation force is removed. FIG. 12E shows the example apparatus being removed from the skin.

An example implementation of a measurement using an example apparatus or system described herein is as follows. The effective circuit terms model of an example apparatus or system described herein (such as but not limited to the effective circuits illustrated in FIGS. 3 and 4) can be used to model electrical measurements performed using the apparatus of FIGS. 5 through 7 or the apparatus of FIGS. 8 through 10. For example, the effective circuit described in connection with FIG. 3 can be used to model a measurement across a line through portion "A" of FIG. 5, or extrapolated to model the plurality of conductive structures of the entire interdigitated structure. As another example, the effective circuit described in connection with FIG. 4 can be used to model a measurement across a line through portion "B" of FIG. 8.

The analyzed electrical measurements made using an apparatus according to the principles described herein in connection with any of FIGS. 5 through 10 can be used to provide an indication of changes in the tissue condition. For example, the effective circuit terms near the interface in FIG. 3 or FIG. 4 are observed to be sensitive to changes in tissue condition, such as but not limited to the sweat rate of the underlying tissue (which can be related to its hydration level). Within the substrate, the variable capacitance and resistance terms develop between the conductive structures. These effective terms are observed to be sensitive to the sweat level of the tissue (which can be related to hydration levels) and/or stretching of the example apparatus or system and/or the underlying tissue.

An example method is provided herein for determining tissue condition based on the measurement of the electrical property of the substrate using a capacitance-based measurement. The method includes receiving data in connection with a measurement of the electrical properties of the tissue, and applying a model to the data to quantify at least one parameter of the effective circuit model. The value of the parameter can be used to provide an indication of the tissue condition.

In an example system, apparatus and method, any of the apparatus described hereinabove can be disposed on to perform the measurement of the electrical properties. In an example, the sensor is configured to withstand deformation in more than one direction (for example, in x, y and/or z-direction). In a non-limiting example system, apparatus and method herein, a fully conformal sensor that includes an apparatus described herein is provided. The fully conformal sensor can be placed on, including being attached on. a variety of surface profiles, with minimal to no effect on the functionality of the sensor to detect tissue conditions, such as but not limited to a sweat level (which can be related to a hydration level), a tissue disease state, or mechanical properties of the tissue.

As a non-limiting example, the value of the parameter can be compared and/or correlated to a calibration standard of tissue condition versus the value of the circuit parameter. The calibration standard can be generated based on a training set of electrical measurements of tissue, or material similar to tissue, that exhibits the condition that is sought to be characterized. For example, the training set can include tissue at various stages of a disease condition, where the correlation between the electrical measurements and the known disease stage can be used to generate the calibration standard applied to tissue of unknown disease state. As another example, the training set can include tissue at various hydration levels. The correlation between the electrical measurements and the known hydration levels can be used to generate the calibration standard applied to tissue of unknown hydration level.

Figure 13A:
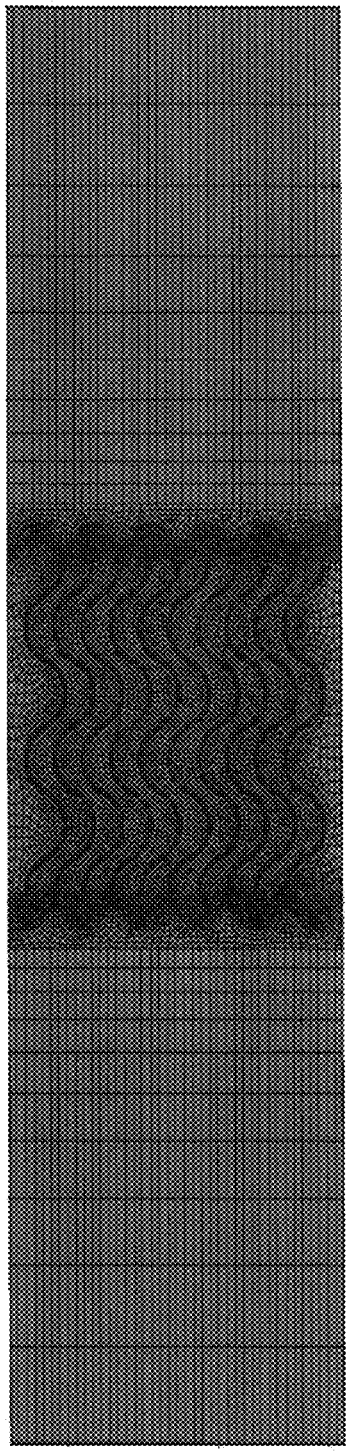
FIG. 13A shows a finite element (FE) model for deformation of an apparatus, according to the principles herein.
Figure 13B:
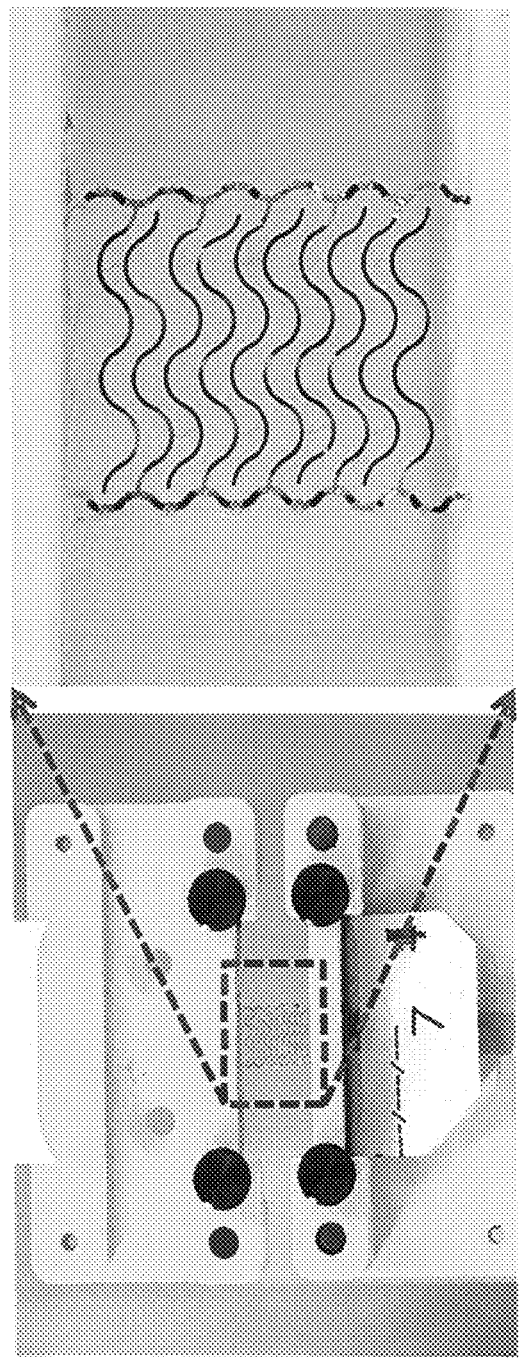
FIG. 13B shows an apparatus that is stretched at 50% elongation, according to the principles herein.

The configurations of the apparatus described herein, including the discrete interdigitated structure, allow the apparatus deformation to accommodate the natural motions of the tissue. The mechanics of the apparatus, particularly the stretching deformation, can affect apparatus performance. The stretching deformation can change the electrical properties of the system since the distance between the conductive structures is one of the parameters in the RC measurement. FIG. 13A shows a finite element (FE) model for deformation mechanism simulation and FIG. 13B shows a hydration sensor stretched at 50% elongation. The metal is Au and can be modeled as a plastic deformable solid obeying the bi-linear kinematic hardening rule. The Young's modulus is set at $30e^3$ MPa, yielding stress is 204 MPa, and the tangent modulus is 4769 MPa. The polyimide of the cross-link structures and the conductive structures coating is modeled as linear elastic with a Young's modulus of $3.2e^3$ MPa, and the backing layer (TEGADERM®) is modeled as a three-factor hyper-elastic Mooney-Rivlin solid. The three factors of the hyper-elastic Mooney-Rivlin model are: $C_{10}=-0.13$, $C_{01}=0.57$, and $C_{11}=0.13$. The FE model corresponds to the stretching test, as shown in FIG. 13B.

Figure 14B:
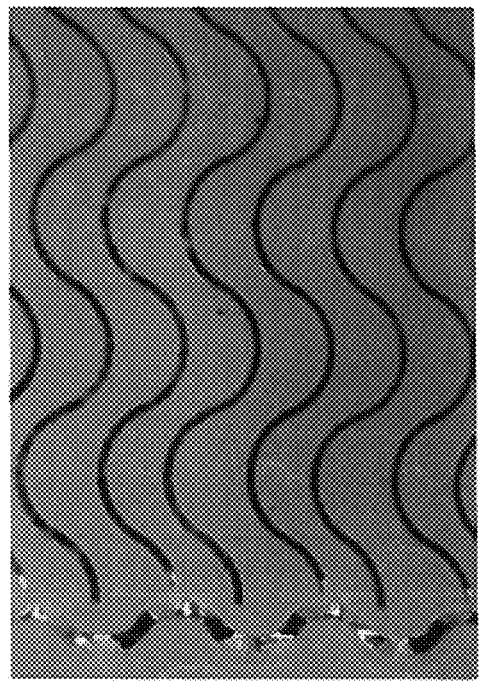
FIGS. 14A-14B show an example apparatus having interdigitated conductive structures in a relaxed state (FIG. 14A) and elongated by 50% (FIG. 14B), according to the principles herein.
Figure 14A:
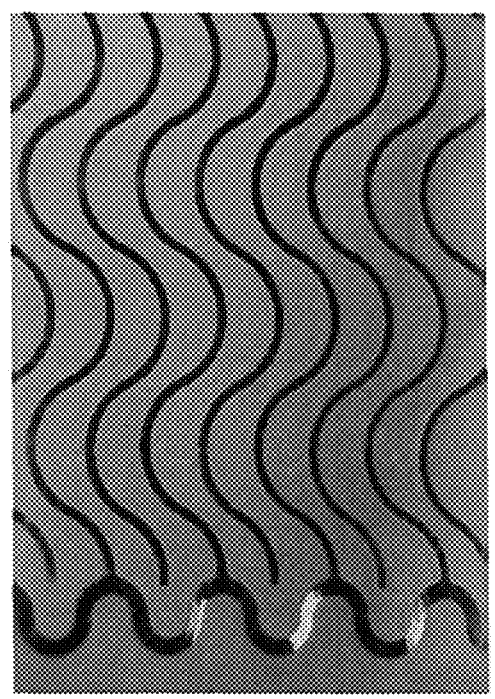

FIG. 14A shows an example apparatus that includes interdigitated conductive structures in its relaxed state. FIG. 14B shows the example apparatus of FIG. 14A subjected to about 50% elongation. Non-limiting examples of the measurement of the electrical properties of a substrate using an example apparatus such as shown in FIGS. 14A and 14B are described with reference to FIGS. 15A through 16B. The measurement can be used to quantify a complex ratio of the voltage to the current in a circuit through portions of the tissue as described above. The electrical properties can be quantified based on a magnitude and/or a phase of the electrical properties.

Figure 15A:
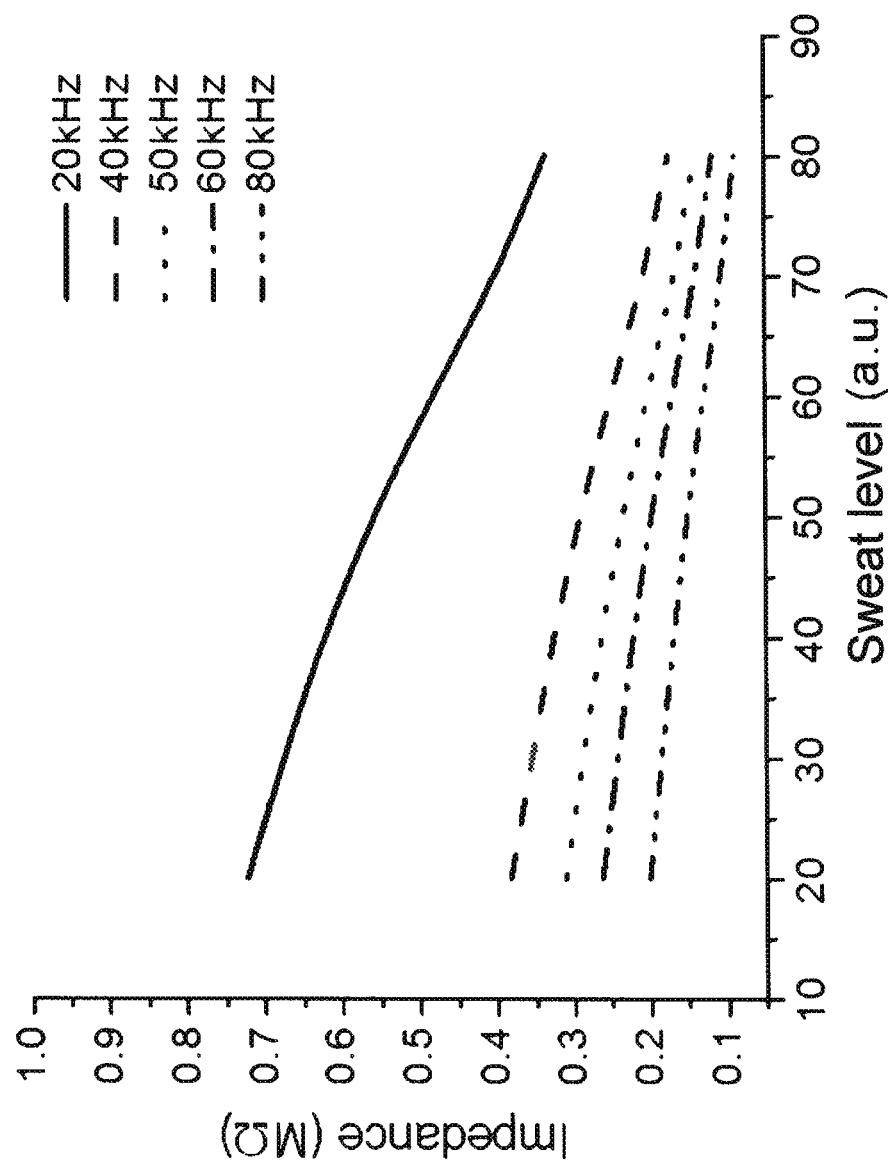
FIGS. 15A-15B show plots of the magnitude and phase, respectively, of the impedance change with the sweat level at selected measurement frequencies, according to the principles herein.
Figure 15B:
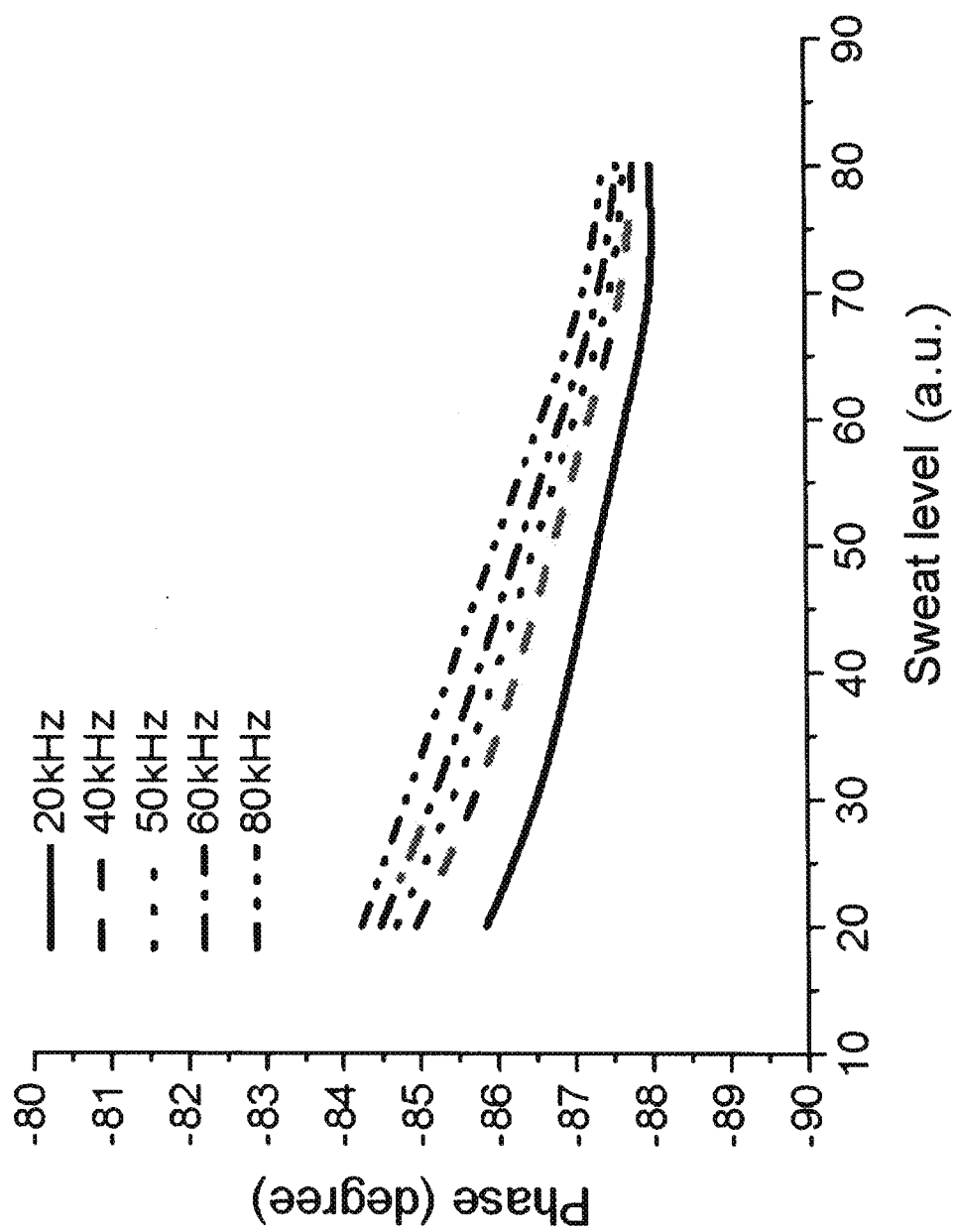

In a non-limiting example, the apparatus of FIG. 14A is used to measure the hydration level of the patch, which can be related to the sweat rate of an individual. In this example, the substrate is a cellulose pad. FIG. 15A shows the magnitude and FIG. 15B shows the phase of the impedance change with the sweat level range from 20 to 80 percent saturation at selected measurement frequencies (the radio frequency (RF) range from 20 to 80 kHz). In this example implementation, the sweat level is defined as the ratio of the volume of saline to the volume of the substrate, normalized such that 100 corresponds to full-saturation. The volume of saline added is varied, and the volume of the cellulose pad is held constant (450 mm$^3$). Initial measurements over a range of frequencies are performed to determine which frequency has the maximum change of impedance across the hydration levels, thus providing optimal sensitivity. FIG. 15A shows that the magnitude of the impedance at 20 kHz drops by 0.38 MΩ, while the impedance phase shifts by −2.13 degrees as the sweat level changes from 20 to 80 percent saturation. That is, 20 kHz provides the most sensitive output of impedance magnitude in this RF range. As the sweat level increases, the impedance drops at the RF range from 20 kHz to 80 kHz. This behavior can be attributed to an increase in electrical conductivity: increasing the amount of saline in the cellulose pad provides more ionic pathway for charge transport.

When mounted on a sweat-absorbing patch, the response of the example apparatus to fluid in the patch is quantifiable. The volume of analyte required to saturate the patch is determined in advance, then analyte is titrated onto a dry patch to systematically increase the hydration level. A dramatic drop in impedance is found between 0 and 20% hydration, after which the decline is more gradual.

The electrical performance of the example apparatus and system is observed to change as they are subjected to deformation. The change in electrical performance with changes in the tissue condition, including the changes of "resistive" impedance (R) and capacitance (C), can be described relative to equation (1) and (2).

The changes in electrical property of the substrate with changes in tissue condition can be described based on a change in the hydration state of the tissue as follows. As the sweat level in the substrate increases, the resistivity (ρ) decreases whereas the permittivity (∈) increases, resulting in the impedance (based on the resistance) dropping and capacitance rising. The decrease in resistivity can be due to the increase of mobile ions within the substrate. On the other hand, the increasing of permittivity can be explained by increasing the dipoles primarily detected by volume of sweat in the cellulose pad. These two factors (ρ and ∈) are primarily dominated by the sweat level in the cellulose pad. It should be noted that the sensor performance is also sensitive to structural parameters such as the distance between the conductive structures. According to eq. (1) and (2), as the length (l and d) between conductive structures increases because of stretching, the electrical resistance increases whereas the capacitance decreases.

As described herein, an example apparatus can be mechanically designed for comfortable wear on tissue by employing nonlinear conductive structures in a stretchable structure. The example apparatus can be configured to be sensitive to measuring frequency, sweat level and stretching deformation.

Figure 16A:
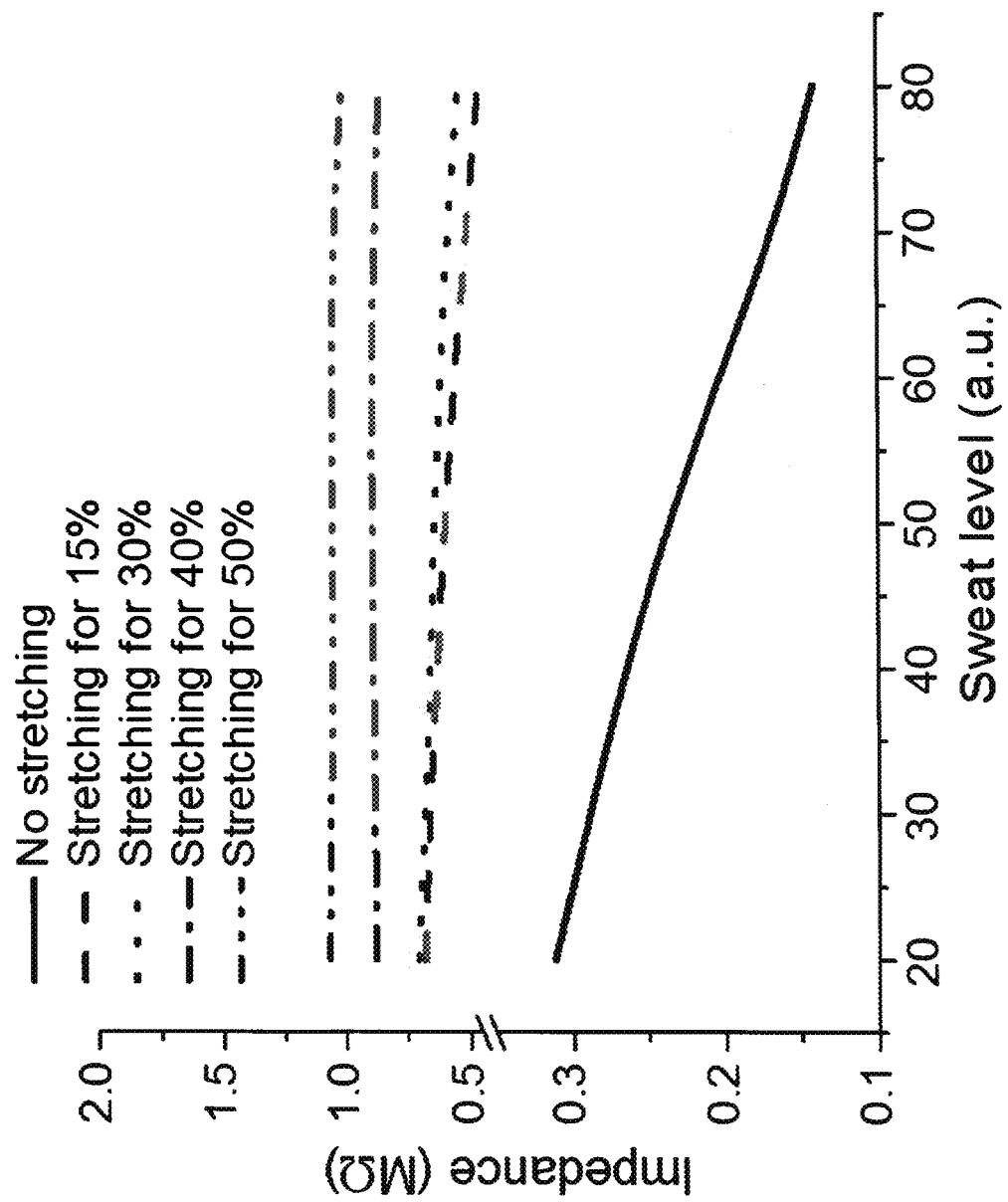
FIGS. 16A-16B show performance of the example apparatus of FIGS. 14A-14B versus impedance and capacitance, respectively, according to the principles herein.
Figure 16B:
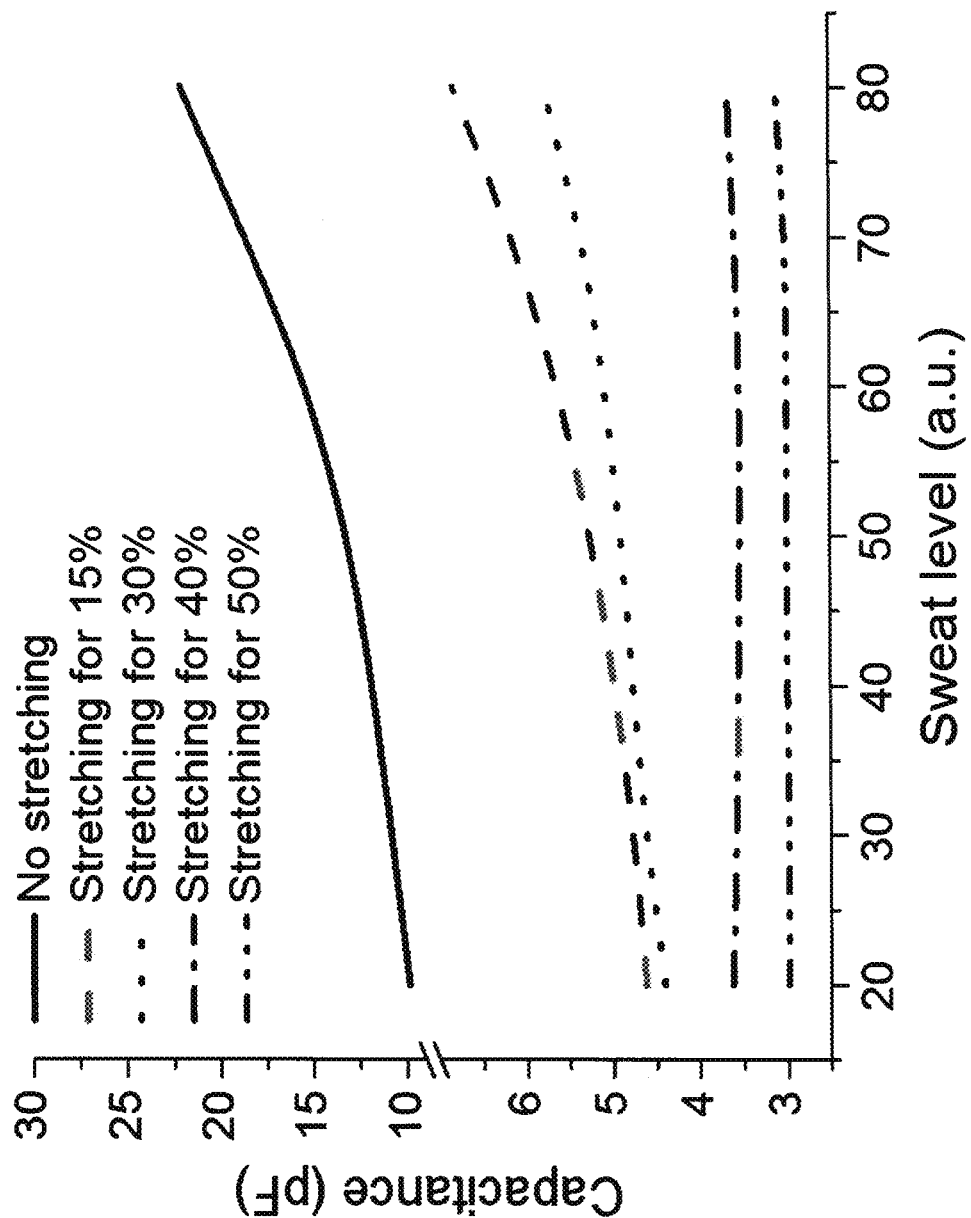

In an example implementation described in connection with FIGS. 16A and 16B, a 20 kHz signals is observed to provide sensitive performance: electrical impedance changes 50% while sweat level increases from 20 to 80 percent saturation. In addition, sensor elongation from 15 up to 50% affected the measurement sensitivity of both electrical impedance and capacitance. FIGS. 16A and 16B show performance of the example apparatus versus impedance and capacitance, respectively, while the example apparatus is being subjected to stretching at various sweat levels.

Specifically, FIGS. 16A and 16B show the impedance and capacitance change, respectively, of the example apparatus while stretched and at sweat level ranging from 20 to 80 percent saturation. The measurements are conducted at 50 kHz. As shown in FIG. 16A, the impedance increases nonlinearly with stretching due to the increasing length (l) between electrodes. In addition, the apparatus appears to lose sensitivity with respect to the sweat level when elongations become very large. FIG. 16B shows a similar trend for capacitance: the performance of the apparatus decreases nonlinearly about 80% when stretching for 15% elongation. The performance of the apparatus appears to degenerate substantially when it is stretched beyond 40% and neither impedance nor capacitance can be measured respective to the sweat level. The performance reduction may be due to the out-of-plane deformation on the stretchable interconnects causing conductive structures to lose contact with the substrate. Also, the resistive impedance and capacitance are not linear relationship to the structural parameters, l and d, as described in connection with equations (1) and (2). During stretching, however, there is a more complex deformation mechanism that causes the nonlinear relationship to the output of the electrical performance.

Figure 17:
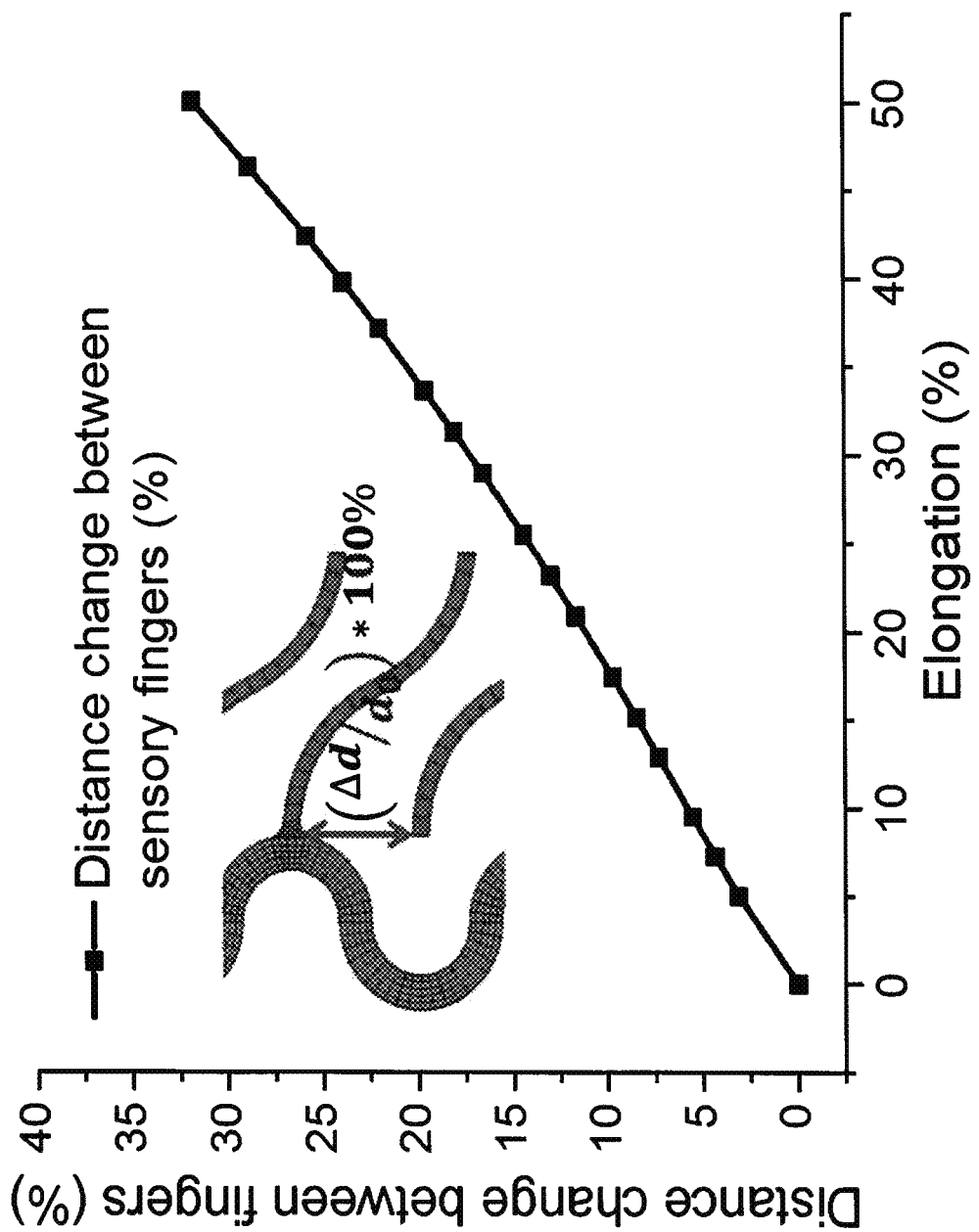
FIG. 17 shows a simulation of the distance changes between the conductive structures during stretching of the substrate, according to the principles herein.
Figure 18:
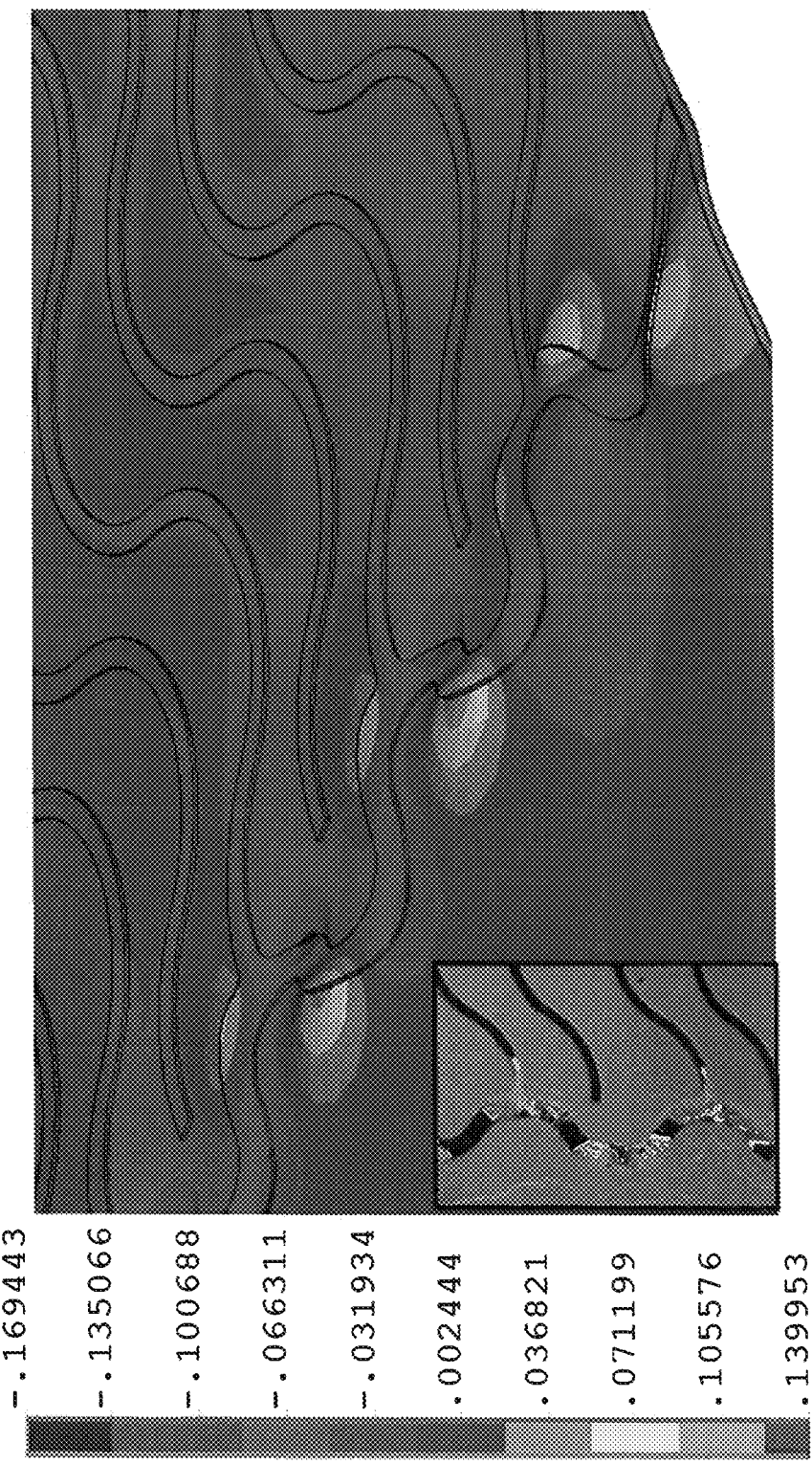
FIG. 18 shows the simulated out-of-plane deformation while the inset to FIG. 18 shows the optical image of the stretchable interconnect, according to the principles herein.

FIG. 17 shows a simulation of the distance changes (d) between the conductive structures during stretching of the substrate. The distance change between the conductive structures and the elongation are not one-to-one proportional factors. At 15% elongation, the distance changes 9% between electrodes. However, at the same elongation, the electrical performance of the sensor drops 80%. This performance drop may be due to out-of-plane deformation on the stretchable interconnects during stretching. FIG. 18 shows the simulated out-of-plane deformation while the inset to FIG. 18 shows the optical image of the stretchable interconnect. The color difference of the stretchable interconnect in the inset image is due to the out-of-plane deformation causes the light to reflect differently. At 15% elongation, the stretchable interconnect deforms by 0.14 mm in a Z-direction. This out-of-plane deformation can increase both the separation distance (d) and the length of the resistive impedance (l). As a result, not only the distance between electrodes but also the out-of-plane deformation affects the electrical performance.

An example method is provided herein for determining tissue condition based on the measurement of the electrical property of the substrate using a capacitance-based measurement at performed at an optimal frequency. The method includes receiving data in connection with a measurement of the electrical properties of the tissue, where the measurement is performed at a frequency that provides the most sensitive output of impedance magnitude in the RF range, and applying a model to the data to quantify at least one parameter of the effective circuit model. In an example, the frequency is about 20 kHz. The value of the parameter can be used to provide an indication of the tissue condition and/or to quantify the amount of stretching of the example apparatus.

Another example method provided herein for determining tissue condition based on the measurement of the electrical property of the substrate using a capacitance-based measurement that allows for a certain degree of deformation of the example apparatus. The The method includes receiving data in connection with a measurement of the electrical properties of the tissue, where the example apparatus used to make the measurement is subjected to a degree of deformation during the measurement, and applying a model to the data to quantify at least one parameter of the effective circuit model. The value of the parameter can be used to provide an indication of the tissue condition.

With respect to other hydration monitoring techniques, sweat analysis, blood analysis, muscular ultrasound analysis, and electrical analysis also can be performed. These other hydration monitoring techniques can be used to provide potential ways of corroboration or calibrating a hydration monitoring measurement performed according to a principle herein. Sweat analysis (via ionic concentration analysis) and blood analysis (via hemoglobin concentration) both may present practical issues in non-invasive sample collection as well as the scalability of the necessary components.

Using capacitance sensing to monitor hydration can present several benefits as compared to blood and sweat analysis:

Blood and sweat analysis may likely require disposable, adhesive sensor units and may be costly.

There are specific locations, including the thigh and upper bicep, at which capacitance sensing works better for hydration monitoring, and these locations are conducive to use of a device during vigorous activity. The best locations for a sweat or blood monitoring system might be harder to determine.

The capacitance sensing can be completely non-invasive. Such sensors have been worn for periods of up to a week without discomfort, and survive daily activities such as exercise and showering. Lifetime is primarily limited by the turnover of cells in the skin.

A system, apparatus and method according to a principle herein provides the following benefits:

The sensor circuitry can be configured to be fully flexible, stretchable and conformable for a more comfortable and portable user experience, whether incorporated into an arm/leg band or a form-fitted garment.

Hydration status may be viewed in real-time based on measurements using a sensor incorporated in an article of clothing or gear, including an arm/leg band or form-fitted clothing item, or a patch placed on the skin.

An example device may include a sensor coupled to LED indicator lights for indicating sweat level (which can be related to hydration level).

An example device may include a sensor described herein in a patch placed on the skin, or an article of clothing or gear, that is configured to transmit data (including by wireless communication or using IR); a handheld device (such as but not limited to a smartphone), can be brought in proximity to the sensor to receive a quantitative indication of the electrical measurement performed by the sensor The arm/leg band may be wireless and transmit data to mobile devices and portable music players.

Through innovative low-power management techniques the circuit can operate on a very small power source.

Through innovative electronic circuit design, small changes in capacitance (and in some examples impedance measurements as well) can be detected.

A sensor for performing capacitance measurements may be fabricated on a flexible and/or stretchy substrate that may be worn on the skin, including as a skin patch, or integrated into form-fitted clothing or other gear (such as an arm or leg band). In one example, the sensor is designed with a serpentine geometry to allow the sensor to flex with the flexible and/or stretchy substrate. The sweat level (which can be related to a state of hydration) is determined by measuring the capacitance between the two contacts of the capacitance sensor. Changes in a measured capacitance can reflect changes in the state of hydration.

It is also contemplated that this sensor may be used in combination with other types of sensors that measure the composition of sweat (e.g., sensors that measure conductivity or sensors that measure the concentration of selective ions such as sodium potassium and calcium, and others).

A system, method and apparatus according to a principle described herein can be relevant to at least four commercial segments. The first segment is athletics—including both casual and highly competitive athletics. Hydration level measurement can help athletes greatly in monitoring their training routine as well as offer a safety precaution to help prevent excessive dehydration. The systems, apparatus and methods disclosed here are used to indicate when an athlete needs to drink more water or electrolyte solutions like a sport or energy drink. The second applicable segment is the military. Soldiers, pilots, etc. may benefit greatly from hydration monitoring during live combat and training. Dehydration, even at small levels, can impact physical and mental performance and pose serious safety issues. Monitoring hydration levels can help a soldier remain hydrated to avoid any of these risk factors. The third potential market segment is the beauty and cosmetics market where local skin hydration may be monitored and various lotions or other product applied when the state of hydration is deemed too low. Appropriate levels of hydration can prevent skin from drying out and, over time, create healthy skin appearance. In another example, the level of hydration can serve as an indicator of skin firmness. The fourth segment is in the health and wellness/medical monitoring market. This may be part of a general wellness program where hydration levels are monitored as one of many health measurements and be integrated into general assessment for health tracking, diagnosis and long-term monitoring.

Inductance-Based Measurements

In an example according to the principles described herein, an apparatus can be configured to measure electrical properties of the tissue through an inductance-based measurement.

Figure 19A:
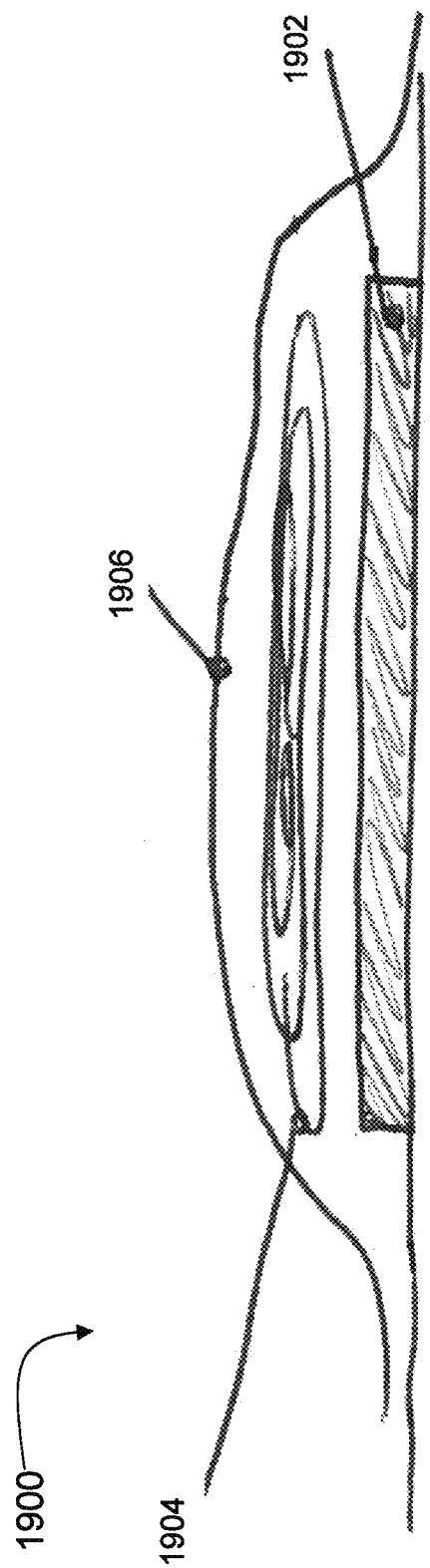
FIG. 19A-19B show an example apparatus that include an inductor structure, according to the principles herein.

A non-limiting example of an apparatus 1900 for performing inductance-based measurement is shown in FIG. 19A. An apparatus 1900 according to this example implementation can include a substrate 1902 disposed above the tissue, where the substrate 1902 is formed from a material that exhibits a change in a state with a change in tissue condition. As a non-limiting example, the substrate 1902 can be formed from a material that changes hydration state with a change in the sweat level of the tissue (which can be related to hydration level). The apparatus 1900 further includes at least one first inductor structure 1904 disposed above the substrate. As non-limiting examples, the inductor structure 1904 can be a spiral coil structure, a cylindrical coil structure, or a toroidal structure. The inductance-based measurement can be performed by applying a potential to the at least one first inductor structure 1904. An electrical property and/or a physical property of the at least one first inductor structure 1904 changes with the change in the state of the substrate. A measure of the electrical property or the physical property of the at least one first inductor structure 1904 using the apparatus is used to provide an indication of the tissue condition. The apparatus 1900 further includes an encapsulation layer 1906.

In an example, the electrical property can be a magnetic flux density from the at least one first inductor structure.

In an example, the encapsulation layer 1906 can be a polymer, including a polymer having an adhesive portion. For example, the adhesive portion of the encapsulation layer 1908 can be present where the encapsulation layer 1906 makes physical contact with the tissue (including attaching the apparatus to the tissue). The adhesive portions can be used to mount the apparatus 1900 to the tissue. In this manner, the apparatus can be maintained in contact with the tissue.

In another example, an electrically conductive gel can be disposed between the apparatus and any absorbing layer present between the apparatus and the tissue. The conductive gel can deform easily and allow the spacing to change, but maintain the electrical distance between the apparatus and the absorber at substantially zero.

In an example, the electrical property is a magnetic flux density from the at least one first inductor structure that reaches the region.

Figure 19B:
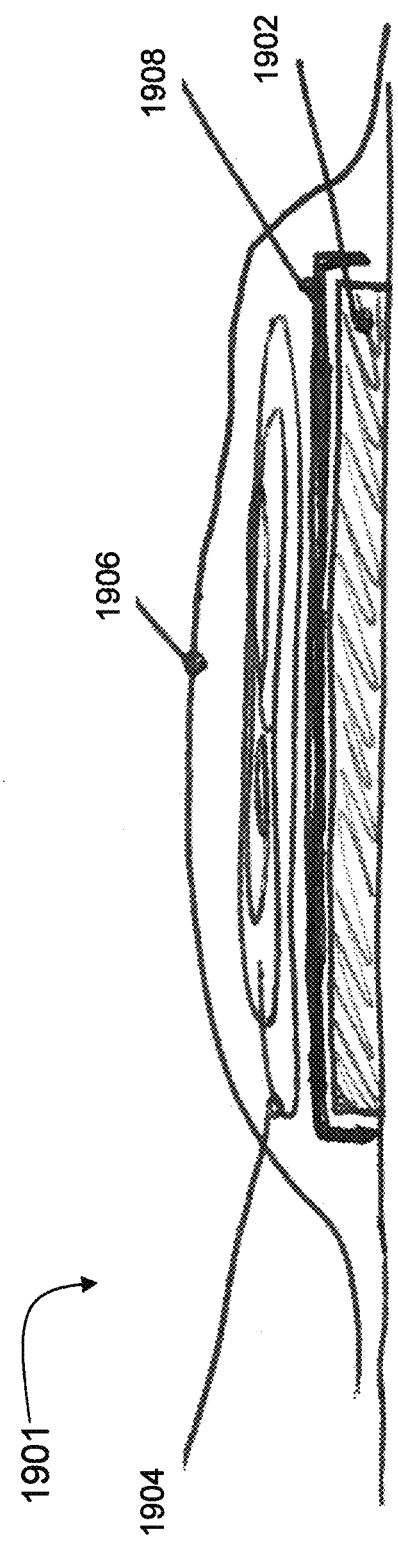

As shown in FIG. 19B, an apparatus 1900 for performing inductance-based measurement can include the substrate 1902, at least one first inductor structure 1904 and an encapsulation layer 1906. The apparatus further includes a separator layer 1908 disposed between the at least one first inductor structure 1904 and the substrate 1902.

In an example, the separator layer is a non-conductive material, including a material based on a polymer.

Figure 20:
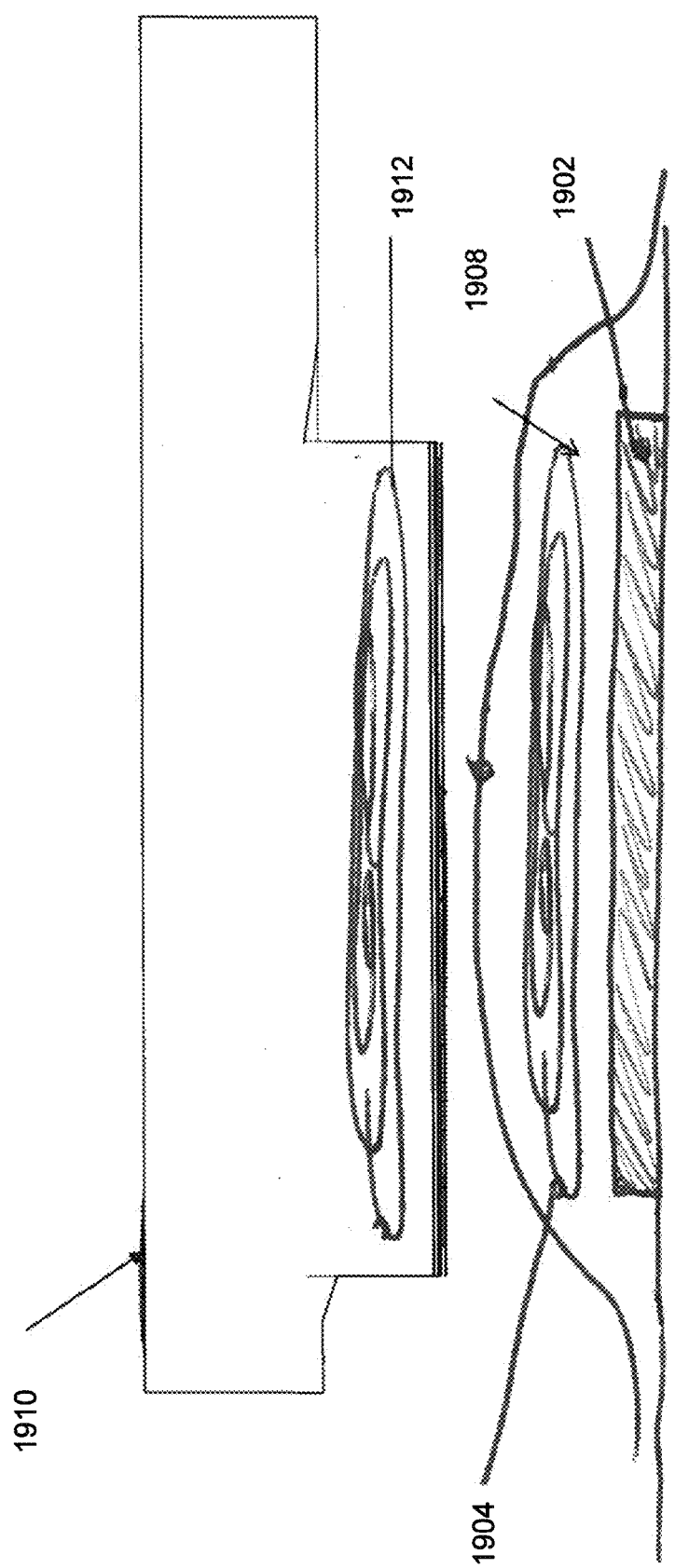
FIG. 20 shows a system that includes an example reader including an inductor structure, according to the principles herein.

In an example implementation, a reader can be used to perform the electrical measurement of the tissue. As shown in FIG. 20, an example reader 1910 can include at least one second inductor structure 1912. A measure of a change in an electrical property of the at least one second inductor structure 19192 brought in proximity to the at least one first inductor structure 1904 provides the measure of the electrical property of the at least one first inductor structure 1904. The measure of the electrical property or the physical property of the at least one first inductor structure 1904 using the reader 1901 is used to provide an indication of the tissue condition. For example, a calibration standard can be generated as described above (in connection with the capacitance-based system) based on inductance-based electrical measurements of a training set of tissue samples in different known tissue conditions.

The second inductor structure 1912 can be the same configuration as the first inductor structure 1904.

In a non-limiting example, the reader is a handheld device such as a smartphone, a tablet, a slate, or other handheld computing device. A processor of the handheld device can be used to analyze the data from the inductance-based measurement to provide the indication of the tissue condition.

RF inductor coils are used that are sensitive to the impedance of the underlying tissue. Likewise, a passive RF induction coil on the skin to measure changes in impedance of the underlying tissue may be correlated with changes in the state of hydration of the tissue. This offers a simple and non invasive method for hydration assessment that can easily be integrated into a wearable (stretchy, flexible or conformal) form factor.

Using tissue impedance-inductance to monitor hydration has the several specific advantages over blood and sweat analysis: Blood and sweat analysis can require disposable, adhesive sensor units and may be costly. A RF inductor can easily be designed to be reusable. There are specific locations, including the thigh and upper bicep, at which RF impedance testing works best for hydration monitoring, and these locations are conducive to use of a device during vigorous activity.

An RF inductor coil may be fabricated on a flexible and/or stretchy substrate that may be worn on the skin or integrated into form-fitted clothing. The tissue condition, including its state of hydration, is determined by measuring the resonant frequency of the coil. This frequency is related to the impedance of the tissue adjacent to the coil. Changes in resonant frequency may be correlated with changes in impedance, which in turn reflects changes in the state of hydration. The depth of tissue to which the coil is sensitive to changes in impedance scales with the radius of the coil. Small coils (<1 cm) are designed to be sensitive primarily to the hydration of the skin while larger coils (>1 cm) are designed to be sensitive to the state of hydration of muscle.

In accordance with various examples herein, the apparatus can be used to provide real-time data giving information such as:
1. Total volume of sweat lost;
2. Composition of the sweat lost (major electrolytes lost in sweat are Sodium, Potassium, Calcium) with an active monitor.

Example apparatus and systems herein for real-time monitoring of hydration through a passive, non-invasive device based on volume of sweat lost through the placement of RF conductor coils on a hydrophilic patch (i.e. hydrophilic polyurethane) over a constant surface area of the skin. The RF coil and the patch may be housed in a bioadhesive patch that contacts the skin and only allows for sweat from the specific surface area to be collected. The hydrophilic patch—such as TECOPHILIC® (Lubrizol Corporation, Wickliffe, Ohio)—collects the amount of sweat lost over that surface area and distributes it uniformly. The changes in resonant frequency of the RF coil on top of the hydrophilic patch can be correlated to the changes of impedance in the hydrophilic patch as the sweat accumulates. The changes can be measured through the use of a portable (handheld) RF reader. A small RF coil can be used to measure the uniform distribution of the sweat accumulated in the hydrophilic polyurethane patch over the surface area noted above. The correlated data can then give a state of hydration based on volume of sweat lost over the entire Body Surface Area (BSA) by extrapolating the surface area of the patch over the surface area of the entire body. The average BSA is widely taken to be 1.73 $m^2$ for an adult with 1.9 $m^2$ for a male and 1.6 $m^2$ for a female. This can be further customized if both height and weight are known through the Dubois & Dubois formula for BSA (or another formula for BSA that is agreed upon):

$$BSA(m^2) = 0.007184 \times \text{weight(kg)}^{0.425} \times \text{height(cm)}^{0.725}$$

$$= \frac{\text{weight(kg)}^{0.425} \times \text{height(cm)}^{0.725}}{139.2}$$

The example apparatus can be housed in an elastomeric patch adhering to the skin. The patch may include a cavity containing an absorbent wicking hydrophilic material that draws and distributes sweat lost during exertion. The patch may be designed in such away that the accumulation of sweat in the hydrophilic materials correlates directly with flux of sweat through the skin: that is, amount of sweat per square-meter of skin. This flux multiplied by the BSA calculated above gives an substantially absolute measure of the amount of fluids lost over a period of time. The wearer can then replenish or rehydrate with precisely the amount of fluids lost. The patch may include an elastomer having pores restricting access to the skin and allowing a controlled flow of sweat into the cavity. An RF coil on the outer surface of the patch may be stimulated by an external swept-frequency RF transceiver. The center frequency and Q of the coil changes in response to the moisture content of the patch, which will be detected by the external transceiver. The baseline for this measurement is the patch when it is first applied to skin.

Another implementation includes a metal mesh on the lower surface of the elastomer, either on the skin side or the bottom of the cavity. The mesh isolates the skin surface from the RF sensing coil and substantially eliminates the natural variation of coil response depending on individual body composition and starting hydration, allowing one-time factory calibration of the patches.

Another example implementation includes an embedded sensing coil inside the cavity and providing isolation both above and below the cavity. The isolation helps protect the sense coil from subject variations as well as stray electromagnetic fields. A separate communications coil linked to the sense coil but outside the shielded cavity may be included in this instantiation. The link may be either passive or active. A passive link may be AC coupled or DC coupled. An active link may contain transistors, RF energy harvesting and storage, Rx, sense, and Tx phases, timing and control, similar to an RFID tag.

Figure 21:
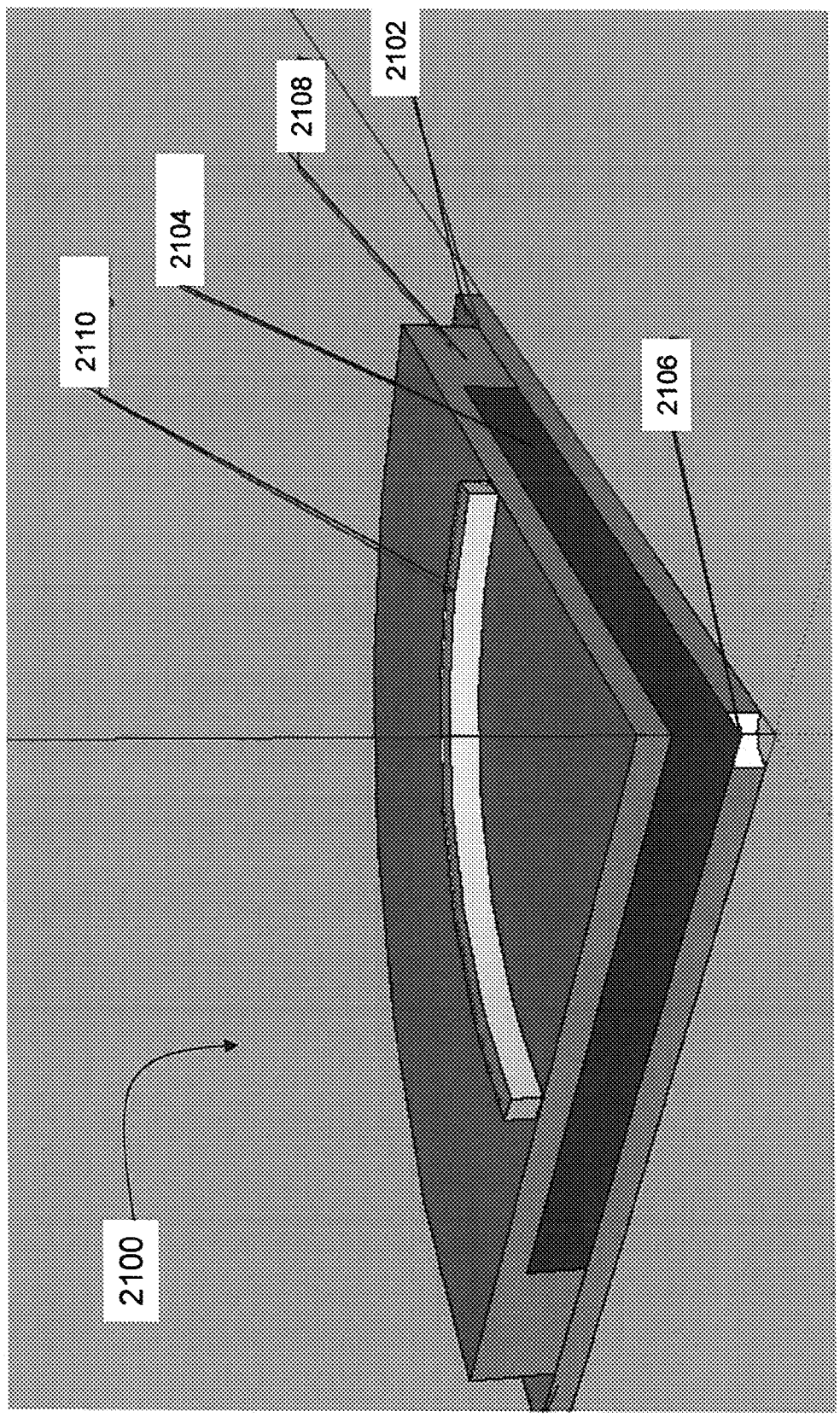
FIGS. 21-23 show quarter sections of example sensing patches, according to the principles herein.

The example apparatus of FIG. 21 shows a quarter of a sensing patch 2100 that includes an elastomer substrate 2102, a TECOPHILIC® material 2104, an opening 2106 providing a pore that allows moisture to penetrate from the tissue to the patch, an elastomer cap 2018, a sensing coil 2110 (first inductor structure) to detection hydration level of TECOPHILIC® layer 2104.

Figure 22:
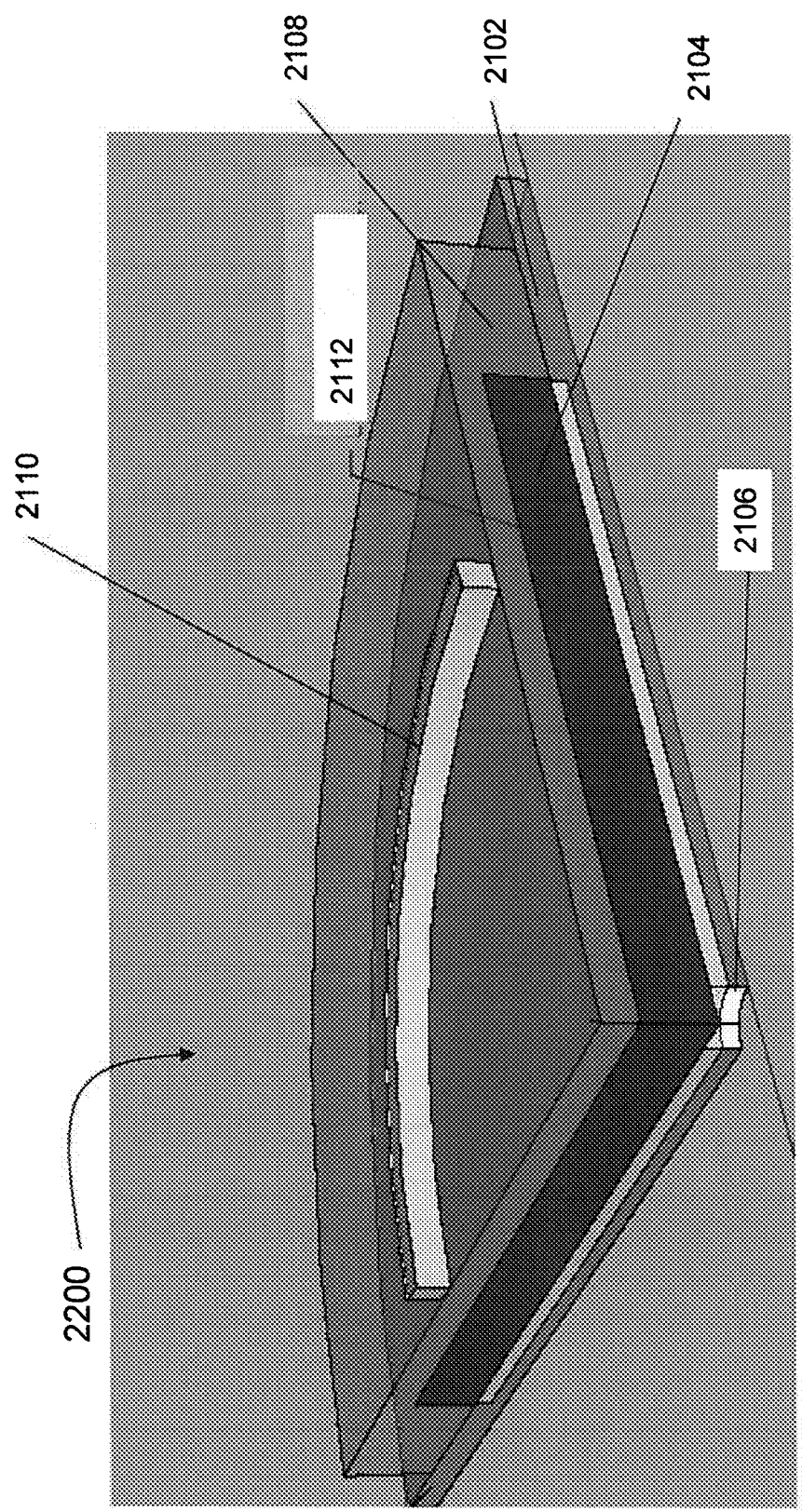

The example apparatus of FIG. 22 shows a quarter of sensing patch 2200 that includes a shielding mesh 2112 below the TECOPHILIC® layer, so that the coil detects only moisture in the TECOPHILIC® layer and not in the skin.

Figure 23:
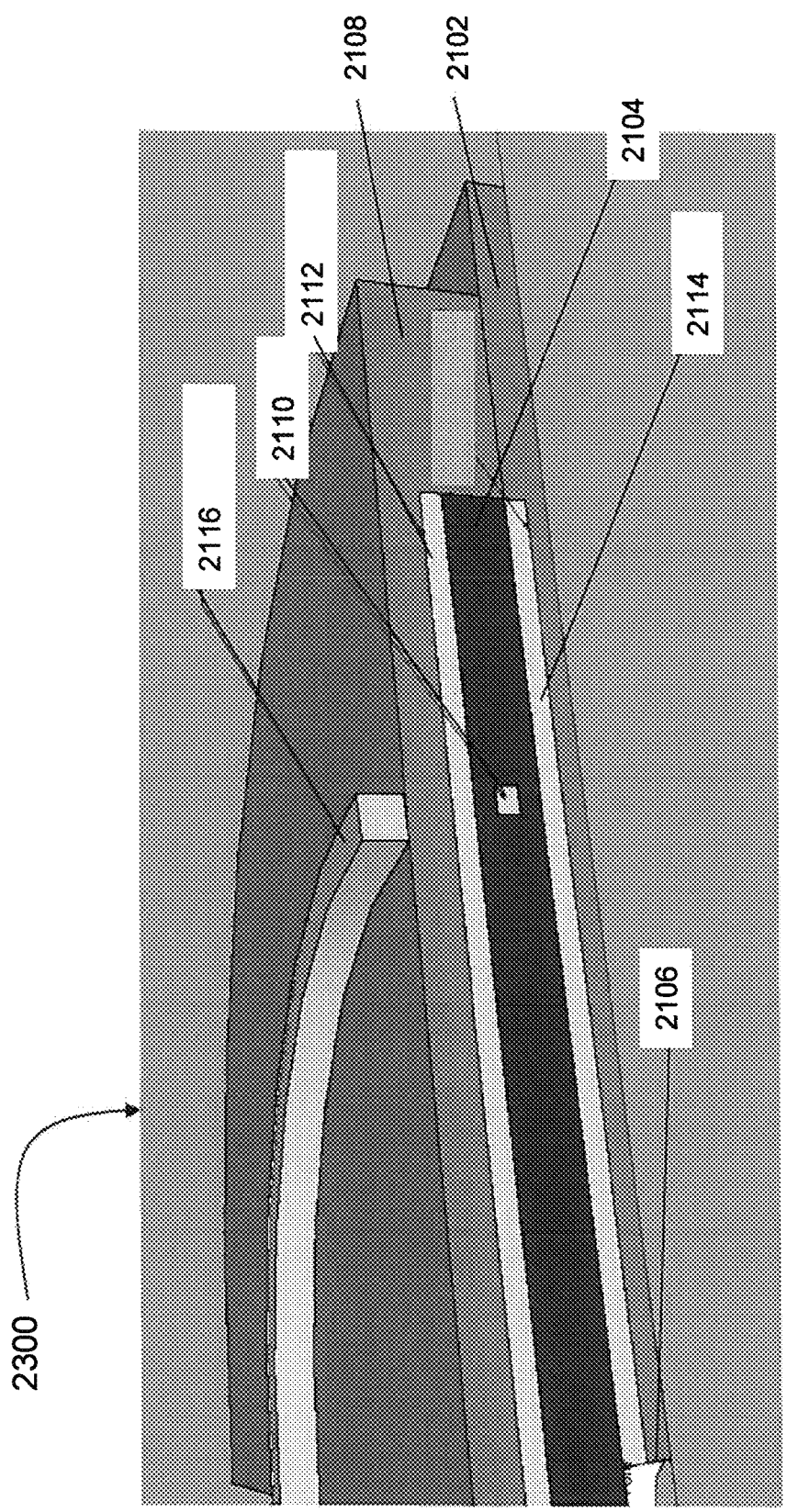

The example apparatus of FIG. 23 shows a quarter of sensing patch 2300 that includes both top shielding 2114 and bottom shielding 2112 to provide electromagnetic isolation of the sensing coil 2110. A second coil 2116 is used for communication of the tissue condition measurement made using the sensing coil 2110.

Ultrasound-Based Measurements

Sweat analysis, blood analysis, and muscular ultrasound analysis as potential ways of monitoring hydration. Sweat analysis (via ionic concentration analysis) and blood analysis (via hemoglobin concentration) both presented practical issues in non-invasive sample collection as well as the scalability of the necessary components. Ultrasound velocity to determine tissue hydration level as an indicator for overall hydration level utilizes a relationship proven by research and is a method with minimal potential for complication.

Figure 24:
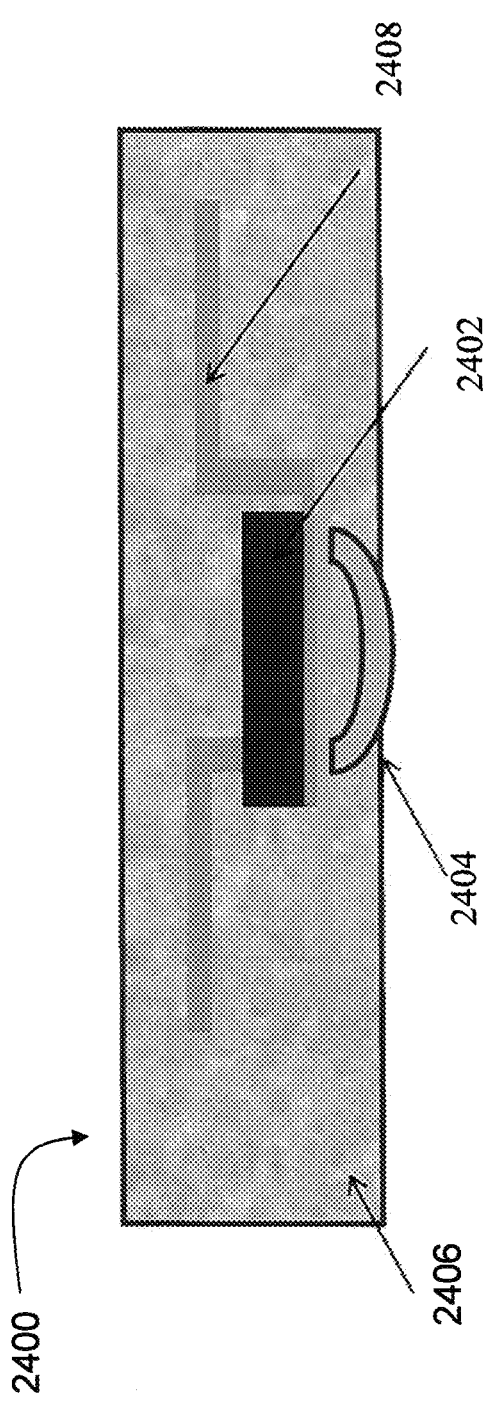
FIG. 24 shows a cross-section of an example ultrasound system, according to the principles herein.

FIG. 24 shows a cross-section of an example ultrasound system 2400 that can be used in conjunction with a capacitance-based system and/or an inductance-based system described herein to provide data indicative of the electrical properties of the tissue. Example ultrasound system 2400 includes a piezoelectric crystal 2402, a hard polymer focusing element 2404, a metal plate 2406, and the wiring 2408 to supply a voltage to the piezoelectric crystal 2402.

Figure 25:
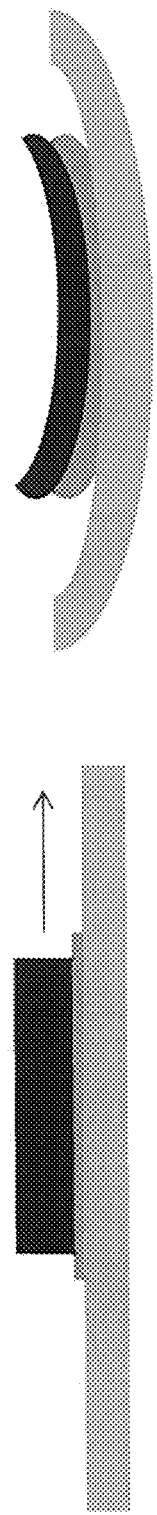
FIG. 25 illustrates an example operation of the example ultrasound system when a voltage is applied, according to the principles herein.

FIG. 25 shows an example operation of the example ultrasound system 2400 when a voltage is applied. The alternating voltage causes a shape change in the piezoelectric crystal 2402, and the shape change helps to generate the ultrasound waves.

Figure 26B:
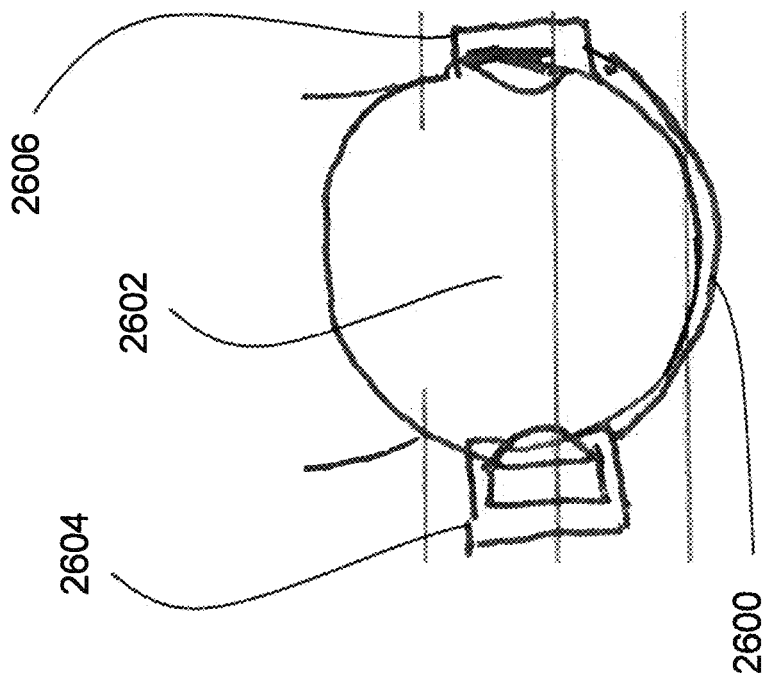
FIG. 26B shows a cross-section of the device mount of FIG. 26A, according to the principles herein.
Figure 26A:
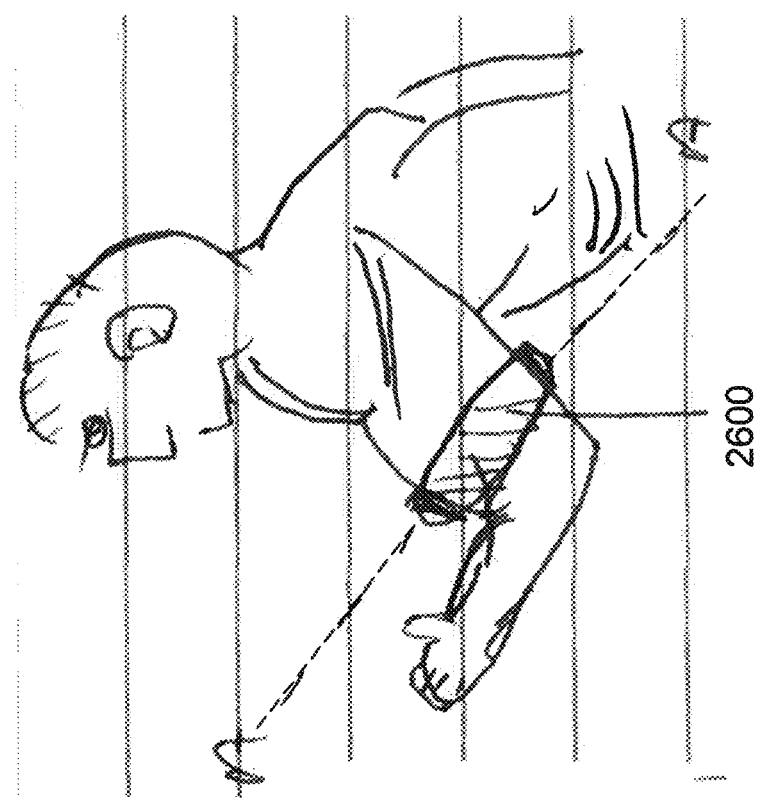
FIG. 26A shows an example device mount about a bicep tissue, according to the principles herein.

FIG. 26A shows an example device mount 2600 about a bicep tissue. FIG. 26B shows a cross-section of the device mount 2600 disposed about the bicep tissue 2602. The ultrasound system includes an ultrasound generator 2604 and an ultrasound receiver 2606.

Using ultrasound velocity or tissue impedance to monitor hydration has the several specific advantages over blood and sweat analysis:

Blood and sweat analysis would likely require disposable, adhesive sensor units and may be costly. An ultrasound device can easily be designed to be reusable.

There are specific locations, including the thigh and upper bicep (see FIG. 26A), at which ultrasound velocity assists in hydration monitoring, and these locations are conducive to use of a device during vigorous activity. The optimal locations for a sweat or blood monitoring system might be harder to determine.

The ultrasonic device can be made non-invasive.

Non-limiting examples of benefits of the present disclosure include the following:

The sensor circuitry is fully flexible, stretchable and conformable for a more comfortable and portable user experience, whether incorporated into an arm/leg band or a form-fitted garment.

Hydration status readings will be derived using the average of velocity readings taken from multiple transducer-sensor pairs stationed in multiple arrays throughout the band. An increased number of trials will help to increase the accuracy of the readings. Additionally, the average reading will help mitigate any inconsistencies caused by small potential changes in transducer-sensor separation due to the conformal nature of the band.

Hydration status may be viewed in real-time on the arm/leg band or form-fitted clothing item via the included LED indicator lights.

The arm/leg band may be wireless and transmit data to mobile devices and portable music players.

Through innovative low-power management techniques the circuit can operate on a very small power source.

An RF inductor coil may be fabricated on a flexible and/or stretchy substrate that may be worn on the skin or integrated into form-fitted clothing. The state of hydration is determined by measuring the resonant frequency of the coil. This frequency is related to the impedance of the tissue adjacent to the coil. Changes in resonant frequency may be correlated with changes in impedance, which in turn reflects changes in the state of hydration. The depth of tissue to which the coil is sensitive to changes in impedance scales with the radius of the coil. Small coils (<1 cm) are designed to be sensitive primarily to the hydration of the skin while larger coils (>1 cm) are designed to be sensitive to the state of hydration of muscle.

In various examples, these sensors—ultrasound and impedance (inductance-based and/or capacitance-based)—may be used alone or in combination. It is also contemplated that these sensors—ultrasound and impedance (inductance-based and/or capacitance-based)—may be used in combination with other types of sensors that measure the composition of sweat (e.g., sensors that measure conductivity or sensors that measure the concentration of selective ions such as sodium potassium and calcium, and others).

Example components are the ultrasonic transducer/receiver array circuits. The ultrasonic transducers and receivers are piezoelectric disc actuators laid into a circuit with a series of analog-to-digital converters (ADCs) that process the signals from the transducer-receiver pairs.

These transducer/receiver circuits are laid into the sleeve of a t-shirt, the leg of a pair of compression shorts, or a sport armband or legband made of a formfitted, flexible, stretchable material such as neoprene, spandex or other types of polymer materials. One exemplary configuration is three or more arrays of transducers and receivers spaced equidistant from each other. Each section contains two transducers and two receivers. Each transducer is responsible for communicating with a receiver in an adjacent array and vice versa. The transducer-receiver sections do not communicate with diagonal sections due to bone interference, only adjacent sections.

Hydration status is monitored based upon the velocity of ultrasound waves through the muscular tissue. There is a proven linear proportionality between tissue hydration level and the velocity of ultrasonic waves through the tissue (Topchyan, et al. Ultrasonics 44, 2006, 259-264). As the muscle tissue becomes more dehydrated, ultrasound velocity will become faster. This linear relationship does not hold at extreme levels of dehydration. The ADCs within the circuits measure the time differential between the ultrasound signal propagation at the transducer and signal reception at the receiver. This time differential is then divided by the distance between the transducer and receiver to obtain an ultrasound velocity. This is measured at regular intervals. In an example where these measurements are made every thirty seconds, one overall velocity will be calculated from an average of the readings from each of the eight transducer-receiver pairs. Each pair will be activated once during each thirty-second interval to retrieve a velocity reading, and only one pair will be activated at a time to eliminate any possibilities of constructive or destructive interference.

Example Systems for Using Apparatus for Measuring Tissue Properties

Figure 27:
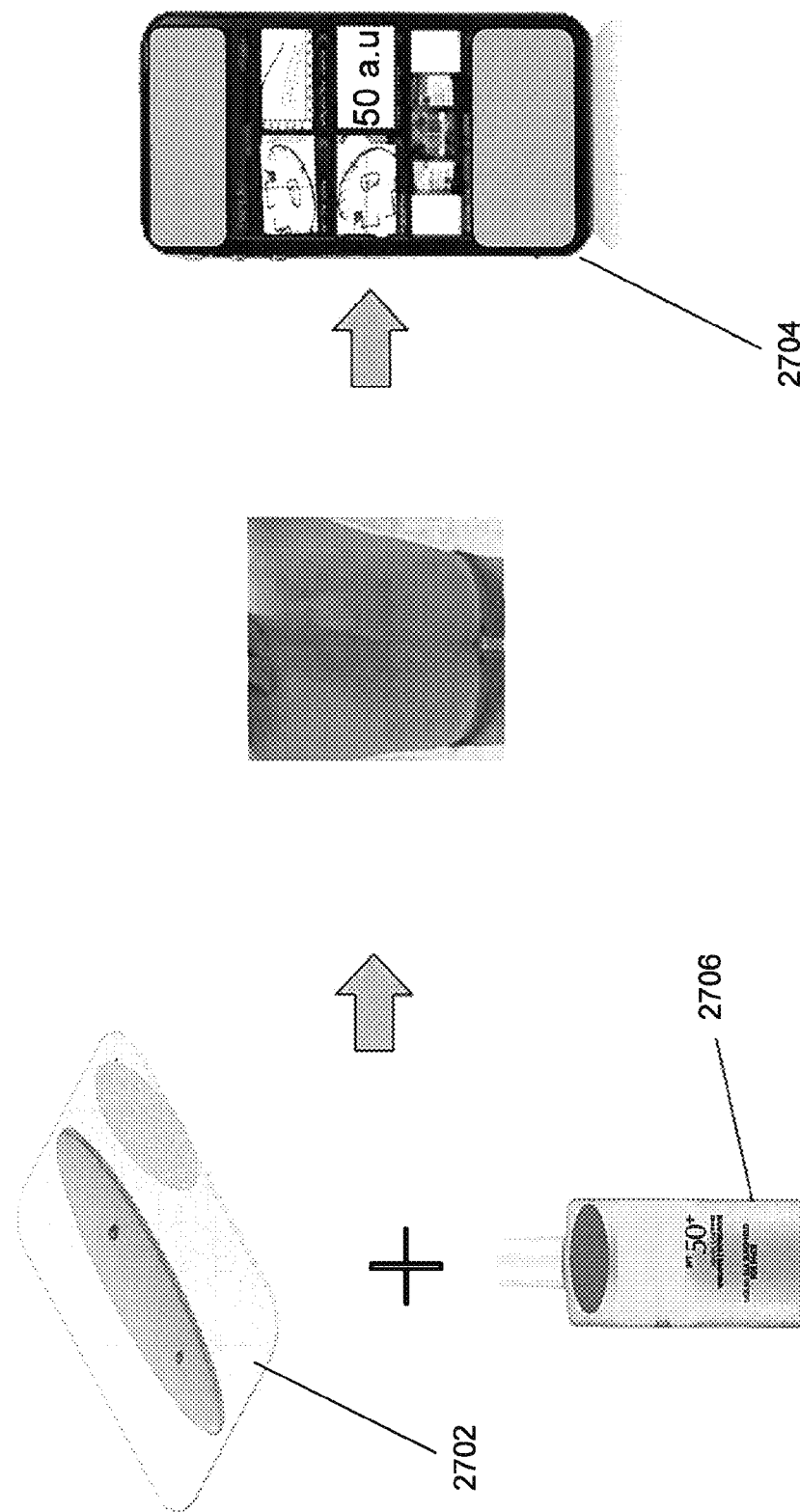
FIG. 27 illustrates use of a patch with a handheld device for monitoring tissue condition, according to the principles herein.

In an non-limiting example, an apparatus or system according to any of the principles described herein can be mounted to the tissue as a part of a patch. An example of a patch 2702 that can include at least one of any of the apparatus described herein is shown in FIG. 27. The patch 2702 may be applied to tissue, such as skin. A handheld device 2704 can be used to read the data in connection with the electrical measurement performed by the apparatus of the patch 2702. For example, the patch 2702 can include a transmitter or transceiver to transmit a signal to the handheld device 2704. The data in connection with the electrical measurement can be analyzed by a processor of the handheld device 2702 to provide the indication of the tissue condition according to the principles described herein.

As shown in FIG. 27, the patch may be used in connection with a substance 2706 that is applied to the tissue. The substance 2706 may be configured to change the condition of the tissue, including treating a disease of the tissue. For example, the substance 2706 may be configured to be applied to the skin tissue to provide protection against the UV. In this example, the apparatus of the patch would be configured to perform electrical measurements to provide an indication of UV and/or SPF sensing on the tissue, to prevent sun damage and/or to recommend protective products. In another example, the substance 2706 may be configured to be applied to the tissue to treat a disease or other malformation of the tissue.

In an example, the patch 2702 may be a disposable adhesive patch that is configured for comfort and breathability.

In another example, the patch 2702 may be a more durable sensor patch that is configured for comfort and long-term wear. The sensor patch may include onboard sensors to measure the tissue condition of interest, a memory to log the data in connection with the electrical communication, and a near-field communication device that allows a scan of the sensor patch with a handheld device to perform a status check and download. Non-limiting examples of the handheld device include a smartphone, tablet, slate, an e-reader or other handheld computing device. The sensor patch may include an energy storage device, such as a battery, to provide the voltage potential used for performing the measurements as described hereinabove.

In an example, the system may include the patch 2702 and a charging pad (not shown). The patch 2702 may be placed on the charging pad to charge the energy storage component of the patch 2702. The charging pad may be charged in an AC wall socket. The charging pad may be an inductive charging pad.

In an example implementation, the patch 2702 can include an apparatus for performing SPF monitoring based on the electrical information from a capacitance-based and/or an inductance-based measurement. The example apparatus according to this implementation can include an onboard UVA and/or UVB sensor. The tissue condition that is reported is the sun protection effectiveness of a sunscreen product for protection of the tissue. An example disposable patch according to this implementation can provide a surface that is engineered to simulate skin wetting properties to, accurately represent sunscreen distribution.

The example SPF monitoring system can use a durable sensor patch along with disposable adhesive patches. In an example method for use of the SPF monitoring system, the patch 2702 can be placed in a discreet high-exposure location on a person's body if extended sun exposure is expected. Over time, e.g., throughout the day, a NFC-enabled handheld device can be placed in proximity to the patch 2702 to check how much sun protection still remains. The handheld device can include an application (an App) to log and track "SPF state." That is, the App on the handheld device can include machine-readable instructions such that a processor unit of the handheld device analyzes the electrical measurements from the apparatus of the patch 2702 and provides the indication of the tissue status (SPF state) based on the analysis. The App can include machine-readable instructions to provide (i) product recommendations, (ii) suggestions to re-apply a product, or (iii) present an interface that facilitates the purchase of, or obtaining a sample of, recommended products. After use, such as at the end of the day, a consumer may dispose of the Adhesive patch, and retain the sensor patch reuse at a later time. The sensor patch can be re-charged using a charging pad as described herein.

In another example implementation, the patch 2702 can include an apparatus to perform as a UV dosimeter based on the electrical information from a capacitance-based and/or an inductance-based measurement. The example apparatus according to this implementation can include an onboard UVA and/or UVB sensor. The tissue condition that is reported is the UV dosage exposure of an individual.

The example UV dosimeter system can use a durable sensor patch along with disposable adhesive patches. In an example method for use of the UV dosimeter system, the patch 2702 can be placed in a discreet high-exposure location on a person's body if extended sun exposure is expected. Over time, e.g., throughout the day, a NFC-enabled handheld device can be brought in proximity to the Adhesive patch to download logged data, gathered throughout use of the patch 2702. The App can be used to track "personal sun exposure state." That is, the App on the handheld device can include machine-readable instructions such that a processor unit of the handheld device analyzes the electrical measurements from the apparatus of the patch 2702 and provides the indication of the tissue status (personal sun exposure state) based on the analysis. The App can include machine-readable instructions to provide and can provide (i) product recommendations, (ii) suggestions to re-apply products, or (iii) present an interface that facilitates the purchase of, or obtaining a sample of, recommended products. After use, such as at the end of the day, the individual may dispose of the Adhesive patch, and retain the sensor patch for reuse at a later time. The sensor patch can be re-charged on charging pad, e.g., overnight.

In another example implementation, the patch 2702 can include an apparatus to perform as a hydration and/or firmness monitor based on the electrical information from a capacitance-based and/or an inductance-based measurement. The example apparatus according to this implementation can include an onboard hydration sensor. The tissue condition that is reported is the tissue hydration and/or firmness of an individual. Based on the indication, the patch 2702 can perform diagnosis and recommendation for personalized skin hydration and firmness product treatments.

The example hydration and/or firmness monitoring system can use a durable sensor patch along with disposable adhesive patches. In an example method for use of the hydration and/or firmness monitoring system, the individual may create a personal profile and affiliate a product choice with that profile on a handheld device. An App that can be used to generate the profile may be downloaded to the handheld device. After application of a product, e.g., at night, an individual may place one or more patches 2702 on an area of interest on the body. The individual may bring the NFC-enabled handheld device in proximity to the patch(es) 2702 to download data gathered intermittently during use of the patch(es) 2702. The App can include machine-readable instructions to track "personal hydration and firmness states." In another example, the App can include machine-readable instructions to provide (i) product recommendations, (ii) suggestions to re-apply products, or (iii) present an interface that facilitates purchase of, or obtaining a sample of, recommended products. The individual may repeat the procedure with varying products and beauty routines and update the profile based on the results.

Systems for Indicating and/or Transmitting Measurements

In one example implementation, the status of the tissue condition (including hydration status) may be monitored with a series of LED indicator lights. That is, the LED lights can be used according of any of the examples described herein to provide the indication of the tissue condition.

As one example of many ways to illustrate the value or the change in value of tissue condition (including hydration levels), LED indicator lights may be lit to indicate the percent change in sensor measurement from the initial reading. The LEDs are grouped in pairs which light up together depending upon hydration level as displayed in the table below:

| LED Indication | Change in Measurement |
|---|---|
| Pair #1 (Green) | 0-1% |
| Pair #2 (Green) | 1-3% |
| Pair #3 (Yellow) | 3-5% |
| Pair #4 (Yellow) | 5-7% |
| Pair #5 (Orange) | 7-9% |
| Pair #6 (Orange) | 9-10% |
| Pair #7 (Red) | Over 10% |

All LED indicators leading up to the specific measurement change can remain lit, but they may go off if/when the subject rehydrates. For example, at a 4% change in a measurement, two green pairs and one yellow pair of LEDs may be lit. If that increase drops to 0.5%, only one green pair may be lit.

This is one example of many ways in which indication of hydration level may be presented to the user. Numerical seven-segment LED or LCD displays can also be used to provide numerical or percentage values. Linear arrangements of LEDs can 'chart' hydration levels where longer runs of illuminated LEDs indicate greater hydration. Brightness level can also indicate hydration level or sequential patterns or other many ways to indicate increasing, decreasing or absolute values of hydration levels may be displayed and made integral to the unit.

In yet other implementations, rather than employing external power sources, "on-board" power sources may be employed. In one instantiation, the power source may be a small 12V battery contained in rigid housing. Such power management techniques can use a variety of well-known battery and energy storage management methods.

In another aspect, data transmissions to a cellular phone, portable music player, such as an mp3 player, or other mobile device in order may be supported to allow for data logging and audible hydration status alerts via an accompanying software application. In one example, processing circuitry as well as a Bluetooth data transmitter (or other wireless techniques such as WiFi (802.11 protocols), ANT or other wireless means and protocols) are employed to facilitate such transmission.

In yet another aspect, the LED light indicator system may be replaced or supplemented by other indication mechanisms. For example, the LED light indicator system may be replaced by a display which gives a precise read out of the percent change in sensor measurement from a previously measured baseline, and therefore of the percent change in hydration level. Another solution is to remove on-board indication and require integration with a mobile device or mp3 player. This takes advantage of processing power that is available within the phone or other mobile device and reduce or eliminate processing resources on the sport band.

According to other examples, hydration monitoring apparatus may include a thin, flexible and/or stretchable capacitance-based sensor on a conformal substrate. The sensor electrode is a passive device and is applied to the skin in a variety of locations like a decal or temporary tattoo, or it may be integrated into form-fitted clothing. The capacitance-impedance between the conductive structures are measured and correlated with the state of hydration.

According to yet other examples, hydration monitoring apparatus may include a thin, flexible and/or stretchable inductor structure (such as but not limited to a RF inductor coil) on a conformal substrate. The coil is a passive device and is applied to the skin in a variety of locations like a decal or temporary tattoo, or it may be integrated into form-fitted clothing. The coil needs can be placed near the skin and does not have to be direct contact. The resonance frequency of the coil is then measured and correlated with the state of hydration.

Such information about tissue condition (including hydration) may be stored, transmitted and recorded to tie into other health information from a particular activity or series of activities to give a long term profile of body hydration over time. This information may be furthered integrated into other health related information over time and presented to the user, parent, doctor, coach or other interested party, in a software application or in web-based tools, to give graphical and visual information of status over time. This may be used to spot trends and provide early diagnosis of issues related to hydration and other physiological signs.

The information can also be used in ways to automatically update such health status and information to social media sites and forums to allow friends, fellow athletes and colleagues to compare and contrast similar information in a convenient form. Additional features would allow comments and other communication in an online fashion to provide competitive information and entertainment.

The apparatus is applied to locations where skin or muscle hydration is to be monitored. A baseline reading is taken at the beginning of an active period, and then measurements are taken periodically. Changes in the electrical information from the measurement can be correlated with changes in tissue condition, such as but not limited to hydration state.

Specific activity may be tied to specific changes in the hydration state, such as changes in level of activity, drinking more water, or other fluids such as a sport drink, or applying certain creams or lotions that change the hydration level of the skin.

For apparatus that include components for measuring based on ultrasound techniques, the apparatus may be wrapped around the user's upper arm (the biceps/triceps area), as illustrated in FIG. 26A, or lower leg (the calf) and secured using means such as, but not limited to, adhesives or hook-and-loop style fasteners (commercially available as VELCRO®) components. The apparatus is then powered on and a baseline ultrasound velocity reading is taken before activity begins. The apparatus may be used regardless of clothing or other equipment used, so long as the apparatus has direct contact with the skin.

Hydration Monitoring

Various examples of the present disclosure provide a direct, specific targeting of the use case for the hydration monitor. The specific medical applications can be broad, but specifically this can have an application for wound healing, rehabilitation, detoxification, and monitoring while in and out of the hospital for hydration levels.

With wound healing and physical rehabilitation, dehydration can result in diminished healing ability since water is a major component of healthy cells. A large, exposed wound—or even a draining wound—may also exude a large amount of fluids, resulting in dehydration and electrolyte imbalance. Maintaining body cell mass helps promote wound healing. The body enters a type of hypermetabolic state during wound healing as an increase of 10-50% of energy expenditure is common during the repair and recovery process. This hypermetabolic state can lead to dehydration, and dehydration can then affect the breakdown of proteins that are absolutely crucial in the healing process, as water aids the body in nutrient absorption and deployment. Hydration plays a role in wound healing as dehydrated skin is less elastic, more fragile and more susceptible to breakdown. Dehydration can also reduce efficiency of blood circulation, which can impair the supply of oxygen and nutrients to the wound. Water and hydration play a massive role in the healing process.

During the detoxification process, hydration plays a role in the body's function to excrete toxins and waste. Hydration is the foundation for detoxification based on a flow of water in and out of the cells. pH balance in the body is dependent on detoxification of built up toxins inside the cells. Water and hydration plays a role in this process, and it has been shown that people do not drink enough water on a daily basis to maintain an optimal level of hydration that rids the body of toxins and provides an overall health and wellness well being. Those who have lived for many years without proper water intake are the most likely to succumb to the buildup of toxins in the body. It is difficult to perform accurate monitoring of the level of tissue hydration on a day-to-day basis—other than the crude method of comparing colors of urine. This hydration monitor can provide a way for people to lead a healthier life through all of the benefits of hydration (signs of dehydration range from drops in physical and mental performance, migraines, muscle aches, and constipation, to even more severe episodes requiring hospitalization).

Monitoring patients (even self-monitoring) while in and out of the hospital for hydration levels can be beneficial when considering the extremely dehydrating effects of painkillers and antibiotics. Just as in wound healing above, the body has an increased need for hydration while taking painkillers and antibiotics. Many painkillers and many antibiotics have a dehydrating effect on the body, thus making it difficult to recover from injury. Painkillers have a double effect, they use a large amount of cellular water to be processed, and they also mute the body's natural response to dehydration; thirst. The process of progressive cellular dehydration can occur over time. Also, many antibiotics cause diarrhea, which can cause severe dehydration over time. Monitoring levels of dehydration is both preventative and pro-active in this setting.

There is also an application for the weight-loss market for the hydration monitor. Staying hydrated is very important in general health/well-being from day-to-day (focus benefits, short-term health, long-term health, etc.) but it has been well-documented that far too many people just do not drink enough water throughout the day and can develop dehydration that can be chronic. The diet and/or athletics industry may derive great benefit by using hydration as a way to manage appetite, leading to healthy weight loss and a healthy life style at a very low-cost with no side effects. Water is a form of hydration that is readily available and very inexpensive. It has long been known that water is the essential key to weight loss by suppressing appetite (the "full-feeling", reducing caloric intake when properly hydrated, etc.), boosting metabolism, and increasing energy production. Hydration studies have shown that dehydration can affect both mood and willpower: a poor mood and willpower makes you much more likely to eat food high in fat, sugar and calories. Proper hydration brings an absolute huge shift in the diet/fitness market, and the monitors described herein facilitate that. In non-limiting example implementation, the apparatus is used as a hydration monitor.

The data provided by an apparatus or system herein, in performing a capacitance-based or an inductance-based measurement, can be used to determine the timing of replacing body fluids. Not replacing enough fluids and electrolytes lost can lead to severe cramping, drop-off in athletic performance, and mental confusion that can be traced to the changes at cellular level upon dehydration. Replacing too much fluids and electrolytes can lead to an electrolyte imbalance and gastrointestinal problems, not to mention a bloated, full feeling while in competition or training Changes in temperature, humidity, altitude, level of activity and the degree of heat acclimation the athlete or soldier has further complicates the process. Measuring the loss of fluids from the skin can be a reliable way to measure dehydration or more generally the state of hydration in real-time.

The apparatus and systems described herein can provide a real-time proxy for total volume of sweat lost in a workout/practice/game/battle/training or any specified period of time from when the monitor is placed on the body. Thus, the issue of replacing fluids lost is made simpler; replace what is lost in real-time during the activity, training or battle, thus assisting to reduce or substantially eliminate avoiding the drop-off in performance mentally and physically.

Conclusion

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While various examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine measurementation, many equivalents to the specific examples described herein. It is, therefore, to be understood that the foregoing examples are presented by way of example only and that, within the scope of the appended claims and equivalents thereto, examples may be practiced otherwise than as specifically described and claimed. examples of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described examples of the invention can be implemented in any of numerous ways. For example, some examples may be implemented using hardware, software or a combination thereof. When any aspect of an example is implemented at least in part in software, the software code can be executed on any suitable processor or collection of processors, whether provided in a single device or computer or distributed among multiple devices/computers.

In this respect, various aspects of the invention, may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various examples of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this example, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various examples.

Also, the technology described herein may be embodied as a method, of which at least one example has been provided. The acts performed as part of the method may be ordered in any suitable way. Accordingly, examples may be constructed in which acts are performed in an order different than illustrated, which may include performing some acts simultaneously, even though shown as sequential acts in illustrative examples.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one example, to A only (optionally including elements other than B); in another example, to B only (optionally including elements other than A); in yet another example, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one example, to at least one, optionally including more than one, A, with no B present (and optionally including elements other than B); in another example, to at least one, optionally including more than one, B, with no A present (and optionally including elements other than A); in yet another example, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All examples that come within the spirit and scope of the following claims and equivalents thereto are claimed.

What is claimed is:

1. An apparatus disposed on tissue for monitoring a condition of the tissue, the apparatus comprising:

a first plurality of conductive structures, each of the conductive structures in the first plurality of conductive structures having a non-linear configuration that facilitates flexibility of the first plurality of conductive structures to flexing, stretching, or torsion of the tissue to which the apparatus is disposed upon, thereby aiding in maintaining the first plurality of conductive structures in contact with the tissue;

a second plurality of conductive structures, each of the conductive structures in the second plurality of conductive structures having a non-linear configuration that facilitates flexibility of the second plurality of conductive structures to flexing, stretching, or torsion of the tissue to which the apparatus is disposed upon, thereby aiding in maintaining the second plurality of conductive structures in contact with the tissue, each of the conductive structures in the second plurality of conductive structures being disposed substantially parallel to each of the conductive structures in the first plurality of conductive structures in an alternating and interdigitated configuration;

a first brace structure disposed substantially perpendicular to each of the conductive structures in the first plurality of conductive structures, the first brace structure being electrically coupled to each of the conductive structures in the first plurality of conductive structures;

a second brace structure disposed substantially perpendicular to each of the conductive structures in the second plurality of conductive structures, the second brace structure being electrically coupled to each of the conductive structures in the second plurality of conductive structures, wherein the first brace structure and the second brace structure aid in maintaining a substantially uniform separation between each of the conductive structures in the first plurality of conductive structures and each of the immediately adjacent conductive structures in the second plurality of conductive structures; and a non-conducting spacer structure having a first end and a second end, the first end of the non-conducting spacer structure being physically coupled to the first brace structure and the second end of the non-conducting spacer structure being physically coupled to the second brace structure such that the non-conducting spacer structure aids in (i) maintaining a substantially uniform separation between the first brace structure and the second brace structure and (ii) maintaining a substantially uniform form factor of the apparatus during deformation of the apparatus, wherein a capacitive based measurement performed by applying a potential across one of the conductive structures in the first plurality of conductive structures and a directly adjacent one of the conductive structures in the second plurality of conductive structures provides an indication of the condition of the tissue.

2. The apparatus of claim 1, wherein the condition of the tissue is a hydration state of the tissue, a volume of sweat lost, a mechanical property of the tissue, or a disease state of the tissue.

3. The apparatus of claim 1, wherein each of the conductive structures in the first plurality of conductive structures and each of the conductive structures in the second plurality of conductive structures has a zig-zag configuration, a serpentine configuration, or a rippled configuration.

4. The apparatus of claim 1, wherein the first brace structure and the second brace structure are both formed from a conductive material, and wherein the first brace structure electrically links the first plurality of conductive structures to an external circuit, and wherein the second brace structure electrically links the second plurality of conductive structures to the external circuit.

5. The apparatus of claim 1, wherein the non-conducting spacer structure is disposed substantially parallel to a principal direction of the first plurality of conductive structures and the second plurality of conductive structures.

6. The apparatus of claim 1, wherein the first brace structure is in electrical communication with a first electrical contact of the apparatus and the second brace structure is in electrical communication with a second electrical contact of the apparatus, and wherein the first electrical contact and the second electrical contact are in electrical communication with at least one of a power source, a wireless receiver, a wireless transmitter, a wireless transceiver, and a temperature sensor.

7. The apparatus of claim 1, further comprising a plurality of cross-link structures disposed between directly adjacent conductive structures, each cross-link structure of the plurality of cross-link structures being formed from a dielectric material.

8. The apparatus of claim 1, further comprising an encapsulation layer disposed over at least a portion of the first plurality of conductive structures and the second plurality of conductive structures.

9. The apparatus of claim 8, wherein portions of the encapsulation layer comprise an adhesive, and wherein the adhesive is configured to attach the portions of the encapsulation layer to the tissue.

10. The apparatus of claim 8, further comprising a plurality of cross-link structures disposed between directly adjacent conductive structures, each cross-link structure of the plurality of cross-link structures being formed from the same material as the encapsulation layer.

11. The apparatus of claim 8, wherein the encapsulation layer is a polymer.

12. The apparatus of claim 11, wherein the polymer is a polyimide.

13. The apparatus of claim 1, further comprising a backing layer in physical communication with at least a portion of the first plurality of conductive structures and the second plurality of conductive structures, wherein the backing layer is a polymer.

14. The apparatus of claim 1, further comprising an ultrasound apparatus, and wherein the ultrasound apparatus provides a measure of a condition of the tissue.

15. The apparatus of claim 14, wherein the ultrasound apparatus comprises:
an ultrasound generator configured to be disposed proximate to a first portion of the tissue of interest, wherein the ultrasound generator comprises a piezoelectric crystal, wherein the ultrasound generator directs ultrasound waves at a portion of the tissue; and
an ultrasound receiver configured to be disposed proximate to a second portion of the tissue of interest that is different from the first portion,
wherein the ultrasound receiver provides a measure of ultrasound waves arriving at the second portion of the tissue, and
wherein the measure of ultrasound waves arriving at the second portion of the tissue provides an indication of the condition of the tissue.

16. The apparatus of claim 1, further comprising at least one of the following:
a battery, a transmitter, a transceiver, a memory, a radio-frequency identification (RFID) chip, a processing unit, an analog sensing block, a UVA sensor, a UVB sensor, and a temperature sensor.

17. A method for monitoring a condition of a tissue, the method comprising:
receiving data indicative of the measurement, wherein the measurement is performed using at least one the apparatus of claim 1; and
analyzing the received data using at least one processor unit, the analysis providing the indication of the condition of the tissue.

18. The method of claim 17, wherein the analyzing the received data comprises applying an effective circuit model to the data, and wherein a value of a parameter of the model provides the indication of the condition of the tissue.

19. The method of claim 17, wherein the analyzing the received data comprises comparing the data to a calibration standard, and wherein the comparing provides the indication of the condition of the tissue.

20. The method of claim 19, wherein the calibration standard comprises a correlation between values of capacitive-based measurement and the indication of the condition of the tissue.

21. An apparatus for monitoring a condition of a tissue, the apparatus comprising:
at least two conductive structures configured to be disposed above the tissue and running substantially parallel to each other along substantially an entire length of the at least two conductive structures, wherein each of the at least two conductive structures has a non-linear configuration, and where the at least two conductive structures are arranged in a curved configuration that facilitates flexibility of the apparatus to flexing, stretching or torsion of the tissue to thereby maintain the apparatus in contact with the tissue, wherein each of the at least two conductive structures maintains a separation of neighboring conductive structures of the at least two conductive structures to a substantially uniform value of distance;
at least two contact structures, each being in electrical communication with at least one of the at least two parallel conductive structures;
at least two non-conductive spacer structures, each of the at least two non-conductive spacer structures non-conductively coupling at least one of the at least two conductive structures to one of the at least two contact structures; and
wherein a capacitive-based measurement performed by applying a potential across one of the at least two conductive structures and a directly adjacent one of the at least two conductive structures provides a measure of the condition of the tissue.

22. The apparatus of claim 21, wherein the condition of the tissue is a hydration state of the tissue, a volume of sweat lost, a mechanical property of the tissue, or a disease state of the tissue.

23. The apparatus of claim 21, wherein each of the plurality of conductive structures has a zig-zag configuration, a serpentine configuration, or a rippled configuration.

24. The apparatus of claim 21, wherein each of the at least two contact structures electrically links the at least two conductive structures to an external circuit.

25. The apparatus of claim 21, wherein each of the at least two contact structures is in electrical communication with at least one of a power source, a wireless receiver, a wireless transmitter, a wireless transceiver, and a temperature sensor.

26. The apparatus of claim 21, further comprising an encapsulation layer disposed over at least a portion of the at least two conductive structures.

27. The apparatus of claim 26, wherein portions of the encapsulation layer comprise an adhesive, and wherein the adhesive is configured to attach the portions of the encapsulation layer to the tissue.

28. The apparatus of claim 27, wherein the encapsulation layer is a polymer.

29. The apparatus of claim 28, wherein the polymer is a polyimide.

30. The apparatus of claim 21, further comprising at least one cross-link structure coupled at each end thereof to a portion of each of the least two conductive structures.

31. The apparatus of claim 30, wherein each of the at least one cross-link structure is disposed substantially perpendicularly to the portion of the at least two substantially parallel conductive structures.

32. The apparatus of claim 21, further comprising a plurality of cross-link structures disposed between the at least two conductive structures, each cross-link structure of the plurality of cross-link structures being formed from a dielectric material.

33. The apparatus of claim 32, further comprising a plurality of cross-link structures disposed between neighboring conductive structures, each cross-link structure of the plurality of cross-link structures being formed from the same material as the encapsulation layer.

34. The apparatus of claim 33, wherein the encapsulation layer is a polymer.

35. The apparatus of claim 34, wherein the polymer is a polyimide.

36. The apparatus of claim 21, further comprising a backing layer in physical communication with at least a portion of the at least two conductive structures, wherein the backing layer is a polymer.

37. The apparatus of claim 21, further comprising an ultrasound apparatus, and wherein the ultrasound apparatus provides a measure of a condition of the tissue.

38. The apparatus of claim 37, wherein the ultrasound apparatus comprises:
an ultrasound generator configured to be disposed proximate to a first portion of the tissue of interest, wherein the ultrasound generator comprises a piezoelectric crystal, wherein the ultrasound generator directs ultrasound waves at a portion of the tissue; and
an ultrasound receiver configured to be disposed proximate to a second portion of the tissue of interest that is different from the first portion,
wherein the ultrasound receiver provides a measure of ultrasound waves arriving at the second portion of the tissue, and
wherein the measure of ultrasound waves arriving at the second portion of the tissue provides an indication of the condition of the tissue.

39. The apparatus of claim 21, further comprising at least one of the following:
a battery, a transmitter, a transceiver, a memory, a radio-frequency identification (RFID) chip, a processing unit, an analog sensing block, a UVA sensor, a UVB sensor, and a temperature sensor.

40. A method for monitoring a condition of a tissue, the method comprising:
receiving data indicative of the capacitive-based measurement, wherein the capacitive-based measurement is performed using the apparatus of claim 21; and
analyzing the received data using at least one processor unit, the analysis providing an the indication of the condition of the tissue.

41. The method of claim 40, wherein the analyzing the received data comprises applying an effective circuit model to the data, and wherein a value of a parameter of the model provides the indication of the condition of the tissue.

42. The method of claim 40, wherein the analyzing the received data comprises comparing the data to a calibration standard, and wherein the comparing provides the indication of the condition of the tissue.

43. The method of claim 42, wherein the calibration standard comprises a correlation between values of capacitive-based measurement and the indication of the condition of the tissue.

44. The apparatus of claim 1, further comprising a second non-conducting spacer structure having a first end and a second end, the first end of the second non-conducting spacer structure being physically coupled to the first brace structure and the second end of the second non-conducting spacer structure being physically coupled to the second brace structure.

45. The apparatus of claim 1, wherein the first plurality of conductive structures includes semiconductor material and the second plurality of conductive structures includes semiconductor material.

46. The apparatus of claim 8, wherein the encapsulation layer includes polyurethane.

47. The apparatus of claim 21, wherein the at least two conductive structures includes semiconductor material.

48. The apparatus of claim 27, wherein the encapsulation layer includes polyurethane.

* * * * *

UNITED STATES PATENT AND TRADEMARK OFFICE
CERTIFICATE OF CORRECTION

PATENT NO. : 9,579,040 B2  
APPLICATION NO. : 13/603290  
DATED : February 28, 2017  
INVENTOR(S) : Conor Rafferty et al.

It is certified that error appears in the above-identified patent and that said Letters Patent is hereby corrected as shown below:

In the Claims

At Column 42, Lines 8-9, Claim 17, replace "measurement is performed using at least one the apparatus of claim 1; and" with --measurement is performed using the apparatus of claim 1; and--.

Signed and Sealed this  
Second Day of May, 2017

Michelle K. Lee  
*Director of the United States Patent and Trademark Office*